US010913960B2

(12) United States Patent
Schaffer et al.

(10) Patent No.: US 10,913,960 B2
(45) Date of Patent: Feb. 9, 2021

(54) BIOTECHNOLOGICAL PRODUCTION OF OMEGA-FUNCTIONALISED CARBOXYLIC ACIDS AND ESTERS THEREOF

(71) Applicant: Evonik Operations GmbH, Essen (DE)

(72) Inventors: Steffen Schaffer, Herten (DE); Thomas Haas, Muenster (DE); Wilhelm Bruegging, Haltern am See (DE); Ralf Meier, Dortmund (DE)

(73) Assignee: Evonik Operations GmbH, Essen (DE)

( * ) Notice: Subject to any disclaimer, the term of this patent is extended or adjusted under 35 U.S.C. 154(b) by 118 days.

(21) Appl. No.: 15/359,932

(22) Filed: Nov. 23, 2016

(65) Prior Publication Data
US 2017/0145448 A1   May 25, 2017

(30) Foreign Application Priority Data
Nov. 25, 2015 (EP) .................................... 15196180

(51) Int. Cl.
| C12P 7/62 | (2006.01) |
| C12N 15/52 | (2006.01) |
| C12P 7/64 | (2006.01) |
| C12P 7/02 | (2006.01) |
| C12P 7/24 | (2006.01) |
| C12N 9/04 | (2006.01) |
| C12N 9/02 | (2006.01) |
| C12N 9/10 | (2006.01) |

(52) U.S. Cl.
CPC .............. *C12P 7/62* (2013.01); *C12N 9/0006* (2013.01); *C12N 9/0077* (2013.01); *C12N 9/1029* (2013.01); *C12N 9/1096* (2013.01); *C12N 15/52* (2013.01); *C12P 7/02* (2013.01); *C12P 7/24* (2013.01); *C12P 7/649* (2013.01); *C12P 7/6436* (2013.01); *C12Y 101/01001* (2013.01); *C12Y 101/01002* (2013.01); *C12Y 101/0302* (2013.01); *C12Y 114/15003* (2013.01); *C12Y 203/01075* (2013.01); *C12Y 203/01084* (2013.01); *C12Y 206/01* (2013.01); *Y02E 50/10* (2013.01)

(58) Field of Classification Search
CPC .... C12N 15/52; C12N 9/1029; C12N 9/1096; C12N 9/0006; C12N 9/0077; C12P 7/6436; C12P 7/62; C12P 7/649; C12Y 101/01002; C12Y 101/01001; C12Y 101/0302; C12Y 114/15003; C12Y 203/01075; C12Y 203/01084; C12Y 206/01
See application file for complete search history.

(56) References Cited

U.S. PATENT DOCUMENTS

| 8,372,595 B2 | 2/2013 | Schaffer et al. |
| 8,378,127 B2 | 2/2013 | Dingerdissen et al. |
| 8,703,451 B2 | 4/2014 | Haas et al. |
| 8,809,576 B2 | 8/2014 | Schraven et al. |
| 8,980,594 B2 | 3/2015 | Reinecke et al. |
| 8,986,961 B2 | 3/2015 | Verseck et al. |
| 9,012,227 B2 | 4/2015 | Karau et al. |
| 9,200,043 B2 | 12/2015 | Pötter et al. |
| 2011/0072714 A1 | 3/2011 | Gaertner |
| 2011/0162259 A1 | 7/2011 | Gaertner |
| 2013/0078684 A1* | 3/2013 | Holtzapple ............ C12N 15/70 435/134 |
| 2014/0256904 A1 | 9/2014 | Schaffer et al. |
| 2016/0333325 A1 | 11/2016 | Gaertner |

FOREIGN PATENT DOCUMENTS

| WO | WO 99/04014 A2 | 1/1999 |
| WO | WO 99/04014 A3 | 1/1999 |
| WO | WO 2008/119082 A2 | 10/2008 |
| WO | WO 2008/119082 A3 | 10/2008 |

OTHER PUBLICATIONS

Kok et al., GenBank accession No. CAB54050.1, Jul. 26, 2016.*
Witkowski et al., Biochemistry 38:11643-11650, 1999.*
Tang et al., Phil Trans R Soc B 368:20120318, 1-10, 2013.*
Seffernick et al., J. Bacteriol. 183(8):2405-2410, 2001.*
Branden et al., Introduction to Protein Structure, Garland Publishing Inc., New York, p. 247, 1991.*
Sadowski et al., Current Opinion in Structural Biology 19:357-362, 2009.*
Zhou et al., Cell Mol Life Sci 63(19-20):2260-2290, 2006.*
Kozak, M., Gene 234:187-208, 1999.*
Guo et al., PNAS 101(25):9205-9210, 2004.*
Extended European Search Report dated Mar. 2, 2016 in Patent Application No. 15196180.2.
Extended European Search Report dated Dec. 16, 2016 in Patent Application No. 16199533.7.
U.S. Appl. No. 15/359,932, filed Nov. 23, 2016, Schaffer, et al.
U.S. Appl. No. 13/001,204, filed Jul. 14, 2011, 2011/0171702, Reinecke, et al.
U.S. Appl. No. 14/126,607, filed May 1, 2014, 2014/0120587, Haas, et al.

(Continued)

*Primary Examiner* — Delia M Ramirez
(74) *Attorney, Agent, or Firm* — Oblon, McClelland, Maier & Neustadt, L.L.P.

(57) ABSTRACT

A microbial cell, which is genetically modified to increase the expression relative to the corresponding genetically unmodified cell of an AlkB alkane hydroxylase ($E_b$) having an amino acid sequence at least 95% identical with the amino acid sequence of SEQ ID NO: 1 and a wax-ester synthase ($E_f$) having an amino acid sequence at least 95% identical with the amino acid sequence of SEQ ID NO: 2. The cell does not have a genetic modification that increases formation of a carboxylic acid or a carboxylate ester from a simple carbon source.

18 Claims, No Drawings

Specification includes a Sequence Listing.

(56) References Cited

OTHER PUBLICATIONS

U.S. Appl. No. 15/073,105, filed Aug. 25, 2016, 2016/0244790, Haas, et al.
U.S. Appl. No. 14/238,576, filed Jul. 3, 2014, 2014/0186905, Schaffer, et al.
U.S. Appl. No. 14/238,591, filed Sep. 11, 2014, 2014/0256904, Schaffer, et al.
U.S. Appl. No. 14/363,178, filed Aug. 6, 2015, 2015/0218600, Haas, et al.
U.S. Appl. No. 14/390,133, filed Apr. 23, 2015, 2015/0111254, Hennemann, et al.
U.S. Appl. No. 14/400,379, filed May 7, 2015, 2015/0125912, Haas, et al.
U.S. Appl. No. 14/380,483, filed Oct. 8, 2015, 2015/0284747, Schiemann, et al.
U.S. Appl. No. 14/367,610, filed Oct. 1, 2015, 2015/0275245, Haas, et al.
U.S. Appl. No. 14/373,089, filed Jan. 8, 2015, 2015/0010968, Engel, et al.
U.S. Appl. No. 14/384,301, filed Apr. 23, 2015, 2015/0111253, Schaffer, et al.
U.S. Appl. No. 14/395,666, filed Apr. 9, 2015, 2015/0099282, Haas, et al.
U.S. Appl. No. 14/405,050, filed Sep. 24, 2015, 2015/0267231, Haas, et al.
U.S. Appl. No. 14/898,417, filed May 19, 2016, 2016/0138058, Wittmann, et al.
U.S. Appl. No. 14/435,339, filed Oct. 22, 2015, 2015/0299741, Engel, et al.
U.S. Appl. No. 14/077,750, filed May 22, 2014, 2014/0141478, Schaffer, et al.
U.S. Appl. No. 14/132,473, filed Jun. 26, 2014, 2014/0178948, Schaffer, et al.
U.S. Appl. No. 14/763,378, filed Dec. 10, 2015, 2015/0353963, Haas, et al.
U.S. Appl. No. 14/915,012, filed Sep. 22, 2016, 2016/0272950, Corthals, et al.
U.S. Appl. No. 14/943,333, filed May 19, 2016, 2016/0138061, Haas, et al.
U.S. Appl. No. 15/111,640, filed Nov. 10, 2016, 2016/0326555, Engel, et al.
U.S. Appl. No. 14/843,525, filed Mar. 3, 2016, 2016/0060663, Grammann, et al.
U.S. Appl. No. 15/009,425, filed Jul. 28, 2016, 2016/0215302, Haas, et al.
U.S. Appl. No. 14/391,480, filed Apr. 30, 2015, 2015/0118721, Schaffer, et al.
U.S. Appl. No. 14,649,414, filed Oct. 29, 2015, 2015-0307906, Schaffer, et al.
U.S. Appl. No. 15/309,994, filed Sep. 14, 2017, 2017-260552, Haas et al.
U.S. Appl. No. 15/312,627, filed May 11, 2017, 2017-0130248, Reinecke et al.
U.S. Appl. No. 15/579,442, filed Dec. 7, 2017, Haas et al.
U.S. Appl. No. 15/359,932, filed May 25, 2017, 2017-0145448, Schaffer et al.
Mexican Office Action dated Mar. 6, 2020, in Mexican Patent Application No. MX/a/2016/015380 (with English Translation).
Lohaus; Meyer, Biospektrum, (1989), vol. 5, pp. 32-39.
Lottspeich, Angewandte Chemie, (1999), vol. 111, pp. 2630-2647.
Russian Office Action dated Apr. 30, 2020, in Russian Patent Application No. 2016146334 (with English Translation).

* cited by examiner

SEQUENCE LISTING

```
<160> NUMBER OF SEQ ID NOS: 7

<210> SEQ ID NO 1
<211> LENGTH: 401
<212> TYPE: PRT
<213> ORGANISM: Pseudomonas putida

<400> SEQUENCE: 1

Met Leu Glu Lys His Arg Val Leu Asp Ser Ala Pro Glu Tyr Val Asp
1               5                   10                  15

Lys Lys Lys Tyr Leu Trp Ile Leu Ser Thr Leu Trp Pro Ala Thr Pro
            20                  25                  30

Met Ile Gly Ile Trp Leu Ala Asn Glu Thr Gly Trp Gly Ile Phe Tyr
        35                  40                  45

Gly Leu Val Leu Leu Val Trp Tyr Gly Ala Leu Pro Leu Leu Asp Ala
    50                  55                  60

Met Phe Gly Glu Asp Phe Asn Asn Pro Pro Glu Glu Val Val Pro Lys
65                  70                  75                  80

Leu Glu Lys Glu Arg Tyr Tyr Arg Val Leu Thr Tyr Leu Thr Val Pro
```

```
                    85                  90                  95
Met His Tyr Ala Ala Leu Ile Val Ser Ala Trp Trp Val Gly Thr Gln
                100                 105                 110

Pro Met Ser Trp Leu Glu Ile Gly Ala Leu Ala Leu Ser Leu Gly Ile
            115                 120                 125

Val Asn Gly Leu Ala Leu Asn Thr Gly His Glu Leu Gly His Lys Lys
        130                 135                 140

Glu Thr Phe Asp Arg Trp Met Ala Lys Ile Val Leu Ala Val Val Gly
145                 150                 155                 160

Tyr Gly His Phe Phe Ile Glu His Asn Lys Gly His His Arg Asp Val
                165                 170                 175

Ala Thr Pro Met Asp Pro Ala Thr Ser Arg Met Gly Glu Ser Ile Tyr
            180                 185                 190

Lys Phe Ser Ile Arg Glu Ile Pro Gly Ala Phe Ile Arg Ala Trp Gly
        195                 200                 205

Leu Glu Glu Gln Arg Leu Ser Arg Arg Gly Gln Ser Val Trp Ser Phe
    210                 215                 220

Asp Asn Glu Ile Leu Gln Pro Met Ile Ile Thr Val Ile Leu Tyr Ala
225                 230                 235                 240

Val Leu Leu Ala Leu Phe Gly Pro Lys Met Leu Val Phe Leu Pro Ile
                245                 250                 255

Gln Met Ala Phe Gly Trp Trp Gln Leu Thr Ser Ala Asn Tyr Ile Glu
            260                 265                 270

His Tyr Gly Leu Leu Arg Gln Lys Met Glu Asp Gly Arg Tyr Glu His
        275                 280                 285

Gln Lys Pro His His Ser Trp Asn Ser Asn His Ile Val Ser Asn Leu
    290                 295                 300

Val Leu Phe His Leu Gln Arg His Ser Asp His Ala His Pro Thr
305                 310                 315                 320

Arg Ser Tyr Gln Ser Leu Arg Asp Phe Pro Gly Leu Pro Ala Leu Pro
                325                 330                 335

Thr Gly Tyr Pro Gly Ala Phe Leu Met Ala Met Ile Pro Gln Trp Phe
            340                 345                 350

Arg Ser Val Met Asp Pro Lys Val Val Asp Trp Ala Gly Gly Asp Leu
        355                 360                 365

Asn Lys Ile Gln Ile Asp Asp Ser Met Arg Glu Thr Tyr Leu Lys Lys
    370                 375                 380

Phe Gly Thr Ser Ser Ala Gly His Ser Ser Ser Thr Ser Ala Val Ala
385                 390                 395                 400

Ser

<210> SEQ ID NO 2
<211> LENGTH: 458
<212> TYPE: PRT
<213> ORGANISM: Hahella chejuensis

<400> SEQUENCE: 2

Met Thr Pro Leu Ser Pro Val Asp Gln Ile Phe Leu Trp Leu Glu Lys
1               5                   10                  15

Arg Gln Gln Pro Met His Val Gly Gly Leu His Ile Phe Ser Phe Pro
                20                  25                  30

Asp Asp Ala Asp Ala Lys Tyr Met Thr Glu Leu Ala Gln Gln Leu Arg
            35                  40                  45

Ala Tyr Ala Thr Pro Gln Ala Pro Phe Asn Arg Arg Leu Arg Gln Arg
```

```
            50                  55                  60
Trp Gly Arg Tyr Tyr Trp Asp Thr Asp Ala Gln Phe Asp Leu Glu His
 65                  70                  75                  80

His Phe Arg His Glu Ala Leu Pro Lys Pro Gly Arg Ile Arg Glu Leu
                 85                  90                  95

Leu Ala His Val Ser Ala Glu His Ser Asn Leu Met Asp Arg Glu Arg
            100                 105                 110

Pro Met Trp Glu Cys His Leu Ile Glu Gly Ile Arg Gly Arg Arg Phe
            115                 120                 125

Ala Val Tyr Tyr Lys Ala His His Cys Met Leu Asp Gly Val Ala Ala
        130                 135                 140

Met Arg Met Cys Val Lys Ser Tyr Ser Phe Asp Pro Thr Ala Thr Glu
145                 150                 155                 160

Met Pro Pro Ile Trp Ala Ile Ser Lys Asp Val Thr Pro Ala Arg Glu
                165                 170                 175

Thr Gln Ala Pro Ala Ala Gly Asp Leu Val His Ser Leu Ser Gln Leu
            180                 185                 190

Val Glu Gly Ala Gly Arg Gln Leu Ala Thr Val Pro Thr Leu Ile Arg
        195                 200                 205

Glu Leu Gly Lys Asn Leu Leu Lys Ala Arg Asp Asp Ser Asp Ala Gly
    210                 215                 220

Leu Ile Phe Arg Ala Pro Pro Ser Ile Leu Asn Gln Arg Ile Thr Gly
225                 230                 235                 240

Ser Arg Arg Phe Ala Ala Gln Ser Tyr Ala Leu Glu Arg Phe Lys Ala
                245                 250                 255

Ile Gly Lys Ala Phe Gln Ala Thr Val Asn Asp Val Val Leu Ala Val
            260                 265                 270

Cys Gly Ser Ala Leu Arg Asn Tyr Leu Leu Ser Arg Gln Ala Leu Pro
        275                 280                 285

Asp Gln Pro Leu Ile Ala Met Ala Pro Met Ser Ile Arg Gln Asp Asp
    290                 295                 300

Ser Asp Ser Gly Asn Gln Ile Ala Met Ile Leu Ala Asn Leu Gly Thr
305                 310                 315                 320

His Ile Ala Asp Pro Val Arg Arg Leu Glu Leu Thr Gln Ala Ser Ala
                325                 330                 335

Arg Glu Ser Lys Glu Arg Phe Arg Gln Met Thr Pro Glu Glu Ala Val
            340                 345                 350

Asn Tyr Thr Ala Leu Thr Leu Ala Pro Ser Gly Leu Asn Leu Leu Thr
        355                 360                 365

Gly Leu Ala Pro Lys Trp Gln Ala Phe Asn Val Val Ile Ser Asn Val
    370                 375                 380

Pro Gly Pro Asn Lys Pro Leu Tyr Trp Asn Gly Ala Arg Leu Glu Gly
385                 390                 395                 400

Met Tyr Pro Val Ser Ile Pro Val Asp Tyr Ala Ala Leu Asn Ile Thr
                405                 410                 415

Leu Val Ser Tyr Arg Asp Gln Leu Glu Phe Gly Phe Thr Ala Cys Arg
            420                 425                 430

Arg Thr Leu Pro Ser Met Gln Arg Leu Leu Asp Tyr Ile Glu Gln Gly
        435                 440                 445

Ile Ala Glu Leu Glu Lys Ala Ala Gly Val
    450                 455
```

<210> SEQ ID NO 3

-continued

<211> LENGTH: 459
<212> TYPE: PRT
<213> ORGANISM: Chromobacterium violaceum

<400> SEQUENCE: 3

```
Met Gln Lys Gln Arg Thr Thr Ser Gln Trp Arg Glu Leu Asp Ala Ala
1               5                   10                  15

His His Leu His Pro Phe Thr Asp Thr Ala Ser Leu Asn Gln Ala Gly
            20                  25                  30

Ala Arg Val Met Thr Arg Gly Glu Gly Val Tyr Leu Trp Asp Ser Glu
        35                  40                  45

Gly Asn Lys Ile Ile Asp Gly Met Ala Gly Leu Trp Cys Val Asn Val
50                  55                  60

Gly Tyr Gly Arg Lys Asp Phe Ala Glu Ala Ala Arg Arg Gln Met Glu
65                  70                  75                  80

Glu Leu Pro Phe Tyr Asn Thr Phe Phe Lys Thr Thr His Pro Ala Val
                85                  90                  95

Val Glu Leu Ser Ser Leu Leu Ala Glu Val Thr Pro Ala Gly Phe Asp
            100                 105                 110

Arg Val Phe Tyr Thr Asn Ser Gly Ser Glu Ser Val Asp Thr Met Ile
        115                 120                 125

Arg Met Val Arg Arg Tyr Trp Asp Val Gln Gly Lys Pro Glu Lys Lys
130                 135                 140

Thr Leu Ile Gly Arg Trp Asn Gly Tyr His Gly Ser Thr Ile Gly Gly
145                 150                 155                 160

Ala Ser Leu Gly Gly Met Lys Tyr Met His Glu Gln Gly Asp Leu Pro
                165                 170                 175

Ile Pro Gly Met Ala His Ile Glu Gln Pro Trp Trp Tyr Lys His Gly
            180                 185                 190

Lys Asp Met Thr Pro Asp Glu Phe Gly Val Val Ala Ala Arg Trp Leu
        195                 200                 205

Glu Glu Lys Ile Leu Glu Ile Gly Ala Asp Lys Val Ala Ala Phe Val
210                 215                 220

Gly Glu Pro Ile Gln Gly Ala Gly Gly Val Ile Val Pro Pro Ala Thr
225                 230                 235                 240

Tyr Trp Pro Glu Ile Glu Arg Ile Cys Arg Lys Tyr Asp Val Leu Leu
                245                 250                 255

Val Ala Asp Glu Val Ile Cys Gly Phe Gly Arg Thr Gly Glu Trp Phe
            260                 265                 270

Gly His Gln His Phe Gly Phe Gln Pro Asp Leu Phe Thr Ala Ala Lys
        275                 280                 285

Gly Leu Ser Ser Gly Tyr Leu Pro Ile Gly Ala Val Phe Val Gly Lys
290                 295                 300

Arg Val Ala Glu Gly Leu Ile Ala Gly Gly Asp Phe Asn His Gly Phe
305                 310                 315                 320

Thr Tyr Ser Gly His Pro Val Cys Ala Ala Val Ala His Ala Asn Val
                325                 330                 335

Ala Ala Leu Arg Asp Glu Gly Ile Val Gln Arg Val Lys Asp Asp Ile
            340                 345                 350

Gly Pro Tyr Met Gln Lys Arg Trp Arg Glu Thr Phe Ser Arg Phe Glu
        355                 360                 365

His Val Asp Asp Val Arg Gly Val Gly Met Val Gln Ala Phe Thr Leu
370                 375                 380

Val Lys Asn Lys Ala Lys Arg Glu Leu Phe Pro Asp Phe Gly Glu Ile
```

```
                385                 390                 395                 400

Gly Thr Leu Cys Arg Asp Ile Phe Phe Arg Asn Asn Leu Ile Met Arg
                405                 410                 415

Ala Cys Gly Asp His Ile Val Ser Ala Pro Pro Leu Val Met Thr Arg
                420                 425                 430

Ala Glu Val Asp Glu Met Leu Ala Val Ala Glu Arg Cys Leu Glu Glu
                435                 440                 445

Phe Glu Gln Thr Leu Lys Ala Arg Gly Leu Ala
                450                 455

<210> SEQ ID NO 4
<211> LENGTH: 230
<212> TYPE: PRT
<213> ORGANISM: Pseudomonas putida

<400> SEQUENCE: 4

Met Ser Phe Ser Asn Tyr Lys Val Ile Ala Met Pro Val Leu Val Ala
1               5                   10                  15

Asn Phe Val Leu Gly Ala Ala Thr Ala Trp Ala Asn Glu Asn Tyr Pro
                20                  25                  30

Ala Lys Ser Ala Gly Tyr Asn Gln Gly Asp Trp Val Ala Ser Phe Asn
            35                  40                  45

Phe Ser Lys Val Tyr Val Gly Glu Glu Leu Gly Asp Leu Asn Val Gly
        50                  55                  60

Gly Gly Ala Leu Pro Asn Ala Asp Val Ser Ile Gly Asn Asp Thr Thr
65                  70                  75                  80

Leu Thr Phe Asp Ile Ala Tyr Phe Val Ser Ser Asn Ile Ala Val Asp
                85                  90                  95

Phe Phe Val Gly Val Pro Ala Arg Ala Lys Phe Gln Gly Glu Lys Ser
                100                 105                 110

Ile Ser Ser Leu Gly Arg Val Ser Glu Val Asp Tyr Gly Pro Ala Ile
            115                 120                 125

Leu Ser Leu Gln Tyr His Tyr Asp Ser Phe Glu Arg Leu Tyr Pro Tyr
        130                 135                 140

Val Gly Val Gly Val Gly Arg Val Leu Phe Phe Asp Lys Thr Asp Gly
145                 150                 155                 160

Ala Leu Ser Ser Phe Asp Ile Lys Asp Lys Trp Ala Pro Ala Phe Gln
                165                 170                 175

Val Gly Leu Arg Tyr Asp Leu Gly Asn Ser Trp Met Leu Asn Ser Asp
                180                 185                 190

Val Arg Tyr Ile Pro Phe Lys Thr Asp Val Thr Gly Thr Leu Gly Pro
            195                 200                 205

Val Pro Val Ser Thr Lys Ile Glu Val Asp Pro Phe Ile Leu Ser Leu
        210                 215                 220

Gly Ala Ser Tyr Val Phe
225                 230

<210> SEQ ID NO 5
<211> LENGTH: 230
<212> TYPE: PRT
<213> ORGANISM: Artificial Sequence
<220> FEATURE:
<223> OTHER INFORMATION: ALK L

<400> SEQUENCE: 5

Val Ser Phe Ser Asn Tyr Lys Val Ile Ala Met Pro Val Leu Val Ala
1               5                   10                  15
```

```
Asn Phe Val Leu Gly Ala Ala Thr Ala Trp Ala Asn Glu Asn Tyr Pro
            20                  25                  30

Ala Lys Ser Ala Gly Tyr Asn Gln Gly Asp Trp Val Ala Ser Phe Asn
        35                  40                  45

Phe Ser Lys Val Tyr Val Gly Glu Glu Leu Gly Asp Leu Asn Val Gly
    50                  55                  60

Gly Gly Ala Leu Pro Asn Ala Asp Val Ser Ile Gly Asn Asp Thr Thr
65                  70                  75                  80

Leu Thr Phe Asp Ile Ala Tyr Phe Val Ser Asn Ile Ala Val Asp
                85                  90                  95

Phe Phe Val Gly Val Pro Ala Arg Ala Lys Phe Gln Gly Glu Lys Ser
                100                 105                 110

Ile Ser Ser Leu Gly Arg Val Ser Glu Val Asp Tyr Gly Pro Ala Ile
            115                 120                 125

Leu Ser Leu Gln Tyr His Tyr Asp Ser Phe Glu Arg Leu Tyr Pro Tyr
        130                 135                 140

Val Gly Val Gly Val Gly Arg Val Leu Phe Phe Asp Lys Thr Asp Gly
145                 150                 155                 160

Ala Leu Ser Ser Phe Asp Ile Lys Asp Lys Trp Ala Pro Ala Phe Gln
                165                 170                 175

Val Gly Leu Arg Tyr Asp Leu Gly Asn Ser Trp Met Leu Asn Ser Asp
            180                 185                 190

Val Arg Tyr Ile Pro Phe Lys Thr Asp Val Thr Gly Thr Leu Gly Pro
        195                 200                 205

Val Pro Val Ser Thr Lys Ile Glu Val Asp Pro Phe Ile Leu Ser Leu
    210                 215                 220

Gly Ala Ser Tyr Val Phe
225                 230

<210> SEQ ID NO 6
<211> LENGTH: 446
<212> TYPE: PRT
<213> ORGANISM: Artificial Sequence
<220> FEATURE:
<223> OTHER INFORMATION: FADL

<400> SEQUENCE: 6

Met Ser Gln Lys Thr Leu Phe Thr Lys Ser Ala Leu Ala Val Ala Val
1               5                   10                  15

Ala Leu Ile Ser Thr Gln Ala Trp Ser Ala Gly Phe Gln Leu Asn Glu
            20                  25                  30

Phe Ser Ser Ser Gly Leu Gly Arg Ala Tyr Ser Gly Glu Gly Ala Ile
        35                  40                  45

Ala Asp Asp Ala Gly Asn Val Ser Arg Asn Pro Ala Leu Ile Thr Met
    50                  55                  60

Phe Asp Arg Pro Thr Phe Ser Ala Gly Ala Val Tyr Ile Asp Pro Asp
65                  70                  75                  80

Val Asn Ile Ser Gly Thr Ser Pro Ser Gly Arg Ser Leu Lys Ala Asp
                85                  90                  95

Asn Ile Ala Pro Thr Ala Trp Val Pro Asn Met His Phe Val Ala Pro
                100                 105                 110

Ile Asn Asp Gln Phe Gly Trp Gly Ala Ser Ile Thr Ser Asn Tyr Gly
            115                 120                 125

Leu Ala Thr Glu Phe Asn Asp Thr Tyr Ala Gly Gly Ser Val Gly Gly
        130                 135                 140
```

Thr Thr Asp Leu Glu Thr Met Asn Leu Asn Leu Ser Gly Ala Tyr Arg
145                 150                 155                 160

Leu Asn Asn Ala Trp Ser Phe Gly Leu Gly Phe Asn Ala Val Tyr Ala
            165                 170                 175

Arg Ala Lys Ile Glu Arg Phe Ala Gly Asp Leu Gly Gln Leu Val Ala
            180                 185                 190

Gly Gln Ile Met Gln Ser Pro Ala Gly Gln Thr Gln Gln Gly Gln Ala
            195                 200                 205

Leu Ala Ala Thr Ala Asn Gly Ile Asp Ser Asn Thr Lys Ile Ala His
210                 215                 220

Leu Asn Gly Asn Gln Trp Gly Phe Gly Trp Asn Ala Gly Ile Leu Tyr
225                 230                 235                 240

Glu Leu Asp Lys Asn Asn Arg Tyr Ala Leu Thr Tyr Arg Ser Glu Val
            245                 250                 255

Lys Ile Asp Phe Lys Gly Asn Tyr Ser Ser Asp Leu Asn Arg Ala Phe
            260                 265                 270

Asn Asn Tyr Gly Leu Pro Ile Pro Thr Ala Thr Gly Gly Ala Thr Gln
            275                 280                 285

Ser Gly Tyr Leu Thr Leu Asn Leu Pro Glu Met Trp Glu Val Ser Gly
            290                 295                 300

Tyr Asn Arg Val Asp Pro Gln Trp Ala Ile His Tyr Ser Leu Ala Tyr
305                 310                 315                 320

Thr Ser Trp Ser Gln Phe Gln Gln Leu Lys Ala Thr Ser Thr Ser Gly
            325                 330                 335

Asp Thr Leu Phe Gln Lys His Glu Gly Phe Lys Asp Ala Tyr Arg Ile
            340                 345                 350

Ala Leu Gly Thr Thr Tyr Tyr Tyr Asp Asp Asn Trp Thr Phe Arg Thr
            355                 360                 365

Gly Ile Ala Phe Asp Asp Ser Pro Val Pro Ala Gln Asn Arg Ser Ile
370                 375                 380

Ser Ile Pro Asp Gln Asp Arg Phe Trp Leu Ser Ala Gly Thr Thr Tyr
385                 390                 395                 400

Ala Phe Asn Lys Asp Ala Ser Val Asp Val Gly Val Ser Tyr Met His
            405                 410                 415

Gly Gln Ser Val Lys Ile Asn Glu Gly Pro Tyr Gln Phe Glu Ser Glu
            420                 425                 430

Gly Lys Ala Trp Leu Phe Gly Thr Asn Phe Asn Tyr Ala Phe
            435                 440                 445

<210> SEQ ID NO 7
<211> LENGTH: 7387
<212> TYPE: DNA
<213> ORGANISM: Artificial Sequence
<220> FEATURE:
<223> OTHER INFORMATION: vector pCDF-fadD_Ec-wes_Hche

<400> SEQUENCE: 7
cgggatctcg acgctctccc ttatgcgact cctgcgttta gggaaagagc atttgtcaga      60
atatttaagg gcgcctgtca ctttgcttga tatatgagaa ttatttaacc ttataaatga     120
gaaaaaagca acgcacttta ataagatac gttgcttttt cgattgatga acacctataa     180
ttaaactatt catctattat ttgattttt tgtatatac aatatttcta gtttgttaaa     240
gagaattaag aaaataaatc tcgaaaataa taagggaaa atcagttttt gatatcaaaa     300
ttatacatgt caacgataat acaaaatata atacaaacta agatgttta tcagtattta     360

```
ttatgcattt agaataccttt ttgtgtcgcc cttattcgac tccctataga agttcctatt      420
ctctagaaag tataggaact tcccttcatt ttggatccaa ttgtgagcgg ataacaatta      480
cgagcttcat gcacagtgat cgacgctgtt gacaattaat catcggctcg tataatgtgt      540
ggatgtggaa ttgtgagcgc tcacaattcc acaacggttt ccctctagaa ataattttgt      600
ttaacaggag gtaaaacata tgttaacggc atgtatatca tttggggttg cgatgacgac      660
gaacacgcat tttagaggtg aagaattgaa gaaggtttgg cttaaccgtt atcccgcgga      720
cgttccgacg gagatcaacc ctgaccgtta tcaatctctg gtagatatgt tgagcagtc      780 ggtcgcgcgc tacgccgatc aacctgcgtt tgtgaatatg ggggaggtaa tgaccttccg      840
caagctggaa gaacgcagtc gcgcgtttgc cgcttatttg caacaagggt tggggctgaa      900
gaaaggcgat cgcgttgcgt tgatgatgcc taatttattg caatatccgg tggcgctgtt      960
tggcattttg cgtgccggga tgatcgtcgt aaacgttaac ccgttgtata ccccgcgtga     1020
gcttgagcat cagcttaacg atagcggcgc atcggcgatt gttatcgtgt ctaactttgc     1080
tcacacactg gaaaaagtgg ttgataaaac cgccgttcag cacgtaattc tgacccgtat     1140
gggcgatcag ctatctacgg caaaaggcac ggtagtcaat ttcgttgtta aatacatcaa     1200
gcgtttggtg ccgaaatacc atctgccaga tgccatttca tttcgtagcg cactgcataa     1260
cggctaccgg atgcagtacg tcaaacccga actggtgccg gaagatttag cttttctgca     1320
atacaccggc ggcaccactg gtgtggcgaa aggcgcgatg ctgactcacc gcaatatgct     1380
ggcgaacctg gaacaggtta acgcgaccta tggtccgctg ttgcatccgg gcaaagagct     1440
ggtggtgacg gcgctgccgc tgtatcacat ttttgccctg accattaact gcctgctgtt     1500
tatcgaactg ggtgggcaga acctgcttat cactaacccg cgcgatattc cagggttggt     1560
aaaagagtta gcgaaatatc cgtttaccgc tatcacgggc gttaacacct tgttcaatgc     1620
gttgctgaac aataaagagt tccagcagct ggatttctcc agtctgcatc tttccgcagg     1680
cggtgggatg ccagtgcagc aagtggtggc agagcgttgg gtgaaactga ccggacagta     1740
tctgctggaa ggctatgcc ttaccgagtg tgcgccgctg gtcagcgtta acccatatga     1800
tattgattat catagtggta gcatcggttt gccggtgccg tcgacggaag ccaaactggt     1860
ggatgatgat gataatgaag taccaccagg tcaaccgggt gagctttgtg tcaaaggacc     1920
gcaggtgatg ctgggttact ggcagcgtcc cgatgctacc gatgaaatca tcaaaaatgg     1980
ctggttacac accggcgaca tcgcggtaat ggatgaagaa ggattcctgc gcattgtcga     2040
tcgtaaaaaa gacatgattc tggtttccgg ttttaacgtc tatcccaacg agattgaaga     2100
tgtcgtcatg cagcatcctg gcgtacagga agtcgcggct gttggcgtac cttccggctc     2160
cagtggtgaa gcggtgaaaa tcttcgtagt gaaaaaagat ccatcgctta ccgaagagtc     2220
actggtgact ttttgccgcc gtcagctcac gggatacaaa gtaccgaagc tggtggagtt     2280
tcgtgatgag ttaccgaaat ctaacgtcgg aaaaattttg cgacgagaat acgtgacga     2340 agcgcgcggc aaagtggaca taaagcctg agcgaattcg gatccatgca cagtgaaatc     2400
atgaaaaatt tatttgcttt gtgagcggat aacaattata atagcatgct ggtcagtatt     2460
gagcgatgca tgcacggttt ccctctagaa ataattttgt ttaactttta ggaggtaaaa     2520
accatgggta gctctcacca tcatcatcat cacagctctg gcctggttcc gcgcggttcc     2580
cacatgacgc cgctgagccc ggtcgatcaa atctttctgt ggctggagaa gcgtcagcag     2640
ccgatgcacg tcggtggctt gcacattttc agcttccctg atgacgcaga cgcgaagtat     2700
```

```
atgaccgagc tggcgcagca actgcgtgca tacgcgacgc cgcaggcacc attcaaccgt    2760
cgcctgcgtc agcgctgggg ccgttactat tgggacaccg atgctcagtt cgacctggag    2820
catcattttc gtcacgaagc gctgccgaaa ccgggtcgca ttcgcgaact gttggcccac    2880
gttagcgcgg agcattctaa tctgatggat cgtgaacgtc cgatgtggga gtgccatctg    2940
atcgaaggca tccgtggtcg ccgtttcgcg gtttactaca aggcgcatca ctgtatgctg    3000
gacggtgtag ccgccatgcg tatgtgcgtg aaatcctaca gctttgatcc gaccgcaacg    3060
gagatgccgc cgatttgggc tatcagcaaa gacgttaccc cggctcgtga aactcaagca    3120
ccggcagcgg gtgacctggt gcactccctg tcccagctgg ttgagggtgc cggtcgtcaa    3180
ctggcgaccg tcccgaccct gattcgtgag ctggcaaaa acttgctgaa ggcgcgtgac    3240
gactctgacg cgggtctgat ttttcgcgct ccgccaagca ttctgaacca acgcatcacc    3300
ggtagccgcc gttttgcggc gcagagctac gcgttggaac gctttaaggc gatcggtaag    3360
gcattccagg ctacggttaa cgatgtggtg ctggcggtgt gcggttccgc actgcgtaac    3420
tatttgctga gccgccaagc cctgccggat caaccgctga ttgcaatggc ccctatgagc    3480
atccgtcagg acgatagcga cagcggcaat cagatcgcga tgatcctggc gaatctgggc    3540
acccacatcg cggacccggt ccgtcgtttg gaactgacga agcaagcgc tcgcgagagc    3600 aaagagcgct tccgtcagat gacgccggaa gaggcagtga actataccgc gctgaccctg    3660
gccccgagcg gtctgaatct gctgacgggt ttggccccga atggcaggc cttcaatgtc    3720 gtgattagca acgttccagg cccgaataag ccgctgtact ggaacggtgc gcgcctggaa    3780
ggcatgtatc cggtttctat tcctgtcgat tatgcggcat tgaatatcac tctggttagc    3840
taccgtgatc aactggaatt tggtttcacc gcatgtcgcc gtaccctgcc gtcgatgcaa    3900
cgtctgttgg attacattga gcaaggcatt gccgagctgg agaaagcggc tggcgtgtaa    3960
ctcgagatcg aatgagcaat aactagcata accccttggg gcctctaaac gggtcttgag    4020
gctcgagtct ggtaaagaaa ccgctgctgc gaaatttgaa cgccagcaca tggactcgtc    4080
tactagcgca gcttaattaa cctaggctgc tgccaccgct gagcaataac tagcataacc    4140
ccttggggcc tctaaacggg tcttgagggg ttttttgctg aaacctcagg catttgagaa    4200
gcacacggtc acactgcttc cggtagtcaa taaaccggta aaccagcaat agacataagc    4260
ggctatttaa cgaccctgcc ctgaaccgac gaccgggtca tcgtggccgg atcttgcggc    4320
ccctcggctt gaacgaattg ttagacatta tttgccgact accttggtga tctcgccttt    4380
cacgtagtgg acaaattctt ccaactgatc tgcgcgcgag gccaagcgat cttcttcttg    4440
tccaagataa gcctgtctag cttcaagtat gacgggctga tactgggccg gcaggcgctc    4500
cattgcccag tcggcagcga catccttcgg cgcgattttg ccggttactg cgctgtacca    4560
aatgcgggac aacgtaagca ctacatttcg ctcatcgcca gcccagtcgg gcggcgagtt    4620
ccatagcgtt aaggtttcat ttagcgcctc aaatagatcc tgttcaggaa ccggatcaaa    4680
gagttcctcc gccgctggac ctaccaaggc aacgctatgt tctcttgctt ttgtcagcaa    4740
gatagccaga tcaatgtcga tcgtggctgg ctcgaagata cctgcaagaa tgtcattgcg    4800
ctgccattct ccaaattgca gttcgcgctt agctggataa cgccacgaa tgatgtcgtc    4860 gtgcacaaca atggtgactt ctacagcgcg gagaatctcg ctctctccag gggaagccga    4920
agtttccaaa aggtcgttga tcaaagctcg ccgcgttgtt tcatcaagcc ttacggtcac    4980
cgtaaccagc aaatcaatat cactgtgtgg cttcaggccg ccatccactg cggagccgta    5040
caaatgtacg gccagcaacg tcggttcgag atggcgctcg atgacgccaa ctacctctga    5100
```

```
tagttgagtc gatacttcgg cgatcaccgc ttccctcata ctcttccttt ttcaatatta    5160
ttgaagcatt tatcagggtt attgtctcat gagcggatac atatttgaat gtatttagaa    5220
aaataaacaa atagctagct cactcggtcg ctacgctccg ggcgtgagac tgcggcgggc    5280
gctgcggaca catacaaagt tacccacaga ttccgtggat aagcagggga ctaacatgtg    5340
aggcaaaaca gcagggccgc gccggtggcg ttttccata ggctccgccc tcctgccaga     5400
gttcacataa acagacgctt ttccggtgca tctgtgggag ccgtgaggct caaccatgaa    5460
tctgacagta cgggcgaaac ccgacaggac ttaaagatcc ccaccgtttc cggcgggtcg    5520
ctccctcttg cgctctcctg ttccgaccct gccgtttacc ggatacctgt tccgcctttc    5580
tcccttacgg gaagtgtggc gctttctcat agctcacaca ctggtatctc ggctcggtgt    5640
aggtcgttcg ctccaagctg ggctgtaagc aagaactccc cgttcagccc gactgctgcg    5700
ccttatccgg taactgttca cttgagtcca acccggaaaa gcacggtaaa acgccactgg    5760
cagcagccat tggtaactgg gagttcgcag aggatttgtt tagctaaaca cgcggttgct    5820
cttgaagtgt gcgccaaagt ccggctacac tggaaggaca gatttggttg ctgtgctctg    5880
cgaaagccag ttaccacggt taagcagttc cccaactgac ttaaccttcg atcaaaccac    5940
ctccccaggt ggtttttcg tttacagggc aaaagattac gcgcagaaaa aaggatctc     6000
aagaagatcc tttgatcttt tctactgaac cgctctagat ttcagtgcaa tttatctctt    6060
caaatgtagc acctgaagtc agccccatac gatataagtt gtaattctca tgttagtcat    6120
gccccgcgcc caccggaagg agctgactgg gttgaaggct ctcaagggca tcggtcgaga    6180
tcccggtgcc taatgagtga gctaacttac attaattgcg ttgcgctcac tgcccgcttt    6240
ccagtcggga aacctgtcgt gccagctgca ttaatgaatc ggccaacgcg cggggagagg    6300
cggtttgcgt attgggcgcc agggtggttt tcttttcac cagtgagacg ggcaacagct     6360
gattgcccct taccgcctgg ccctgagaga gttgcagcaa gcggtccacg ctggtttgcc    6420
ccagcaggcg aaaatcctgt ttgatggtgg ttaacggcgg gatataacat gagctgtctt    6480
cggtatcgtc gtatcccact accgagatgt ccgcaccaac gcgcagcccg gactcggtaa    6540
tggcgcgcat tgcgcccagc gccatctgat cgttggcaac cagcatcgca gtgggaacga    6600
tgccctcatt cagcatttgc atggtttgtt gaaaaccgga catggcactc cagtcgcctt    6660
cccgttccgc tatcggctga atttgattgc gagtgagata tttatgccag ccagccagac    6720
gcagacgcgc cgagacagaa cttaatgggc ccgctaacag cgcgatttgc tggtgaccca    6780
atgcgaccag atgctccacg cccagtcgcg taccgtcttc atgggagaaa ataatactgt    6840
tgatgggtgt ctggtcagag acatcaagaa ataacgccgg aacattagtg caggcagctt    6900
ccacagcaat ggcatcctgg tcatccagcg gatagttaat gatcagccca ctgacgcgtt    6960
gcgcgagaag attgtgcacc gccgctttac aggcttcgac gccgcttcgt tctaccatcg    7020
acaccaccac gctggcaccc agttgatcgg cgcgagattt aatcgccgcg acaatttgcg    7080
acggcgcgtg cagggccaga ctggaggtgg caacgccaat cagcaacgac tgtttgcccg    7140
ccagttgttg tgccacgcgg ttgggaatgt aattcagctc cgccatcgcc gcttccactt    7200
tttcccgcgt tttcgcagaa acgtggctgg cctggttcac cacgcgggaa acggtctgat    7260
aagagacacc ggcatactct gcgacatcgt ataacgttac tggtttcaca ttcaccaccc    7320
tgaattgact ctcttccggg cgctatcatg ccataccgcg aaaggttttg cgccattcga    7380
tggtgtc                                                              7387
```

BIOTECHNOLOGICAL PRODUCTION OF OMEGA-FUNCTIONALISED CARBOXYLIC ACIDS AND ESTERS THEREOF

BACKGROUND OF THE INVENTION

Field of the Invention

The present invention relates to a biotechnological method for producing ω-functionalized carboxylic acid esters. In particular, the method may use alkane as a starting material and a genetically modified cell to convert the alkane to the corresponding ω-functionalized carboxylic acid ester.

Discussion of the Background

ω-functionalized carboxylic acids and the corresponding esters including ω-aminocarboxylic acids and their corresponding lactames, such as ω-aminolauric acid, ω-aminoundecanoic acid, laurolactame and the like, are important monomers for production of high-performance polyamides. Some of the existing chemical technology that has been used to produce these monomers from petrochemical or renewable feedstocks include:

i) The production of ω-aminolauric acid from lauric acid methyl ester, a biodiesel fraction prepared from palm kernel or coconut oil
ii) The production of ω-aminoundecanoic acid from ricinoleic acid, prepared from castor oil
iii) The production of laurolactame from butadiene While all these three methods of production remain competitive, their competitiveness at a given location and point in time is dependent on a number of factors, including the costs of raw materials and energy costs to run the methods.

There are several biotechnological means of producing ω-functionalized carboxylic acids and/or esters thereof that are known in the art. For example, genetically modified cells that are capable of producing ω-functionalized carboxylic acids from carboxylic acid used as a substrate has been previously described at least in WO2009077461 and EP2322598. A very similar procedure is described in WO2011008232 using *Candida* cells where the β-oxidation pathway is blocked in the cells, and ω-functionalized carboxylic acids were formed from fatty acid used as a substrate. These methods have the disadvantage of using fatty acids as the starting material. This is because, the fatty acids and derivatives thereof used are mainly obtained exclusively from plant and animal oils or fats. Animal fats as raw materials still meet little client acceptance and plant oils which contain short- and middle-length fatty acids are either difficult to obtain or are produced only in tropical regions (result of destruction of rainforest). Further, particular plant and animal oil or fat raw materials have specific, but defined fatty acid profiles resulting in coupled production.

WO2013024114 discloses a method of producing ω-functionalized carboxylic acids and/or esters thereof from simple carbon sources such as (glucose, saccharose, arabinose, xylose, lactose, fructose, maltose, molasses, starch, cellulose and hemicellulose, but also glycerin or very simple organic molecules such as $CO_2$, CO or synthesis gas). These simple sugars especially glucose are usually more expensive to obtain. The method of producing ω-functionalized carboxylic acids and/or esters thereof from simple carbon sources may also be considered complicated as the cells used in this method have to be genetically modified to increase production of carboxylic acids from these simple carbon sources first. This thus increases the cost of production.

Therefore, there is a need in the art for a method to produce ω-functionalized carboxylic acids esters from another source of raw material that enables the production to be efficient and effective.

DESCRIPTION OF THE INVENTION

The present invention attempts to solve the problems above by providing at least one genetically modified microbial cell that is capable of producing at least one ω-functionalized carboxylic acid ester from at least one alkane. The ω-functionalized carboxylic acid ester may be selected from the group consisting of ω-hydroxy, ω-oxo, ω-carboxy and ω-amino carboxylic acid esters. The use of these genetically modified cells in a method to produce ω-functionalized carboxylic acid esters may add flexibility to the production of these compounds by enabling the use of a readily available alternative petrochemical raw material for its production. Also, the use of whole-cell biocatalysts capable of integrating the entire means of converting alkanes to fatty acid esters and their corresponding ω-functionalized derivatives within them, makes the process of conversion simpler as only a small number of process steps are involved in the conversion. The reliance of fatty acids and simple carbon sources as the carbon substrate is also eliminated.

According to a first aspect of the present invention, there is provided a microbial cell for producing at least one ω-functionalized carboxylic acid ester from at least one alkane, wherein the cell comprises a genetic modification to increase the expression relative to the wild type cell of (i) Enzyme $E_1$ capable of converting the alkane to the corresponding 1-alkanol;
(ii) Enzyme $E_2$ capable of converting the 1-alkanol of (i) to the corresponding 1-alkanal;
(iii) Enzyme $E_3$ capable of converting the 1-alkanal of (ii) to the corresponding alkanoic acid;
(iv) Enzyme $E_4$ capable of converting the alkanoic acid of (iii) to the corresponding alkanoic acid ester; and
(v) Enzyme $E_5$ capable of converting the alkanoic acid ester of (iv) to the corresponding ω-hydroxy-alkanoic acid ester.

The microbial cell according to any aspect of the present invention refers to a cell that has no previous/former modification to increase the formation of carboxylic acid or carboxylate ester from at least one simple carbon source. The term "simple carbon source" is understood to mean carbon sources wherein in the carbon skeleton at least one C—C bond has been broken. In particular, the simple carbon source may be at least one carbohydrate such as for example glucose, saccharose, arabinose, xylose, lactose, fructose, maltose, molasses, starch, cellulose and hemicellulose, but carbon sources may also include glycerin or very simple organic molecules such as $CO_2$, CO or synthesis gas. More in particular, the microbial cell according to any aspect of the present invention may not be genetically modified to increase the expression relative to the wild type cell of at least one of the following enzymes:

$E_{20}$ Acyl-ACP thioesterase, of EC 3.1.2.14 or EC 3.1.2.22,
$E_{21}$ Acyl-CoA thioesterase, of EC 3.1.2.2, EC 3.1.2.18, EC 3.1.2.19, EC 3.1.2.20 or EC 3.1.2.22,
$E_{22}$ Acyl-CoA:ACP transacylase,
$E_{23}$ Polyketide synthase, which catalyses a reaction which is involved in the synthesis of carboxylic acids and carboxylate esters, and
$E_{24}$ Hexanoic acid synthase.

In one example, the cell according to any aspect of the present invention may comprise a further genetic modification to increase the expression relative to the wild type cell of
- (vi) Enzyme $E_6$ capable of converting the ω-hydroxyalkanoic acid ester of (v) to the corresponding ω-oxo alkanoic acid ester; and
- (vii) Enzyme $E_7$ capable of converting the ω-oxo alkanoic acid ester of (vi) to the corresponding ω-amino alkanoic acid ester.

In another example, the cell according to any aspect of the present invention may comprise a further genetic modification to increase the expression relative to the wild type cell of
- (vi) Enzyme $E_6$ capable of converting ω-hydroxy-alkanoic acid ester of (v) to the corresponding ω-oxo alkanoic acid ester;
- (vii) Enzyme $E_{13}$ capable of converting the ω-oxo alkanoic acid ester of (vi) to the corresponding ω-carboxy alkanoic acid ester, and
- (viii) Enzyme $E_{14}$ capable of converting the ω-carboxy alkanoic acid ester of (vi) to the corresponding ω-carboxy alkanoic acid diester.

The cells according to any aspect of the present invention may be used to produce ω-functionalized carboxylic acid ester from all alkanes with high space-time yield, high carbon yield and high concentration in the culture supernatant. As a result of these advantages, an efficient workup is facilitated.

The phrase "wild type" as used herein in conjunction with a cell or microorganism may denote a cell with a genome make-up that is in a form as seen naturally in the wild. The term may be applicable for both the whole cell and for individual genes. The term 'wild type' may thus also include cells which have been genetically modified in other aspects (i.e. with regard to one or more genes) but not in relation to the genes of interest. The term "wild type" therefore does not include such cells where the gene sequences of the specific genes of interest have been altered at least partially by man using recombinant methods. A wild type cell according to any aspect of the present invention thus refers to a cell that has no genetic mutation with respect to the whole genome and/or a particular gene. Therefore, in one example, a wild type cell with respect to enzyme $E_1$ may refer to a cell that has the natural/non-altered expression of the enzyme $E_1$ in the cell. The wild type cell with respect to enzyme $E_2$, $E_3$, $E_4$, $E_5$, $E_6$, $E_7$, $E_8$, $E_9$, $E_{10}$, $E_{11}$, $E_{12}$, $E_{13}$, $E_{14}$, $E_{15}$, etc. may be interpreted the same way and may refer to a cell that has the natural/non-altered expression of the enzyme $E_2$, $E_3$, $E_4$, $E_5$, $E_6$, $E_7$, $E_8$, $E_9$, $E_{10}$, $E_{11}$, $E_{12}$, $E_{13}$, $E_{14}$, $E_{15}$, etc. respectively in the cell.

Any of the enzymes used according to any aspect of the present invention, may be an isolated enzyme. In particular, the enzymes used according to any aspect of the present invention may be used in an active state and in the presence of all cofactors, substrates, auxiliary and/or activating polypeptides or factors essential for its activity. The term "isolated", as used herein, means that the enzyme of interest is enriched compared to the cell in which it occurs naturally. The enzyme may be enriched by SDS polyacrylamide electrophoresis and/or activity assays. For example, the enzyme of interest may constitute more than 5, 10, 20, 50, 75, 80, 85, 90, 95 or 99 percent of all the polypeptides present in the preparation as judged by visual inspection of a polyacrylamide gel following staining with Coomassie blue dye.

The enzyme used according to any aspect of the present invention may be recombinant. The term "recombinant" as used herein, refers to a molecule or is encoded by such a molecule, particularly a polypeptide or nucleic acid that, as such, does not occur naturally but is the result of genetic engineering or refers to a cell that comprises a recombinant molecule. For example, a nucleic acid molecule is recombinant if it comprises a promoter functionally linked to a sequence encoding a catalytically active polypeptide and the promoter has been engineered such that the catalytically active polypeptide is overexpressed relative to the level of the polypeptide in the corresponding wild type cell that comprises the original unaltered nucleic acid molecule.

A skilled person would be able to use any method known in the art to genetically modify a cell or microorganism. According to any aspect of the present invention, the genetically modified cell may be genetically modified so that in a defined time interval, within 2 hours, in particular within 8 hours or 24 hours, it forms at least once or twice, especially at least 10 times, at least 100 times, at least 1000 times or at least 10000 times more ω-functionalized carboxylic acid ester than the wild-type cell. The increase in product formation can be determined for example by cultivating the cell according to any aspect of the present invention and the wild-type cell each separately under the same conditions (same cell density, same nutrient medium, same culture conditions) for a specified time interval in a suitable nutrient medium and then determining the amount of target product (ω-functionalized carboxylic acid ester) in the nutrient medium.

The genetically modified cell or microorganism may be genetically different from the wild type cell or microorganism. The genetic difference between the genetically modified microorganism according to any aspect of the present invention and the wild type microorganism may be in the presence of a complete gene, amino acid, nucleotide etc. in the genetically modified microorganism that may be absent in the wild type microorganism. In one example, the genetically modified microorganism according to any aspect of the present invention may comprise enzymes that enable the microorganism to produce more 1-alkanols, 1-alkanals, alkanoic acids, alkanoic acid esters, omega-hydroxy alkanoic acid esters etc. compared to the wild type cells. The wild type microorganism relative to the genetically modified microorganism of the present invention may have none or no detectable activity of the enzymes that enable the genetically modified microorganism to produce 1-alkanols, 1-alkanals, alkanoic acids, alkanoic acid esters, omega-hydroxy alkanoic acid esters, etc. As used herein, the term 'genetically modified microorganism' may be used interchangeably with the term 'genetically modified cell'. The genetic modification according to any aspect of the present invention is carried out on the cell of the microorganism.

The cells according to any aspect of the present invention are genetically transformed according to any method known in the art. In particular, the cells may be produced according to the method disclosed in WO2013024114.

The phrase 'the genetically modified cell has an increased activity, in comparison with its wild type, in enzymes' as used herein refers to the activity of the respective enzyme that is increased by a factor of at least 2, in particular of at least 10, more in particular of at least 100, yet more in particular of at least 1000 and even more in particular of at least 10000.

The phrase "increased activity of an enzyme", as used herein is to be understood as increased intracellular activity. Basically, an increase in enzymatic activity can be achieved by increasing the copy number of the gene sequence or gene sequences that code for the enzyme, using a strong promoter or employing a gene or allele that codes for a corresponding enzyme with increased activity, altering the codon utilization of the gene, increasing the half-life of the mRNA or of the enzyme in various ways, modifying the regulation of the expression of the gene and optionally by combining these measures. Genetically modified cells used according to any aspect of the present invention are for example produced by transformation, transduction, conjugation or a combination of these methods with a vector that contains the desired gene, an allele of this gene or parts thereof and a vector that makes expression of the gene possible. Heterologous expression is in particular achieved by integration of the gene or of the alleles in the chromosome of the cell or an extrachromosomally replicating vector In the same context, the phrase "decreased activity of an enzyme $E_x$" used with reference to any aspect of the present invention may be understood as meaning an activity decreased by a factor of at least 0.5, particularly of at least 0.1, more particularly of at least 0.01, even more particularly of at least 0.001 and most particularly of at least 0.0001. The phrase "decreased activity" also comprises no detectable activity ("activity of zero"). The decrease in the activity of a certain enzyme can be effected, for example, by selective mutation or by other measures known to the person skilled in the art for decreasing the activity of a certain enzyme. In particular, the person skilled in the art finds instructions for the modification and decrease of protein expression and concomitant lowering of enzyme activity by means of interrupting specific genes, for example at least in Dubeau et al. 2009, Singh & Röhm. 2008, Lee et al., 2009 and the like. The decrease in the enzymatic activity in a cell according to any aspect of the present invention may be achieved by modification of a gene comprising one of the nucleic acid sequences, wherein the modification is selected from the group comprising, consisting of, insertion of foreign DNA in the gene, deletion of at least parts of the gene, point mutations in the gene sequence, RNA interference (siRNA), antisense RNA or modification (insertion, deletion or point mutations) of regulatory sequences, such as, for example, promoters and terminators or of ribosome binding sites, which flank the gene.

Foreign DNA is to be understood in this connection as meaning any DNA sequence which is "foreign" to the gene (and not to the organism), i.e. endogenous DNA sequences can also function in this connection as "foreign DNA". In this connection, it is particularly preferred that the gene is interrupted by insertion of a selection marker gene, thus the foreign DNA is a selection marker gene, wherein preferably the insertion was effected by homologous recombination in the gene locus.

The expression of the enzymes and genes mentioned above and all mentioned below is determinable by means of 1- and 2-dimensional protein gel separation followed by optical identification of the protein concentration in the gel with appropriate evaluation software.

If the increasing of an enzyme activity is based exclusively on increasing the expression of the corresponding gene, then the quantification of the increasing of the enzyme activity can be simply determined by a comparison of the 1- or 2-dimensional protein separations between wild type and genetically modified cell. A common method for the preparation of the protein gels with bacteria and for identification of the proteins is the procedure described by Hermann et al. (Electrophoresis, 22: 1712-23 (2001). The protein concentration can also be analysed by Western blot hybridization with an antibody specific for the protein to be determined (Sambrook et al., Molecular Cloning: a laboratory manual, 2nd Ed. Cold Spring Harbor Laboratory Press, Cold Spring Harbor, N.Y. USA, 1989) followed by optical evaluation with appropriate software for concentration determination (Lohaus and Meyer (1989) Biospektrum, 5: 32-39; Lottspeich (1999), Angewandte Chemie 111: 2630-2647). This method is also always an option when possible products of the reaction to be catalysed by the enzyme activity to be determined may be rapidly metabolized in the microorganism or else the activity in the wild type is itself too low for it to be possible adequately to determine the enzyme activity to be determined on the basis of the production formation.

In particular, the Enzyme $E_1$ may be selected from the group consisting of P450 alkane hydroxylases ($E_a$) and AlkB alkane hydroxylases ($E_b$) of EC 1.14.15.3;

the Enzyme $E_2$ may be selected from the group consisting of P450 alkane hydroxylases ($E_a$), AlkB alkane hydroxylases ($E_b$) of EC 1.14.15.3, alcohol oxidases ($E_c$) of EC 1.1.3.20 and alcohol dehydrogenases ($E_d$);

the Enzyme $E_3$ is selected from the group consisting of P450 alkane hydroxylases ($E_a$) of EC 1.14.15.3-, AlkB alkane hydroxylases ($E_b$) of EC 1.14.15.3, aldehyde dehydrogenases ($E_e$), bifunctional alcohol oxidases ($E_c$) of EC 1.1.3.20, bifunctional AlkJ alcohol dehydrogenases ($E_{di}$) and bifunctional alcohol dehydrogenases ($E_{dii}$) of EC 1.1.1.1 or EC 1.1.1.2, wherein $E_c$, $E_{di}$, and $E_{dii}$ are capable of oxidizing an 1-alkanol via an 1-alkanal directly to the corresponding alkanoic acid;

the Enzyme $E_4$ may be selected from the group consisting of wax-ester synthases ($E_f$) and alcohol O-acyl transferases ($E_g$);

the Enzyme $E_5$ may be selected from the group consisting of P450 alkane hydroxylases ($E_a$) and AlkB alkane hydroxylases ($E_b$) of EC 1.14.15.3;

the Enzyme $E_6$ may be selected from the group consisting of P450 alkane hydroxylases ($E_a$), AlkB alkane hydroxylases ($E_b$) of EC 1.14.15.3, alcohol oxidases ($E_c$) and alcohol dehydrogenases ($E_d$);

the Enzyme $E_7$ may be an ω-transaminase ($E_h$).

In one example, enzymes $E_1$, $E_2$, $E_3$ and $E_5$ may each be different enzymes that may be capable of carrying out their activity. For example, $E_1$ may be AlkB alkane hydroxylases ($E_b$), $E_2$ may be alcohol oxidase ($E_c$), $E_3$ may be bifunctional AlkJ alcohol dehydrogenase, and $E_5$ may be AlkB alkane hydroxylase ($E_b$). In another example, $E_1$ may be P450 alkane hydroxylase ($E_a$), $E_2$ may be alcohol dehydrogenase ($E_c$), $E_3$ may be aldehyde dehydrogenase ($E_e$), and $E_5$ may P450 alkane hydroxylase. In particular, any combination of enzymes of $E_1$, $E_2$, $E_3$ and $E_5$ may be used to carry out their specific functions. In a further example, $E_1$, $E_2$, $E_3$ and $E_5$ may be the same enzyme. In this example, $E_1$, $E_2$, $E_3$ and $E_5$ may be selected from the group consisting of P450 alkane hydroxylases ($E_a$) and AlkB alkane hydroxylases ($E_b$). In one example, $E_1$, $E_2$, $E_3$ and $E_5$ may be P450 alkane hydroxylases ($E_a$). In this example, the cell according to any aspect of the present invention comprises an increased expression relative to the wild type cell of P450 alkane hydroxylases ($E_a$) that satisfies the function of enzymes $E_1$, $E_2$, $E_3$ and $E_5$. In another example, $E_1$, $E_2$, $E_3$ and $E_5$ may be AlkB alkane hydroxylase ($E_b$). In this example, the cell according to any aspect of the present invention comprises an increased expression relative to the wild type cell of AlkB alkane hydroxylase ($E_b$) that satisfies the function of enzymes $E_1$, $E_2$, $E_3$ and $E_5$.

The enzymes $E_a$ to $E_h$ may comprise a polypeptide sequence wherein up to 60%, preferably up to 25%, particularly up to 15%, in particular up to 10, 9, 8, 7, 6, 5, 4, 3, 2 or 1% of the amino acid residues are modified compared to the below reference sequences (accession numbers by deletion, insertion, substitution or a combination thereof and which still possess at least 50%, preferably 65%, particularly preferably 80%, in particular more than 90% of the activity of the protein with the corresponding, below reference sequence, wherein 100% activity of the reference protein is understood to mean the increasing of the activity of the cells used as a biocatalyst, i.e. the quantity of substance converted per unit time based on the cell quantity used (units per gram cell dry weight [U/g CDW]) in comparison to the activity of the biocatalyst in the absence of the reference protein.

Modifications of amino acid residues of a given polypeptide sequence which lead to no significant modifications of the properties and function of the given polypeptide are known to those skilled in the art. Thus for example many amino acids can often be exchanged for one another without problems; examples of such suitable amino acid substitutions are: Ala by Ser; Arg by Lys; Asn by Gln or His; Asp by Glu; Cys by Ser; Gln by Asn; Glu by Asp; Gly by Pro; His by Asn or Gln; Ile by Leu or Val; Leu by Met or Val; Lys by Arg or Gln or Glu; Met by Leu or Ile; Phe by Met or Leu or Tyr; Ser by Thr; Thr by Ser; Trp by Tyr; Tyr by Trp or Phe; Val by Ile or Leu. It is also known that modifications, particularly at the N- or C-terminus of a polypeptide in the form of for example amino acid insertions or deletions, often exert no significant influence on the function of the polypeptide.

The accession numbers stated in connection with the present invention mentioned throughout this specification correspond to the NCBI ProteinBank database entries with the date Jul. 26, 2011; as a rule, the version number of the entry is identified here by "numerals" such as for example "0.1".

All stated percentages (%) are, unless otherwise stated, mass percent.

According to any aspect of the present invention, the microbial cell may be selected from the species of bacteria from the group consisting of, Abiotrophia, Acaryochloris, Accumulibacter, Acetivibrio, Acetobacter, Acetohalobium, Acetonema, Achromobacter, Acidaminococcus, Acidimicrobium, Acidiphilium, Acidithiobacillus, Acidobacterium, Acidothermus, Acidovorax, Acinetobacter, Actinobacillus, Actinomyces, Actinosynnema, Aerococcus, Aeromicrobium, Aeromonas, Afipia, Aggregatibacter, Agrobacterium, Ahrensia, Akkermansia, Alcanivorax, Alicycliphilus, Alicyclobacillus, Aliivibrio, Alkalilimnicola, Alkaliphilus, Allochromatium, Alteromonadales, Alteromonas, Aminobacterium, Aminomonas, Ammonifex, Amycolatopsis, Amycolicicoccus, Anabaena, Anaerobaculum, Anaerococcus, Anaerofustis, Anaerolinea, Anaeromyxobacter, Anaerostipes, Anaerotruncus, Anaplasma, Anoxybacillus, Aquifex, Arcanobacterium, Arcobacter, Aromatoleum, Arthrobacter, Arthrospira, Asticcacaulis, Atopobium, Aurantimonas, Azoarcus, Azorhizobium, Azospirillum, Azotobacter, Bacillus, Bartonella, Basfia, Baumannia, Bdellovibrio, Beggiatoa, Beijerinckia, Bermanella, Beutenbergia, Bifidobacterium, Bilophila, Blastopirellula, Blautia, Blochmannia, Bordetella, Borrelia, Brachybacterium, Brachyspira, Bradyrhizobium, Brevibacillus, Brevibacterium, Brevundimonas, Brucella, Buchnera, Bulleidia, Burkholderia, Butyrivibrio, Caldalkalibacillus, Caldanaerobacter, Caldicellulosiruptor, Calditerrivibrio, Caminibacter, Campylobacter, Carboxydibrachium, Carboxydothermus, Cardiobacterium, Carnobacterium, Carsonella, Catenibacterium, Catenulispora, Catonella, Caulobacter, Cellulomonas, Cellvibrio, Centipeda, Chelativorans, Chloroflexus, Chromobacterium, Chromohalobacter, Chthoniobacter, Citreicella, Citrobacter, Citromicrobium, Clavibacter, Cloacamonas, Clostridium, Collinsella, Colwellia, Comamonas, Conexibacter, Congregibacter, Coprobacillus, Coprococcus, Coprothermobacter, Coraliomargarita, Coriobacterium, corrodens, Corynebacterium, Coxiella, Crocosphaera, Cronobacter, Cryptobacterium, Cupriavidus, Cyanobium, Cyanothece, Cylindrospermopsis, Dechloromonas, Deferribacter, Dehalococcoides, Dehalogenimonas, Deinococcus, Delftia, Denitrovibrio, Dermacoccus, Desmospora, Desulfarculus, Desulphateibacillum, Desulfitobacterium, Desulfobacca, Desulfobacterium, Desulfobulbus, Desulfococcus, Desulfohalobium, Desulfomicrobium, Desulfonatronospira, Desulforudis, Desulfotalea, Desulfotomaculum, Desulfovibrio, Desulfurispirillum, Desulfurobacterium, Desulfuromonas, Dethiobacter, Dethiosulfovibrio, Dialister, Dichelobacter, Dickeya, Dictyoglomus, Dietzia, Dinoroseobacter, Dorea, Edwardsiella, Ehrlichia, Eikenella, Elusimicrobium, Endoriftia, Enhydrobacter, Enterobacter, Enterococcus, Epulopiscium, Erwinia, Erysipelothrix, Erythrobacter, Escherichia, Ethanoligenens, Eubacterium, Eubacterium, Exiguobacterium, Faecalibacterium, Ferrimonas, Fervidobacterium, Fibrobacter, Finegoldia, Flexistipes, Francisella, Frankia, Fructobacillus, Fulvimarina, Fusobacterium, Gallibacterium, Gallionella, Gardnerella, Gemella, Gemmata, Gemmatimonas, Geobacillus, Geobacter, Geodermatophilus, Glaciecola, Gloeobacter, Glossina, Gluconacetobacter, Gordonia, Granulibacter, Granulicatella, Grimontia, Haemophilus, Hahella, Halanaerobiumns, Haliangium, Halomonas, Halorhodospira, Halothermothrix, Halothiobacillus, Hamiltonella, Helicobacter, Heliobacterium, Herbaspirillum, Herminiimonas, Herpetosiphon, Hippea, Hirschia, Histophilus, Hodgkinia, Hoeflea, Holdemania, Hydrogenivirga, Hydrogenobaculum, Hylemonella, Hyphomicrobium, Hyphomonas, Idiomarina, Ilyobacter, Intrasporangium, Isoptericola, Isosphaera, Janibacter, Janthinobacterium, Jonesia, Jonquetella, Kangiella, Ketogulonicigenium, Kineococcus, Kingella, Klebsiella, Kocuria, Koribacter, Kosmotoga, Kribbella, Ktedonobacter, Kytococcus, Labrenzia, Lactobacillus, Lactococcus, Laribacter, Lautropia, Lawsonia, Legionella, Leifsonia, Lentisphaera, Leptolyngbya, Leptospira, Leptothrix, Leptotrichia, Leuconostoc, Liberibacter, Limnobacter, Listeria, Loktanella, Lutiella, Lyngbya, Lysinibacillus, Macrococcus, Magnetococcus, Magnetospirillum, Mahella, Mannheimia, Maricaulis, Marinithermus, Marinobacter, Marinomonas, Mariprofundus, Maritimibacter, Marvinbryantia, Megasphaera, Meiothermus, Melissococcus, Mesorhizobium, Methylacidiphilum, Methylibium, Methylobacillus, Methylobacter, Methylobacterium, Methylococcus, Methylocystis, Methylomicrobium, Methylophaga, Methylophilales, Methylosinus, Methyloversatilis, Methylovorus, Microbacterium, Micrococcus, Microcoleus, Microcystis, Microlunatus, Micromonospora, Mitsuokella, Mobiluncus, Moorella, Moraxella, Moritella, Mycobacterium, Myxococcus, Nakamurella, Natranaerobius, Neisseria, Neorickettsia, Neptuniibacter, Nitratifractor, Nitratiruptor, Nitrobacter, Nitrococcus, Nitrosomonas, Nitrosospira, Nitrospira, Nocardia, Nocardioides, Nocardiopsis, Nodularia, Nostoc, Novosphingobium, Oceanibulbus, Oceanicaulis, Oceanicola, Oceanithermus, Oceanobacillus, Ochrobactrum, Octadecabacter, Odyssella, Oligotropha, Olsenella, Opitutus, Oribacterium, Orientia, Ornithinibacillus, Oscillatoria, Oscillochloris, Oxalobacter, Paenibacillus, Pantoea, Paracoccus, Parascardovia, Parasutterella, Parvibaculum, Par-

*vimonas, Parvularcula, Pasteurella, Pasteuria, Pectobacterium, Pediococcus, Pedosphaera, Pelagibaca, Pelagibacter, Pelobacter, Pelotomaculum, Peptoniphilus, Peptostreptococcus, Persephonella, Petrotoga, Phaeobacter, Phascolarctobacterium, Phenylobacterium, Photobacterium, Pirellula, Planctomyces, Planococcus, Plesiocystis, Polaromonas, Polaromonas, Polymorphum, Polynucleobacter, Poribacteria, Prochlorococcus, Propionibacterium, Proteus, Providencia, Pseudoalteromonas, Pseudoflavonifractor, Pseudomonas, Pseudonocardia, Pseudoramibacter, Pseudovibrio, Pseudoxanthomonas, Psychrobacter, Psychromonas, Puniceispirillum, Pusillimonas, Pyramidobacter, Rahnella, Ralstonia, Raphidiopsis, Regiella, Reinekea, Renibacterium, Rhizobium, Rhodobacter, Rhodococcus, Rhodoferax, Rhodomicrobium, Rhodopirellula, Rhodopseudomonas, Rhodospirillum, Rickettsia, Rickettsiella, Riesia, Roseburia, Roseibium, Roseiflexus, Roseobacter, Roseomonas, Roseovarius, Rothia, Rubrivivax, Rubrobacter, Ruegeria, Ruminococcus, Ruthia, Saccharomonospora, Saccharophagus, Saccharopolyspora, Sagittula, Salinispora, Salmonella, Sanguibacte, Scardovia, Sebaldella, Segniliparus, Selenomonas, Serratia, Shewanella, Shigella, Shuttleworthia, Sideroxydans, Silicibacter, Simonsiella, Sinorhizobium, Slackia, Sodalis, Solibacter, Solobacterium, Sorangium, Sphaerobacter, Sphingobium, Sphingomonas, Sphingopyxis, Spirochaeta, Sporosarcina, Stackebrandtia, Staphylococcus, Starkeya, Stenotrophomonas, Stigmatella, Streptobacillus, Streptococcus, Streptomyces, Streptosporangium, Subdoligranulum, subvibrioides, Succinatimonas, Sulfitobacter, Sulfobacillus, Sulfuricurvum, Sulfurihydrogenibium, Sulfurimonas, Sulfurospirillum, Sulfurovum, Sutterella, Symbiobacterium, Synechocystis, Syntrophobacter, Syntrophobotulus, Syntrophomonas, Syntrophothermus, Syntrophus, taiwanensis, Taylorella, Teredinibacter, Terriglobus, Thalassiobium, Thauera, Thermaerobacter, Thermanaerovibrio, Thermincola, Thermoanaerobacter, Thermoanaerobacterium, Thermobaculum, Thermobifida, Thermobispora, Thermocrinis, Thermodesulphateator, Thermodesulfobacterium, Thermodesulfobium, Thermodesulfovibrio, Thermomicrobium, Thermomonospora, Thermosediminibacter, Thermosinus, Thermosipho, Thermosynechococcus, Thermotoga, Thermovibrio, Thermus, Thioalkalimicrobium, Thioalkalivibrio, Thiobacillus, Thiomicrospira, Thiomonas, Tolumonas, Treponema, tribocorum, Trichodesmium, Tropheryma, Truepera, Tsukamurella, Turicibacter, Variovorax, Veillonella, Verminephrobacter, Verrucomicrobium, Verrucosispora, Vesicomyosocius, Vibrio, Vibrionales, Victivallis, Weissella, Wigglesworthia, Wolbachia, Wolinella, Xanthobacter, Xanthomonas, Xenorhabdus, Xylanimonas, Xylella, Yersinia, Zinderia* and *Zymomonas.*

In particular, the microbial cell may be from *E. coli, Pseudomonas* sp., *Pseudomonas fluorescens, Pseudomonas putida, Pseudomonas stutzeri, Acinetobacter* sp., *Burkholderia* sp., *Burkholderia thailandensis, Cyanobakterien, Klebsiella* sp., *Klebsiella oxytoca, Salmonella* sp., *Rhizobium* sp. and *Rhizobium meliloti, Bacillus* sp., *Bacillus subtilis, Clostridium* sp., *Corynebacterium* sp., *Corynebacterium glutamicum, Brevibacterium* sp., *Chlorella* sp. and *Nostoc* sp. More in particular, the microbial cell may be from *E. coli.*

Alkanes are saturated hydrocarbons that have various applications depending on the number of carbon atoms and on the structure of the alkane (i.e. branched, linear, cyclic etc.). Alkanes (technically, always acyclic or open-chain compounds) have the general chemical formula $C_nH_{2n+2}$. An alkane used according to any aspect of the present invention may comprise at least 6 C atoms.

In particular, the alkane used according to any aspect of the present invention may comprise 6-22, 6-20, 6-18, 6-17, 6-16, 6-15, 6-14, 6-13, 6-12, 6-11, 6-10, 8-20, 8-19, 8-18, 8-16, 8-15, 8-12, 8-10 carbon atoms (inclusive). The alkanes may be selected from the group consisting of hexane, heptane, octane, nonane, decane, undecane, dodecane, tridecane, tetradecane pentadecane, hexadecane, and icosane. In particular, the alkane used may be decane, undecane or dodecane.

Enzyme $E_1$

Enzyme $E_1$ may be capable of converting at least one alkane to the corresponding 1-alkanol. In particular, $E_1$ may be at least one P450 alkane hydroxylase ($E_a$) of EC 1.14.15.1 or AlkB alkane hydroxylase ($E_b$) of EC 1.14.15.3. The P450 alkane hydroxylase ($E_a$) is a component of a reaction system comprising two enzyme components cytochrome P450 alkane hydroxylase and NAD(P)H cytochrome P450 oxidoreductase of EC 1.6.2.4 or three enzyme components cytochrome P450 alkane hydroxylase of the CYP153 type, ferredoxin NAD(P)+ reductases of EC 1.18.1.2 or EC 1.18.1.3 and ferredoxin.

The AlkB alkane hydroxylase ($E_{1b}$) is a component of a reaction system comprising AlkB alkane hydroxylases of EC 1.14.15.3 which is a component of a reaction system comprising three enzyme components AlkB alkane hydroxylase of EC 1.14.15.3, AlkT rubredoxin NAD(P)+ reductase of EC 1.18.1.1 or of EC 1.18.1.4 and rubredoxin AlkG.

In particular, $E_1$ may be an AlkB alkane hydroxylase ($E_b$) also known as an alkane monooxygenase. More in particular, $E_1$ may comprise sequence identity of at least 50% to the alkane monooxygenase from *Pseudomonas putida* GPo1 encoded by alkBGT. Even more in particular, $E_1$ may comprise sequence identity of at least 50% to the polypeptide YP_001185946.1. More in particular, $E_1$ may comprise a polypeptide with sequence identity of at least 50, 60, 65, 70, 75, 80, 85, 90, 91, 94, 95, 98 or 100% to a polypeptide YP_001185946.1.

Enzyme $E_a$

In particular, the enzyme $E_1$ may at least be one P450 alkane hydroxylases ($E_a$) selected from the group consisting of:

AAO73954.1, AAO73953.1, XP_002546279.1, AAA34353.2, P30607.1, XP_002421627.1, XP_718670.1, CAA39366.1, XP_001527524.1, AAO73955.1, AAO73956.1, XP_002546278.1, EEQ43157.1, XP_718669.1, AAA34354.1, P10615.3, XP_002421628.1, 226487, P16141.3, CAA39367.1, Q9Y757.2, XP_001485567.1, AAO73958.1, XP_001383506.2, XP_460111.2, AAO73959.1, Q12586.1, XP_460112.2, AAO73960.1, Q12589.1, AAO73961.1, XP_460110.2, EEQ43763.1, XP_710174.1, EDK41572.2, XP_001482650.1, CAA75058.1, XP_002548818.1, Q12588.1, XP_002422222.1, XP_001383636.2, XP_001525381.1, XP_002548823.1, P30610.1, AAO73952.1, XP_002548428.1, CAA36197.1, XP_002421126.1, AAA34320.1, P16496.3, P30608.1, P24458.1, XP_717999.1, XP_001383817.1, Q9Y758.1, XP_001482092.1, XP_001383710.2, P30609.1, AAB24479.1, XP_457792.1, XP_001524144.1, XP_457727.2, XP_001525578.1, XP_002616743.1, XP_002614836.1, XP_001525577.1, AAO73957.1, Q12585.1, XP_001386440.2, XP_002616857.1,

XP_001483276.1, XP_500402.1, EDK39907.2, XP_500560.1, XP_001211376.1, XP_002560027.1, XP_504857.1, XP_500855.1, XP_504406.1, BAA31433.1, XP_500856.1, XP_501148.1, XP_746567.1, XP_001262425.1, XP_001274843.1, XP_002840588.1, XP_002377641.1, XP_001825995.1, XP_001400739.1, XP_718066.1, CAA35593.1, XP_664735.1, XP_002150795.1, XP_500097.1, XP_002483325.1, XP_504311.1, XP_500273.1, XP_002548817.1, EDP54484.1, XP_755288.1, XP_001260447.1, EFY97851.1, ACD75398.1, ADK36660.1, XP_001213081.1, XP_002377989.1, XP_001826299.1, XP_001554811.1, XP_501667.1, XP_002148942.1, ADK36662.1, XP_002565827.1, P30611.1, XP_001267871.1, XP_002372373.1, EFY84686.1, P43083.1, XP_001263094.1, XP_002148355.1, XP_002568429.1, XP_001817314.1, Q12587.1, XP_001396435.1, XP_001938589.1, XP_001388497.2, XP_663661.1, XP_003295335.1, XP_002152088.1, XP_001212071.1, Q12573.1, XP_002379858.1, XP_001821592.1, XP_002844341.1, XP_001394678.1, ACD75400.1, BAK03594.1, XP_003170343.1, XP_001265480.1, XP_002550661.1, EDP55514.1, XP_001528842.1, XP_749919.1, XP_001593058.1, P30612.1, EGC48494.1, EEH04429.1, XP_001585586.1, XP_003236182.1, XP_001400199.1, EEQ46951.1, XP_721410.1, EGP87864.1, XP_002380808.1, XP_001792771.1, XP_001208515.1, XP_001216161.1, XP_003071804.1, EFW16963.1, XP_002542118.1, XP_001936677.1, EGD95268.1, XP_003015678.1, XP_501748.1, XP_003169562.1, EFY96492.1, XP_682653.1, XP_002421356.1, CAK43439.1, EFY93677.1, XP_747767.1, XP_001244958.1, XP_003019635.1, XP_002847463.1, EGP83273.1, EGR52487.1, XP_002622526.1, XP_002563618.1, CBX99718.1, XP_001552081.1, XP_003066638.1, XP_003176049.1, ACD75402.1, BAA05145.1, XP_002482834.1, XP_001257501.1, XP_001934574.1, XP_001269972.1, XP_001587438.1, XP_001215856.1, XP_002149824.1, XP_001550556.1, XP_003011982.1, XP_001827121.1, XP_003233566.1, XP_003022481.1, EGR47044.1, EFQ34695.1, XP_003170005.1, BAG09241.1, XP_002796370.1, XP_001234709.1, XP_002563873.1, CAK40654.1, EEH19741.1, XP_003012518.1, EGD95716.1, XP_003239409.1, BAJ04363.1, XP_001537012.1, BAE66393.1, EGP85214.1, XP_002487227.1, AAV66104.1, EGE07669.1, XP_362943.2, XP_003016806.1, EFQ27388.1, XP_002384360.1, XP_002836323.1, XP_001274959.1, EFZ03093.1, XP_661521.1, XP_002849803.1, XP_001589398.1, AAR99474.1, XP_003189427.1, XP_001823699.1, XP_364111.1, XP_001262753.1, EFY86805.1, XP_001390153.2, XP_002384738.1, XP_001941811.1, XP_001220831.1, XP_003296981.1, XP_002480829.1, BAD83681.1, XP_001827526.2, XP_369556.1, CAK38224.1, EFQ26532.1, XP_002562328.1, XP_001904540.1, EGO52476.1, XP_002382002.1, XP_001225874.1, XP_958030.2, XP_002540883.1, XP_001908957.1, XP_001559255.1, XP_364102.1, EDP48064.1, XP_365075.1, XP_381460.1, CBX95930.1, XP_003054099.1, XP_361347.2, XP_002846961.1, XP_001214985.1, EFQ35175.1, XP_002479062.1, XP_001908613.1, XP_003345380.1, EGR50567.1, XP_002479350.1, XP_001394417.2, XP_001394159.2, XP_002146776.1, EGP86783.1, EFX02953.1, CAK45889.1, XP_003006887.1, XP_002541427.1, XP_750735.1, XP_001257962.1, EGO51720.1, XP_003005336.1, EGP83197.1, XP_002149832.1, XP_003052680.1, XP_365851.1, XP_001799910.1, XP_003347175.1, XP_002565258.1, EGR48918.1, EGR52524.1, XP_964653.2, XP_002147083.1, XP_002843935.1, EEH19393.1, CAC10088.1, EEH47609.1, EEQ92528.1, XP_001246560.1, XP_002626168.1, XP_003024880.1, XP_003169255.1, XP_003013780.1, XP_003235691.1, XP_746816.1, EGD98483.1, XP_001389925.2, XP_002842817.1, XP_002797278.1, ADK36666.1, XP_003305469.1, XP_001548471.1, XP_001806478.1, EFQ34989.1, XP_001552987.1, CAC24473.1, XP_002541530.1, EEQ89262.1, XP_001247332.1, XP_003066043.1, EDP47672.1, XP_002628451.1, XP_001910644.1, EGR44510.1, EFQ36733.1, XP_003052472.1, XP_001393445.2, XP_001522438.1, EGO04179.1, XP_001397944.2, CAK49049.1, EFQ30109.1, XP_001585052.1, EGO30123.1, XP_388496.1, XP_003173913.1, CBF76609.1, XP_003028593.1, EGO04180.1, CAK46976.1, XP_370476.1, XP_002145942.1, XP_003004457.1, ADK36663.1, XP_003040708.1, XP_003351473.1, EFY84692.1, XP_748328.2, XP_003190325.1, XP_002378813.1, EGR46513.1, XP_003033448.1, XP_002145326.1, XP_662462.1, XP_747469.1, XP_001935085.1, EGR45892.1, EGO01601.1, EGP89995.1, XP_001222615.1, XP_001224356.1, EGN93507.1, XP_001934479.1, BAK09464.1, EGO30124.1, XP_001267956.1, ADK36661.1, EFY97845.1, XP_001834501.1, EGO03790.1, XP_001884320.1, XP_003028899.1, AAP79879.1, EFY84206.1, BAK09467.1, XP_003030469.1, XP_001412594.1, XP_001834508.1, XP_001839436.2, XP_002583529.1, XP_001886288.1, XP_002843371.1, XP_001587730.1, BAK09418.1, BAK09442.1, EGO28830.1, EGE03365.1, EFZ01428.1, EGO03065.1, XP_001558890.1, XP_002487181.1, EGO29652.1, AAX49400.1, EFY92529.1, XP_002380252.1, XP_001884460.1, BAK09387.1, XP_001839366.2, XP_003031835.1, EFY99978.1, AAL67906.1, BAG09240.1, XP_002381768.1, XP_001800031.1, XP_001825073.2, BAE63940.1, XP_003028894.1, AAL67905.1, XP_002910303.1, EGO22856.1, XP_003028896.1, XP_681680.1, XP_002486603.1, XP_001838945.2, EGR50064.1, XP_001884349.1, XP_001883816.1, CAK37996.1, CAO91865.1, XP_003031227.1, XP_001258702.1, XP_001586739.1, XP_001560806.1, CBF69707.1, ADN43682.1, XP_001593179.1, XP_001886909.1, XP_001934479.1, XP_001587730.1, XP_001886909.1, XP_001831709.2, XP_001392650.1, XP_366716.2, CAL69594.1, XP_001269140.1, XP_002566307.1, XP_001555473.1, XP_663925.1, XP_001598033.1, XP_001835239.2, EGN97256.1, XP_001554305.1, NP_182075.1, XP_001560475.1, EFQ32286.1, XP_001216788.1, XP_002483975.1, AAC31835.1, NP_850427.1, XP_002143660.1, XP_003327130.1, BAJ78287.1, XP_002880182.1, ACB59278.1, EFQ36688.1, BAJ78285.1, BAJ78286.1, XP_001798699.1, EEH44101.1, BAJ78288.1, BAJ78284.1, EGG02425.1, EGG03011.1, AAA34334.1, NP_001189747.1, EGG02601.1, XP_002978645.1, EGG11203.1, XP_762610.1, XP_762620.1, XP_001545581.1, CAB44684.1, CAN80536.1, AAN05337.1, NP_001049423.1, XP_001791898.1, NP_001031814.1, XP_002279531.1, ABK94777.1, AAZ39646.1, XP_002880183.1, ABC68403.1,

XP_002839066.1, EGG03014.1, XP_002320074.1, NP_001182854.1, CBI38795.3, XP_002310605.1, NP_196442.2, XP_002270594.1, ABZ80830.1, XP_002275905.1, CBI38796.3, XP_002476978.1, CAB93726.1, EGG03624.1, EGG06527.1, NP_197710.1, XP_001768338.1, XP_002270673.1, BAJ86572.1, XP_002275806.1, CBI38797.3, XP_002320072.1, CAN60189.1, XP_002986290.1, XP_002465888.1, CAN80040.1, XP_002336104.1, XP_002988354.1, XP_002264277.1, EGD72898.1, XP_002866853.1, EAY95236.1, XP_002979701.1, XP_002988762.1, XP_002304502.1, XP_002873349.1, XP_003192947.1, CAN63571.1, NP_001053615.1, NP_176558.1, EGC49561.1, EGG09027.1, XP_002314581.1, XP_002446966.1, XP_002320802.1, ABC59095.1, XP_003323121.1, XP_002974639.1, XP_002395587.1, XP_002866852.1, XP_002319770.1, NP_001146262.1, NP_001169224.1, AAM65207.1, XP_002529058.1, XP_002886391.1, XP_002320071.1, XP_002446967.1, XP_757870.1, EAY95147.1, XP_002899664.1, EEH05830.1, XP_002874114.1, ADO24345.1, BAJ88802.1, BAA05146.1, XP_002963351.1, EAY88475.1, NP_195658.3, XP_002967944.1, ABC59093.1, XP_002275114.1, XP_003328407.1, CAN75428.1, BAJ86471.1, XP_002981144.1, XP_002277006.1, EAZ26110.1, ACN41008.1, XP_002899542.1, XP_001781614.1, EAY76187.1, BAK06758.1, XP_002511745.1, XP_002982626.1, XP_002963763.1, NP_001065111.1, ABF93892.1, XP_002314117.1, BAK06287.1, XP_001745327.1, NP_001047674.1, XP_002878665.1, XP_002974847.1, NP_179899.1, CAN80156.1, NP_001053543.1, ABC59094.1, XP_002328165.1, XP_002270628.1, XP_002275115.1, XP_002980688.1, XP_002465039.1, AAL91155.1, NP_195910.1, XP_002509820.1, NP_200694.1, CAA62082.1, AAL75903.1, XP_002468241.1, XP_002883546.1, XP_002862636.1, XP_002312905.1, EAY79269.1, AAM12494.1, XP_002875027.1, XP_758010.1, XP_002509524.1, AAP54707.2, XP_002869292.1, NP_001143079.1, ACF82946.1, XP_002270497.1, XP_002979685.1, XP_002465041.1, XP_002533544.1, AAG17470.1, XP_002985393.1, NP_191946.1, XP_002525608.1, AAZ39642.1, XP_002270428.1, XP_002529227.1, CBI24485.3, XP_001763206.1, EGG02922.1, XP_002974848.1, NP_001141467.1, CBI27149.3, NP_001130907.1, XP_002982474.1, NP_001048917.1, XP_002465889.1, ABZ80831.1, XP_002464461.1, EAY88476.1, BAJ90714.1, XP_002893825.1, ACN28568.1, XP_002452782.1, XP_002280004.1, XP_001764611.1, NP_001183394.1, BAJ89570.1, CBI24484.3, BAJ88840.1, ACG38359.1, CAN77648.1, BAJ91452.1, NP_001141345.1, XP_002282185.1, XP_002980994.1, XP_002299820.1, BAJ87982.1, BAJ91842.1, XP_003325270.1, XP_001760399.1, CBI34058.3, ADG34845.1, XP_002523775.1, EEH21852.1, Q50EK3.1, BAK06748.1, XPJ02963764.1, ACN34158.1, XP_001764503.1, XP_002311750.1, XP_001782495.1, XP_002988642.1, XP_002465625.1, XP_002892051.1, XP_002279649.1, NP_171666.1, ABK28430.1, BAC42067.1, AED99869.1, NP_174713.1, XP_001781706.1, ABG66204.1, XP_002964775.1, NP_001064901.2, XP_002961706.1, XP_002519477.1, XP_001559854.1, CBH32594.1, BAB92258.1, XP_002264897.1, AAL59025.1, XPJ02862576.1, ACL53124.1, XPJ02521476.1, NP_200045.1, BAJ89814.1, CBI38794.3, XP_776769.1, NP_001141372.1, EEC74485.1, EAY76557.1, XP_002318861.1, NP_001172660.1, XP_002880978.1, AAO00706.1, BAK07606.1, XP_002979336.1, BAC42841.1, BAF46296.1, XP_002306380.1, XP_002865907.1, ACG34921.1, XPJ02876375.1, NP_001056685.1, XPJ02264292.1, XP_002893443.1, NP_001066096.1, EEE53477.1, CBH32607.1, EAY94753.1, NP_001130939.1, NP_182121.1, XP_002437749.1, NP_191222.1, XP_002865881.1, XP_569708.1, XP_002279670.1, BAJ94774.1, ABF93894.1, BAD94304.1, ACG33785.1, NP_194944.1, NP_180337.1, AAB63277.1, BAJ85246.1, XP_002456654.1, ACN27732.1, XP_002445325.1, EER40289.1, XP_001838184.2, BAJ85532.1, XP_002866555.1, EAY88477.1, ACG47870.1, XP_002310074.1, XPJ02457224.1, EAZ25521.1, BAJ87689.1, NP_001044838.1, XPJ02521004.1, XP_002882043.1, XP_002527038.1, XP_002318721.1, XP_002979339.1, NP_176086.1, XP_001560028.1, ABC59092.1, ABF93891.1, ACR38435.1, EAY78983.1, NP_179782.1, CCA21696.1, XP_002334340.1, EFX88387.1, NP_001044554.1, XP_002321857.1, NP_173862.1, NP_195660.1, XP_001554079.1, EAZ13864.1, EEC67630.1, EAY76183.1, AAP54710.2, NP_001065112.2, ACD10924.1, XP_001559275.1, EEC67338.1, XP_002273811.1, ADJ68242.1, NP_001065698.1, CAN66874.1, CAB41474.1, XP_002868908.1, XP_002904660.1, CAR47816.1, NP_189243.1, EAY98229.1, XP_002448320.1, O81117.2, XP_002458797.1, XP_002277129.1, BAJ88829.1, CAN67559.1, BAK08034.1, XP_002894062.1, XP_002894891.1, XP_002279981.1, ABR16451.1, NP_201150.1, AAM60854.1, XPJ02521002.1, XP_002521474.1, XP_002875311.1, NP_195661.1, AAP79889.1, NP_175193.1, P98188.1, BAK08270.1, CBI21357.3, XP_002870817.1, XP_002904451.1, ABA95812.1, XP_002998647.1, NP_001066166.2, XP_002894690.1, EFY92064.1, XP_002278009.1, XP_002336002.1, CCA16508.1, XP_002868909.1, EAZ31703.1, C96517, EAY86526.1, XP_002307954.1, XP_002904638.1, XP_002266883.1, XP_002439880.1, XP_002892730.1, ADI52567.1, EGI61791.1, XP_002511196.1, EGG04372.1, XP_002511875.1, ACE75189.1, NP_001055681.1, XP_001589816.1, NP_001170655.1, XP_002300789.1, XP_001934479.1, XP_001587730.1, XP_001554079.1, XP_001559275.1, XP_002868908.1, XP_002998647.1, EFY92064.1, XP_002605799.1, BAC43393.1, ABK28457.1, AAL54887.1, BAC43161.1, XP_002333384.1, ZP_03631129.1, AAL84318.1, BAJ99856.1, XP_002593704.1, YP_001965159.1, XP_002454121.1, EFX88390.1, ABR16969.1, NP_177109.3, XP_002441724.1, NP_001166017.1, BAB92256.1, ACE75340.1, AAZ39645.1, XP_002312417.1, XP_002887239.1, NP_001172609.1, NP_001065766.1, XP_002515053.1, AAL54885.1, ABR16897.1, XP_002878579.1, NP_001140775.1, XP_003275955.1, ZP_08045694.1, BAJ94069.1, XP_001654558.1, XP_002436562.1, EAY88702.1, BAK03685.1, XP_003327629.1, XP_002322606.1, EEH42702.1, XP_002037976.1, NP_172774.1, XP_002282477.1, EFX88388.1, XP_002522465.1, EFZ21470.1, AAO41955.1, AAL54886.1, XP_002450277.1, XP_002862559.1, XP_002335046.1, XP_003328408.1, ACE75187.1, XP_001849294.1, XP_002444132.1, XP_002894061.1, EFN77015.1, EGI69992.1, CBI17962.3, AAL54884.1, XP_002998650.1, XP_002105150.1,

XP_002877615.1, EFZ22412.1, XP_002439815.1, XP_002300790.1, CBI40391.3, AEI59774.1, XP_002801151.1, XP_003325267.1, XP_001554577.1, EAY79865.1, XP_002465796.1, XP_002931035.1, ABA91371.1, ACE75338.1, XP_001592850.1, XP_001362981.1, XP_002271246.1, EGB11905.1, NP_176713.1, CBJ27248.1, NP_566155.1, EFX87732.1, EEC71661.1, ACG29046.1, NP_001130576.1, XP_001843663.1, ABK25134.1, EGI65081.1, XP_002722841.1, AAL67908.2, AAO15579.1, YP_122047.1, EFA04617.1, YP_001522424.1, ACB87383.1, NP_001027517.1, EEE52725.1, XP_002078257.1, XP_002722842.1, ZP_05128707.1, XP_003208874.1, AAK31592.1, ABA95747.2, NP_001181472.1, NP_001075572.1, XP_001108915.1, XP_001520882.1, XP_002063219.1, EFZ22408.1, AAL57721.1, EFW47740.1, AAQ20834.1, CAN74644.1, XP_002722849.1, BAC30028.1, CAN75729.1, XP_002115603.1, AAN72309.1, EEC68823.1, CAM18519.1, EAZ13863.1, XP_002906159.1, NP_001003947.1, ZP_01858832.1, XP_002882162.1, XP_002089195.1, XP_002892729.1, CAN68037.1, NP_001130648.1, NP_001166016.1, NP_172773.4, ADJ68241.1, EGI62551.1, EFN63658.1, XP_002000103.1, XP_001658673.1, XP_001367719.1, NP_775146.1, XP_001375048.1, AAH21377.1, NP_727589.1, XP_002271847.1, XP_001809620.1, XP_002897528.1, NP_190421.1, XP_002282468.1, XP_536868.2, EEE58297.1, XP_001992105.1, EAY82190.1, ADD20161.1, XP_001363065.1, EAU77129.3, EAY72807.1, EGG03077.1, NP_001181489.1, NP_001177869.1, XP_001966135.1, BAA99522.1, BAK07250.1, XP_002133118.1, NP_001042228.1, AAL57720.1, XP_002897529.1, AAA35712.1, YP_002275016.1, NP_000770.2, XP_002721578.1, XP_321208.4, AAM09532.1, EFN61085.1, BAK06179.1, EFX88389.1, YP_001602608.1, XP_513140.3, NP_001182438.1, AAD31068.1, NP_001093242.1, XP_001367758.2, EFZ18984.1, YP_691921.1, CAH59968.1, AAS80270.1, CAH59967.1, ACQ99381.2, YP_003810988.1, YP_957888.1, CBW44755.1, ZP_05042596.1, YP_01913735.1, ZP_05043097.1, ADQ00145.1, YP_004494060.1, ZP_08206912.1, BAE78452.1, NP_114224.1, ACZ56357.1, YP_640381.1, ZP_04384919.1, ZP_08025219.1, ZP_07715822.1, ZP_06847816.1, YP_001702784.1, AEK27137.1, ZP_07716433.1, ZP_08199554.1, YP_004495520.1, YP_345718.1, ZP_08022914.1, YP_001851443.1, BAG50428.1, YP_001135848.1, BAF95905.1, YP_345695.1, ACP39691.1, ACP39664.1, ACP39635.1, ACP39633.1, ACP39710.1, ACP39698.1, ACP39711.1, BAE47475.1, BAE47474.1, ABW76858.1, ACO50699.1, ACP39643.1, ACP39639.1, ACP39708.1, ACM68663.1, ACP39642.1, ACP39684.1, ACP39636.1, ZP_05095005.1, ACP39652.1, BAE47473.1, ACM68664.1, ACP39646.1, ACP39680.1, ACP39692.1, ACP39675.1, ACP39632.1, ZP_05129284.1, ACP39706.1, ACP39695.1, ACM68665.1, ACP39654.1, ACP39665.1, ACP39649.1, BAE47472.1, ACM68668.1, ACP39676.1, ACP39648.1, ACP39647.1, ZP_01102434.1, ACM68666.1, ACP39641.1, ACM68669.1, ZP_01625037.1, ACP39690.1, ACP39696.1, ACP39697.1, ACP39707.1, ACP39682.1, ACP39650.1, ACP39638.1, ZP_05126641.1, CAH04396.1, ACP39685.1, ZP_01102687.1, ACJ06772.1, YP_001413041.1, YP_552058.1, ADE05601.1, ADI19685.1, BAE47479.1, ZP_01626700.1, ZP_01618279.1, CAH61448.1, YP_001411305.1, YP_003591161.1, ZP_01615522.1, ACM68667.1, ACP39651.1, ZP_05095535.1, ZP_01618489.1, NP_418882.1, ADI19983.1, ACP39677.1, BAE47476.1, ACP39655.1, ACP39656.1, ADI19696.1, BAE47477.1, YP_001413399.1, YP_459878.1, BAE47480.1, BAE47481.1, ACP39653.1, BAE47478.1, YP_001681656.1, ZP_01618281.1, ZP_01627262.1, YP_001413057.1, YP_760740.1, YP_001242466.1, YP_001203574.1, CAH61454.1, YP_002129656.1, YP_001672075.1, ACP39709.1, YP_001990805.1, NP_946959.1, YP_001203575.1, YP_783213.1, YP_003059227.1, YP_004110202.1, ACP39645.1, YP_487538.1, CAH61451.1, YP_570816.1, YP_534107.1, YP_001413223.1, YP_001242465.1, YP_557448.1, ZP_08631162.1, NP_773883.1, ZP_00997728.1, ACP39683.1, NP_768493.1, NP_773882.1, ZP_08271781.1, CAH61449.1, YP_003883668.1, YP_003332953.1, YP_004535688.1, YP_495502.1, YP_459378.1, ZP_08700267.1, ZP_01863452.1, ZP_06860085.1, BAE47487.1, YP_617903.1, ZP_08207422.1, BAE47486.1, ZP_01041003.1, BAE47484.1, ACR78197.1, CAH61456.1, ZP_01858113.1, ACP39681.1, BAE47485.1, ACP39673.1, BAE47483.1, ACP39669.1, BAE47482.1, ACP39674.1, ACP39704.1, ACP39703.1, YP_497095.1, ACP39672.1, ACP39702.1, ACP39670.1, ACP39666.1, YP_458852.1, ACP39687.1, ACP39688.1, ACP39634.1, ACP39686.1, ACP39660.1, ACP39700.1, YP_001411309.1, ZP_01465241.1, ACP39701.1, ACP39679.1, ACP39657.1, ACP39694.1, ACP39659.1, ACP39671.1, ACP39693.1 and YP_003342921.1.

Enzyme $E_b$

In another example, the enzyme $E_1$ may at least be one AlkB alkane hydroxylase ($E_{1b}$) selected from the group consisting of:

YP_001185946.1, Q9WWW6.1, YP_957898.1, YP_957728.1, YP_694427.1, BAC98365.1, ZP_00957064.1, CAC86944.1, YP_001672212.1, CAB59525.1, ACH99213.1, ACH99215.1, ACH99216.1, AAK56792.1, ACH99229.1, ACS91348.1, AAP41820.1, ZP_05128075.1, CAM58121.1, CAM58085.1, ACQ44675.1, ACZ62808.1, ZP_01738706.1, ZP_01916228.1, ZP_01225325.1, YP_001023605.1, ACJ22747.1, ACT91140.1, AAT91722.2, CBA27418.1, YP_001889129.1, EGC97932.1, ACT91201.1, ZP_05083049.1, YP_554098.1, ZP_01900149.1, ADG26619.1, ADG26657.1, ADG26640.1, ZP_06838771.1, ADG26649.1, ADG26651.1, ZP_02374120.1, YP_368326.1, ZP_02380481.1, ADG26643.1, ADG26628.1, YP_442346.1, ADG26620.1, ADG26647.1, ZP_07673680.1, ADG26638.1, YP_002232139.1, YP_001118743.1, ZP_01764629.1, YP_108945.1, YP_334185.1, ZP_04897834.1, ZP_02889567.1, YP_620386.1, YP_002897546.1, ZP_02166109.1, ZP_02904755.1, ADG26639.1, YP_001892637.1, ADG26642.1, ZP_04939380.1, ZP_02464124.1, YP_102417.1, CAC36356.1, ACJ22727.1, YP_001764240.1, YP_002765609.1, YP_001945311.1, ZP_03586616.1, ACJ22665.1, ZP_03574223.1, CAC37038.1, ZP_02456517.1, YP_001807560.1, YP_002779449.1, AAK97454.1, YP_002912304.1, ACR55689.1, YP_003397515.1, YP_004361423.1, YP_772734.1, ACJ65014.1, ACT31523.1, ACJ22750.1, ZP_07375042.1, YP_002776786.1, ACB11552.1, ZP_02363472.1, ADG26653.1, ZP_04383196.1, ZP_02356342.1, ACJ22751.1, YP_952571.1, ACU43494.1, YP_001135977.1, YP_002764193.1, YP_003855036.1, YP_004078475.1, AAK97448.1, ZP_04388098.1,

ACX30747.1, ADG26632.1, ACJ22719.1, ADO21492.1, ZP_05061580.1, ADR72654.1, ACZ65961.1, ACX30755.1, YP_001849604.1, AAV64895.1, YP_004495037.1, YP_702497.1, YP_001069662.1, ZP_06850622.1, BAF34299.1, CAB51024.2, YP_004008018.1, YP_003768535.1, ACJ65013.1, ZP_07282765.1, YP_886209.1, ACJ22725.1, ZP_08155372.1, YP_004493362.1, ZP_05228000.1, ZP_07717360.1, BAD67020.1, YP_004524245.1, ZP_07715778.1, NP_217769.1, ACS91349.1, YP_960105.1, ZP_07014137.1, YP_004746682.1, ZP_08022271.1, ACN62569.1, ADQ37951.1, YP_003647687.1, YP_003837040.1, ADG26600.1, YP_002768905.1, ZP_08553310.1, ADG26597.1, ACJ22749.1, ADG26598.1, YP_001704327.1, ZP_04385381.1, ZP_04751264.1, ADG26609.1, ADG26610.1, ZP_06417258.1, ADG26607.1, ADP98338.1, YP_003275257.1, YP_004084103.1, ADG26630.1, ADG26625.1, ADG26605.1, ADG26599.1, ZP_05218167.1, ADQ37950.1, YP_921354.1, ADG26645.1, ADG26612.1, YP_004493370.1, YP_638501.1, YP_003809668.1, NP_962298.1, ZP_04750514.1, ADG26608.1, ADT82701.1, ACJ06773.1, YP_120833.1, ADG26618.1, ADG26602.1, ADG26623.1, ZP_04383566.1, ZP_08122407.1, YP_004077166.1, ZP_05041651.1, ZP_04608296.1, ABU93351.2, YP_003658078.1, ADQ37949.1, ADG26652.1, YP_002765850.1, AAK97447.1, CAD24434.1, CAC40954.1, ACT91203.1, YP_120829.1, ZP_07282558.1, YP_003298195.1, YP_001851790.1, ZP_05827357.1, ADG26633.1, CAB51020.1, YP_953908.1, ZP_07990416.1, YP_119532.1, ZP_08442348.1, ZP_08276444.1, ZP_04661203.1, ABO12068.2, YP_001846325.1, ADQ37952.1, ZP_08198697.1, ZP_00996652.1, YP_001707231.1, ZP_08433663.1, ZP_08205256.1, YP_003732372.1, YP_906529.1, ACT91204.1, YP_001506534.1, YP_001713880.1, YP_883357.1, YP_004525252.1, ADG26604.1, YP_001134633.1, ZP_08195602.1, ZP_06690500.1, ZP_05826167.1, ADY81595.1, ZP_06056754.1, AAK31348.1, YP_251715.1, ZP_08461977.1, ZP_05847237.1, YP_712218.1, YP_001084670.1, ZP_04387164.1, YP_260041.1, YP_002873097.1, ADG26614.1, AAK97446.1, YP_001280943.1, ZP_04386125.1, AAC36353.2, CCA29159.1, CAD10804.1, CCA29151.1, CAC40953.1, CCA29161.1, ABA55770.1, AAS93604.4, CCA29173.1, CCA29155.1, CCA29156.1, ABA55772.1, CCA29154.1, ABA55793.1, CCA29162.1, CCA29170.1, ZP_03824539.1, CCA29166.1, CCA29136.1, ZP_06065934.1, ABB54493.1, CCA29169.1, YP_003112137.1, CCA29127.1, CCA29148.1, CCA29160.1, ZP_06057458.1, ABA55773.1, YP_004016090.1, CCA29139.1, YP_480358.1, ABA55787.1, CCA29150.1, CCA29130.1, ZP_07775830.1, ABA55779.1, CCA29132.1, YP_003732938.1, BAB33284.1, CCA29149.1, CCA29145.1, ABA55783.1, CCA29137.1, CCA29129.1, CCA29158.1, CCA29176.1, CCA29142.1, CCA29144.1, BAB33287.1, CCA29133.1, CCA29140.1, CCA29135.1, ZP_06066074.1, ZP_03823182.1, CCA29171.1, CCA29152.1, CCA29131.1, ABA55780.1, CCA29163.1, CCA29143.1, CCA29153.1, YP_001580600.1, CCA29134.1, CCA29138.1, YP_046098.1, ZP_06072466.1, ZP_05361594.1, ACU43504.1, CCA29147.1, CCA29146.1, ZP_06061712.1, ACT91185.1, ACT91147.1, ACT91178.1, ACT91167.1, ACT91181.1, ACT91188.1, ZP_06069784.1, ACT91205.1, ZP_06725872.1, ACT91171.1, CCA29128.1, ABY56787.1, ADE05602.1, ACU43474.1, ACJ22718.1, ABB90688.1, ACU43519.1, ABB96093.1, ACU43485.1, ACU43493.1, ABW76857.1, ACT91163.1, ACJ22673.1, ZP_06188150.1, ACT91242.1, ACT91225.1, ACT91211.1, ACU43479.1, ACU43491.1, ACU43522.1, ACU43486.1, ACT91221.1, ACJ22662.1, ACU43506.1, ACU43487.1, ACT91259.1, AAA97866.1, ACU43502.1, YP_001252544.1, ABB96084.1, ACU43520.1, ACJ22668.1, ACU43503.1, ACT91230.1, ABA55777.1, ACT91231.1, ZP_01748311.1, ACJ22724.1, ACU43475.1, ACU43511.1, ACU43490.1, ZP_08330953.1, ACU43484.1, CBX01596.1, ACT91168.1, YP_096989.1, ACT91215.1, YP_125370.1, ACT91233.1, ACU43478.1, ADE05603.1, ACJ22715.1, ACU43512.1, ACT91196.1, ACJ22692.1, ACU43510.1, ACU43521.1, ACT91174.1, ACT91213.1, ACT91142.1, ACT91206.1, ACT91216.1, ACT91182.1, ACT91255.1, ACT91246.1, ACT91217.1, ACT91155.1, ACT91240.1, ACT91207.1, ACU43495.1, YP_128249.1, ACT91160.1, YP_004052990.1, ACT91226.1, ACU43507.1, ABO61855.1, ACT91214.1, ACT91220.1, YP_001188237.1, ACJ22689.1, ZP_01689499.1, YP_004379711.1, ACJ22748.1, ABB90683.1, ACT91223.1, ACT91235.1, ABO61786.1, ACU43508.1, ACU43492.1, ACT91219.1, ACT91244.1, ABO61856.1, ACT91239.1, ACU43473.1, ABO61850.1, ACT91262.1, ACT91261.1, ACT91224.1, ACU43499.1, ACU43488.1, ADO21767.1, YP_004654946.1, ADO21777.1, ABB96089.1, ABO61852.1, ABO61847.1, ACT91222.1, ADO21764.1, ACU43477.1, ADO21773.1, ABO61787.1, ABB96080.1, ABO61857.1, ACT91228.1, ABB96070.1, ADO21744.1, ACT91245.1, CAG17608.1, ADO21747.1, YP_001349162.1, ABK63807.1, ZP_06879583.1, NP_250216.1, ACT91234.1, ZP_01364874.1, ABO61789.1, ADO21772.1, ACU43516.1, ACU43505.1, ACU43501.1, ACT91236.1, ZP_07792758.1, ACZ64723.1, ADO21743.1, ADO21759.1, ACZ64752.1, ADO21755.1, ACD75517.1, YP_790621.1, ACB11551.1, ADO21748.1, NP_251264.1, ZP_01365940.1, ADO21762.1, ADO21739.1, ACU43496.1, ABO61854.1, ZP_06878434.1, ACU43489.1, ACU43483.1, ADO21746.1, ACT91237.1, ZP_01895378.1, ACT91164.1, ADO21736.1, ACJ22711.1, ACZ64754.1, ZP_05042146.1, ADO21688.1, ADO21648.1, YP_001348003.1, ADP98656.1, ADO21737.1, ADO21760.1, ADO21754.1, ADO21740.1, ACZ64758.1, ACU43497.1, ZP_01912185.1, ABB96111.1, ACU43482.1, ACB11549.1, ADO21775.1, CCA29157.1, ADO21681.1, ADO21668.1, ADO21656.1, ACU43517.1, ACT91165.1, ACJ22695.1, ACJ22688.1, ABB96071.1, ADO21763.1, ACT91241.1, ADO21735.1, ACB11550.1, ADO21778.1, ACT91172.1, ADO21765.1, ABB96087.1, CBJ30233.1, ACJ22752.1, ABB96105.1, ACB15251.1, ACJ22694.1, ACZ64741.1, ACZ64706.1, ABB96108.1, ACT91191.1, ABB96101.1, ABB90691.1, ACZ64745.1, YP_691842.1, ABB96075.1, ABB90682.1, ABB90690.1, ADO21676.1, ADO21679.1, ABO61768.1, YP_435857.1, ACJ22722.1, ACT91238.1, ACZ64725.1, CAC14062.1, ADO21682.1, ACZ64771.1, ACZ64718.1, ACZ64724.1, ADO21670.1, ADO21667.1, CAC37048.1, ACZ64708.1, ABB96092.1, ACJ22687.1, ACZ64703.1, ADO21690.1, ABB92364.1, ACB11547.1, ACZ64720.1, ADO21655.1, ACZ64717.1, ADO21680.1, ACZ64757.1, ACZ64733.1, ACT91144.1, ACU43481.1, ACT91179.1, ZP_02181409.1, ACZ64704.1, ABB96073.1, ACJ22675.1, ACZ64721.1, ABB96090.1, ACJ22729.1, ACU43515.1, ZP_01307000.1, ABB90685.1, YP_003862088.1, ACZ64715.1, ACZ64710.1, ACJ22735.1, ABB90687.1, ADO21661.1, ADO21674.1, ACT91177.1, ABB54492.1, ABB96076.1,

ABB92365.1, ACT91194.1, ADO21689.1, ACJ22691.1, ABB90681.1, ADO21649.1, ADO21671.1, ACZ64728.1, ABB96095.1, CAC40945.1, ADO21652.1, ADO21665.1, ADE08461.1, ADO21678.1, ACZ64705.1, ACJ22690.1, ADO21675.1, ADO21685.1, ABB96072.1, ACJ22736.1, ACB11540.1, ABB96091.1, ACI04540.1, ACT91251.1, ACT91146.1, ACT91166.1, ACT91156.1, ADO21752.1, ADO21673.1, ADO21725.1, ABB96104.1, ABB90694.1, ABB90696.1, ACT91173.1, ADO21647.1, ZP_03700804.1, ACT91232.1, ADO21694.1, CAC40949.1, ABB92361.1, ACT91195.1, ACI04538.1, ADO21691.1, ACJ22685.1, ADO21653.1, ABS12461.1, ACZ64736.1, ACZ64772.1, ABB90680.1, ADO21659.1, ACZ64774.1, ADO21684.1, ADO21729.1, ADO21650.1, ADO21733.1, ACZ64755.1, ACZ64751.1, ABA55775.1, ADO21738.1, CCA29174.1, ADO21669.1, ACZ64744.1, ADO21654.1, ADO21768.1, ABB96106.1, CCA29168.1, ACT91176.1, ACB11555.1, ABB90695.1, ADO21660.1, ACJ22666.1, ACZ64778.1, ADO21766.1, ADO21677.1, ZP_02161687.1, CCA29165.1, ADO21745.1, ACB11548.1, ABB90689.1, ABB96107.1, AAT46052.1, ADO21718.1, ADO21722.1, ABB96088.1, EFW40271.1, ADO21686.1, ABB96103.1, ACU43500.1, ACB11536.1, ABB92360.1, CCA29167.1, ACT91199.1, ACZ64770.1, ACJ22716.1, ABA55786.1, ACZ64737.1, ABB96083.1, ACJ22676.1, ACZ64735.1, ACT91212.1, ACJ22765.1, CAJ01371.1, CAC17734.1, ABD36389.1, ACB11537.1, CAC08515.1, ACZ64714.1, ACU43513.1, ABB96082.1, ADN21387.1, ADO21711.1, ABD36392.1, ABR10770.1, CAC37049.1, ABB96098.1, ABB90692.1, ACB11535.1, ACZ64768.1, ACJ22756.1, ABB96094.1, ABA55791.1, ABB96078.1, ACT91141.1, ACZ64779.1, ACZ64750.1, CAJ01370.1, ACZ64753.1, ACU43480.1, ABA55794.1, ABB96085.1, ABB96110.1, YP_004448035.1, ACZ64709.1, ABB96102.1, ACZ64773.1, CCA29175.1, ACZ64749.1, ACZ64756.1, ACZ64781.1, ABO61777.1, ACZ64759.1, ACZ64764.1, ACZ64740.1, ACT91249.1, ZP_03702922.1, ACB11545.1, ACZ64775.1, ACZ64769.1, ACT91145.1, ACZ64742.1, ACT91254.1, ACZ64762.1, ACZ64716.1, ACZ64777.1, ADM26559.1, ABB96096.1, ACZ64780.1, ZP_01201250.1, CAH55829.1, ZP_01052921.1, ABB96077.1, ADO21658.1, ACT91161.1, ABB90684.1, ACR56750.1, ABB90697.1, ACZ64746.1, ABB92367.1, ACT91139.1, ACZ64763.1, ACT91200.1, ABO61773.1, ABB96081.1, ACZ64748.1, ACZ64782.1, ACU43498.1, ADO21651.1, ABB90679.1, BAG06233.1, ACZ64747.1, ABB96086.1, ACZ64761.1, ABB92370.1, ABO61774.1, ACT91175.1, ABB90686.1, ACB11546.1, ZP_01740604.1, ABO61785.1, YP_001531377.1, XP_001434539.1, ABA55767.1, ABO21865.1, ABF55636.1, ABA55751.1, ABB90698.1, ADD12311.1, ACZ64765.1, ABB92366.1, ABB92368.1, ACI04539.1, XP_001023288.1, ACZ64783.1, ADO21692.1, ZP_01753800.1, ACZ64760.1, ACZ64700.1, ZP_01055480.1, ACZ64767.1, ACZ64701.1, ABA55745.1, ABA55752.1, ACZ64766.1, YP_614640.1, ABA55759.1, ADO21723.1, BAG06232.1, ZP_01002389.1, ABB90693.1, ACT91264.1, ABB92358.1, BAF99026.1, ABR10769.1, ZP_00959618.1, AEA08580.1, ADD22986.1, CAB51023.1, CAC40958.1, ADO21709.1, CAB51025.1, ACI15226.1, ACJ22680.1, ZP_05741459.1, ACT91248.1, ABU48567.1, ABO61792.1, ACJ22754.1, EFN53276.1, AAL87644.1, ACT91209.1, ZP_02147281.1, ACU43518.1, ACZ64776.1, ACB11543.1, ACT91151.1, ACJ22764.1, ACT91159.1, ABA18186.1, AEA08579.1, ADO21770.1, ABF55634.1, CAA27179.1, ABA55741.1, ADO21705.1, ZP_01754375.1, ACB11541.1, ACR56751.1, ACT91250.1, ADO21769.1, ADO21753.1, ABB96097.1, ACT91208.1, ABO21867.1, ADO21757.1, ACB11554.1, ABA55749.1, CAC40951.1, ADO21719.1, ABB96074.1, ZP_00954267.1, ZP_05786269.1, AEH76912.1, ABA55742.1, ABA55748.1, BAG06236.1, ADO21732.1, ABA55750.1, ABA55768.1, ACT31522.1, ZP_05090796.1, ACZ64739.1, YP_915886.1, ADO21731.1, CAC40948.1, XP_001032273.1, AEH76911.1, ABA55743.1, ABO61769.1, ABA55755.1, ZP_05122263.1, ADO21756.1, ABA55744.1, ABA55746.1, ZP_01901011.1, ZP_02150761.1, ADO21742.1, ACR56752.1, ABA55747.1, ABF55637.1, ABA55740.1, ABA55760.1, ZP_00948812.1, ABA55804.1, ADO21771.1, ZP_05342453.1, ABF55638.1, YP_508336.1, ABB92357.1, ZP_01049702.1, ABU48546.1, ABU48555.1, ABA55764.1, ABO21866.1, ZP_05079274.1, ZP_01880441.1, ACZ64738.1, ZP_05842058.1, ACT91218.1, ABA55769.1, ABA55739.1, ABA55803.1, ACT91247.1, ABA55782.1, ACZ17539.1, ABB92359.1, ACH69966.1, ZP_01035050.1, ACZ17537.1, ABA55774.1, ACZ64729.1, ACZ17538.1, ZP_01751972.1, ACZ64731.1, ACZ64702.1, AAR13803.1, AEJ28400.1, ZP_05099213.1, CAB51021.1, ACZ17531.1, AEH76914.1, ZP_05051648.1, ACZ64726.1, ACZ17540.1, ACZ64727.1, ZP_02152773.1, ACT91253.1, ACZ17536.1, XP_001423873.1, ACZ17534.1, YP_168645.1, ACZ17520.1, ABY56786.1, ACB11539.1, ZP_01157350.1, AEH76910.1, ABY56784.1, AAY85982.1, ACT91257.1, ACB11544.1, ACZ17532.1, ZP_01746661.1, ABA55771.1, BAG06235.1, EGR32049.1, YP_001166282.1, ABO61799.1, ABA55757.1, AEH76915.1, ACO59264.1, ABO26125.1, AEA08577.1, ACT91265.1, ABY56785.1, ACZ17528.1, ABO61798.1, ADO21749.1, ACT91263.1, ACT91252.1, ACZ64722.1, ABO61771.1, ACZ17526.1, ABO26123.1, ADO21714.1, ZP_01000906.1, ABO61796.1, ADC29534.1, ACB15250.1, ACD47155.1, ACZ17525.1, ACB11553.1, ABD36391.1, AEH76913.1, ACZ17523.1, ABO61781.1, ACZ17524.1, ZP_01914093.1, ACB11538.1, ZP_01015838.1, ACJ22693.1, ACB15252.1, CAC86945.1, ACO59265.1, ABO61791.1, ACZ17521.1, ABO26124.1, ACZ64732.1, ACU43514.1, ACT91256.1, ACM63043.1, ACS75820.1, ZP_08666479.1, CAH03133.1, BAG06234.1, AEH76916.1, ABO61790.1, ABE72965.1, ACZ64711.1, ACB11542.1, AAY26148.1, ABA55776.1, ACZ17522.1, ACZ64734.1, AEA08578.1, ACZ17530.1, ZP_04062748.1, ACJ22755.1, NP_969039.1, AAY26149.1, ACJ22761.1, ABU48543.1, ZP_08414255.1, AAT91720.1, ZP_01444283.1, ABA55796.1, ABU48542.1, YP_001042010.1, YP_001234392.1, YP_351510.1, ACZ64730.1, ZP_08634611.1, ACZ17529.1, ACJ22667.1, AAT91719.1, YP_004283531.1, ABO61801.1, ACZ17519.1, ABO15266.1, CAB51040.1, ACZ64707.1, ACJ22766.1, ABO26121.1, ZP_01878984.1, CAB51039.1, ABA55795.1, ABO15269.1, ABO15247.1, ACJ22763.1, ABO15251.1, ACZ17527.1, ABO15270.1, ACJ22769.1, ADE06670.1, ZP_05780387.1, ABO61770.1, ACT91258.1, ABO15258.1, ABO15257.1, ABU48545.1, CAC86946.1, ABO15267.1, ZP_01741446.1, ABU48544.1, YP_002296646.1, AEH76917.1, ADC29550.1, YP_002527219.1, ABK88246.1, ADN21388.1, ACT91210.1, ZP_05064795.1, ABJ16487.1, XP_002675644.1, ABJ16489.1, ADA71089.1, ADA71088.1, AAT46053.1, ZP_01744806.1, ZP_01037964.1, ZP_00955262.1, ABJ16493.1, YP_001840157.1, ZP_00964204.1, ABB40596.1, ACB15249.1, ADD82963.1, YP_004499590.1, ZP_01011524.1, ACJ22758.1, ZP_01748906.1, ACV30052.1, ZP_06191942.1, YP_001188029.1,

ACD63080.1, YP_166583.1, AAV41375.1, ZP_00998265.1, ACJ22757.1, ABB13506.2, ABI13999.1, ABI14004.1, ABB13509.1, YP_371980.1, ZP_01755711.1, ZP_05065835.1, ZP_00959368.1, XP_001020063.1, ABJ16481.1, ABI14006.1, ZP_05101918.1, ZP_01913733.1, ABI14001.1, ABM92270.1, ABI14003.1, CAH03132.1, YP_973211.1, ABA55797.1, YP_003578527.1, ABJ16483.1, ABJ16482.1, CBY78068.1, ACT91260.1, YP_509155.1, ABB13508.1, ABJ16485.1, ABO61779.1, ABI14005.1, ACM63042.1, ADC29543.1, ZP_02153440.1, YP_709335.1, ABI13998.1, ABI14002.1, AAB70825.1, ACX30751.1, ABI14000.1, YP_003617173.1, ZP_01155421.1, ACX30752.1, NP_542887.1, ADC29546.1, AAC38359.1, ADC29541.1, XP_001020064.1, ZP_01442436.1, ZP_05103090.1, ADC29544.1, ABO61809.1, AAY89939.1, ACH99235.1, CAH55830.1, ABO26095.1, YP_004011670.1, ABO26084.1, ADA71083.1, ABO26087.1, ABO61806.1, ADC29531.1, ABO26109.1, ACJ22753.1, ABO26089.1, ABO26093.1, ABO26092.1, ABO61827.1, ABO26105.1, ABO26112.1, AAT91721.1, ABO26120.1, ABO26090.1, ABO26088.1, ABO61811.1, ABO61783.1, CAH55827.1, ACH99232.1, ABO61828.1, ADC29530.1, ACH99234.1, AAQ88276.1, CAH55823.1, ABO26103.1, ACH99233.1, ABO61836.1, ABO26094.1, ABO61840.1, YP_004534277.1, ZP_05845010.1, ABO61821.1, ACH99231.1, AAV68403.1, ABO61839.1, CAH56098.1, ABO26085.1, ABO61826.1, ABO61822.1, ABO26110.1, ABO61810.1, ABO61844.1, ABO61825.1, ABO26099.1, ACJ22767.1, ABO26102.1, YP_004535707.1, ACJ22762.1, ABO26097.1, BAC65444.1, ABO61829.1, YP_114083.1, CAH55828.1, ABO26106.1, YP_552229.1, NP_049190.1, ABO26116.1, CAH56107.1, CAM32407.1, ABO26101.1, ABO61841.1, ABM79805.1, ZP_05075249.1, AAC27438.2, YP_003754872.1, ADC29532.1, ADA71139.1, ADA71107.1, ADA71095.1, YP_001268217.1, ADA71126.1, ADA71094.1, CAH56108.1, ADC29533.1, ADA71085.1, ZP_05054453.1, ADA71097.1, ADA71086.1, ADA71114.1, ADC29548.1, ADA71101.1, ADC29547.1, ADA71138.1, ADC29542.1, ADA71098.1, ADA71128.1, ADA71105.1, ADA71093.1, ADA71135.1, ADA71100.1, YP_557479.1, ADA71113.1, ADA71091.1, ADC29537.1, ADA71084.1, ADA71090.1, CAH56094.1, XP_002945767.1, ADA71137.1, ADA71103.1, ADA71118.1, ADA71133.1, ADA71102.1, ADC29536.1, CAH56100.1, CAH56101.1, ACI15225.1, ACI15225.1, ABO26091.1, CAH55826.1, CAH55824.1, ZP_08484419.1, ADA71111.1, ACJ22759.1, CAH55825.1, CAH56106.1, CAH56099.1, CAC40957.1, ZP_05075037.1, CAH56102.1, ZP_06846296.1, ABJ16491.1, ZP_05067177.1, XP_001698107.1, BAH10789.1, BAH10791.1, BAH10793.1, BAH10788.1, ABJ16490.1, BAH10800.1, BAH10790.1, BAH10792.1, ZP_05075214.1, BAH10799.1, BAH10795.1, BAH10787.1, BAH10798.1, BAH10794.1, BAH10801.1, BAH10796.1, BAH10797.1, BAH10802.1, CAH56095.1, CAH56096.1, ADC29538.1, ABX76425.1, ZP_06727686.1, ZP_07774883.1 and YP_001615042.1.

Enzyme $E_2$

Enzyme $E_2$ may be capable of converting a 1-alkanol to the corresponding 1-alkanal. In particular, $E_2$ may be at least one P450 alkane hydroxylases ($E_a$) of EC 1.14.15.3, AlkB alkane hydroxylases ($E_b$) of EC 1.14.15.3, alcohol oxidase ($E_c$) of EC 1.1.3.20 or alcohol dehydrogenase ($E_d$) of EC 1.1.1.1 or EC 1.1.1.2. More in particular, $E_2$ may be selected from the group consisting of P450 alkane hydroxylase ($E_a$), AlkB alkane hydroxylase ($E_b$), alcohol oxidase ($E_c$) of EC 1.1.3.20, AlkJ alcohol dehydrogenase ($E_{di}$), and alcohol dehydrogenase ($E_{dii}$) of EC 1.1.1.1 or 1.1.1.2.

In particular, $E_2$ may be an AlkB alkane hydroxylase ($E_b$) also known as an alkane monooxygenase. More in particular, $E_2$ may comprise sequence identity of at least 50% to the alkane monooxygenase from Pseudomonas putida GPo1 encoded by alkBGT. Even more in particular, $E_2$ may comprise sequence identity of at least 50% to the polypeptide YP_001185946.1. More in particular, $E_2$ may comprise a polypeptide with sequence identity of at least 50, 60, 65, 70, 75, 80, 85, 90, 91, 94, 95, 98 or 100% to a polypeptide YP_001185946.1.

Enzyme $E_c$

The alcohol oxidase ($E_c$) may be selected from the group consisting of:

AAS46878.1, ACX81419.1, AAS46879.1, CAB75353.1, AAS46880.1, XP_712350.1, XP_002422236.1, XP_712386.1, EEQ43775.1, XP_001525361.1, XP_001386087.1, XP_459506.2, CAB75351.1, CAB75352.1, XP_001385255.2, EDK39369.2, XP_001484086.1, XP_002618046.1, XP_002548766.1, XP_002548765.1, XP_003041566.1, XP_003328562.1, XP_001214264.1, XP_001904377.1, XP_658227.1, XP_001591990.1, XP_753079.1, XP_002569337.1, XP_001268562.1, XP_003348911.1, EGP90120.1, XP_001389382.1, EER37923.1, XP_001264046.1, EGO58212.1, XP_001554225.1, XP_003298648.1, XP_959005.1, XP_002841296.1, XP_001940486.1, EGR52262.1, EEQ89581.1, EGD99881.1, EFQ33555.1, XP_001821106.1, XP_002622231.1, EGG03784.1, EGC44059.1, XP_003018036.1, XP_003011696.1, EFY90752.1, XP_001227812.1, XP_758170.1, XP_001243546.1, XP_002479333.1, XP_003344707.1, EFW14100.1, XP_003071927.1, XP_003171263.1, XP_003051757.1, XP_002147053.1, EEH19591.1, EEH50473.1, XP_001792978.1, XP_387094.1, EFY98644.1, XP_002788971.1, XP_002842592.1, EFX04185.1, XP_003231449.1, XP_001729067.1, CBX94189.1, XP_001413535.1, ACF22878.1, B5WWZ9.1, XP_002994642.1, XP_002269629.1, XP_002519938.1, XP_002982582.1, NP_001047464.1, EEC73620.1, XP_002981110.1, XP_002960521.1, NP_566729.1, XP_001541970.1, XP_002967201.1, BAK00483.1, XP_002182547.1, BAK02336.1, XP_002454190.1, XP_002328753.1, XP_002867943.1, XP_002285334.1, CAC87643.1, CAN71289.1, XP_002454188.1, AAL31049.1, XP_002464494.1, AAL31021.1, YP_117187.1, XP_002543430.1, CAA18625.1, XP_002883430.1, NP_193673.2, XP_002529832.1, XP_001753124.1, NP_001142399.1, ACN27562.1, XP_002464495.1, ACR36691.1, BAJ86655.1, B5WWZ8.1, NP_001148058.1, ABR17814.1, EAY78905.1, NP_194586.1, AAM63097.1, AAK64154.1, NP_001064839.2, XP_002869492.1, XP_002314488.1, AAL31024.1, ZP_06967355.1, AAP54248.2, XP_002311685.1, ACF87929.1, YP_907078.1, EGE07035.1, YP_001849908.1, XP_002464496.1, EEC67160.1, AAL31027.1, XP_001761391.1, XP_002961172.1, XP_002528823.1, XP_002966834.1, NP_001176205.1, XP_001763007.1, XP_002272123.1, XP_002889487.1, XP_003003157.1, NP_285451.1, EGG23219.1, NP_171895.2, YP_003395677.1, Q9ZWB9.1, ACF88407.1, XP_06413771.1, EEE51131.1, YP_003835264.1, YP_003397164.1, YP_004081922.1, XP_003294587.1, EEE51130.1, YP_003647529.1, YP_003647985.1, CBI29206.3, XP_629786.1,

ZP_07964664.1, EEE57396.1, EEH09589.1, YP_003265796.1, YP_001840752.1, ZP_08620775.1, ACR36076.1, ZP_05043749.1, YP_980677.1, ZP_05043728.1, YP_692894.1, NP_710223.1, EEC67159.1, AAP03110.1, EFA85697.1, YP_691805.1, YP_551012.1, YP_001174466.1, YP_002796294.1, YP_004716331.1, YP_001019547.1, YP_585737.1, AEA86007.1, YP_960830.1, YP_004743970.1, ZP_03431349.1, ZP_06448642.1, ZP_07430351.1, NP_215006.2, ZP_03535393.1, ZP_06801690.1, YP_001849132.1, NP_854165.1, ZP_03427234.1, CBJ27378.1, NP_334920.1, ZP_08571383.1, YP_728161.1, ZP_01896040.1, ZP_03530923.1, YP_551306.1, YP_003167456.1, YP_606070.1, ZP_06850167.1, ADP99095.1, YP_907986.1, ZP_04924166.1, ZP_08139923.1, YP_001270300.1, YP_521830.1, YP_003147410.1, YP_002007173.1, ADR62464.1, YP_004382294.1, NP_747223.1, YP_004687462.1, NP_902159.1, ZP_04936784.1, YP_003914667.1, ZP_01306356.1, ZP_04750553.1, YP_002875279.1, YP_004704374.1, YP_001671392.1, NP_249055.1, ZP_06876360.1, YP_001345853.1, YP_002437969.1, YP_004356853.1, YP_351075.1, CBI23676.3, YP_001189668.1, YP_001528881.1, YP_001613612.1, YP_001747218.1, YP_003393002.1, YP_001365074.1, ZP_07778129.1, ZP_07392715.1, YP_001553329.1, YP_262925.1, YP_751961.1, YP_564183.1, YP_003811876.1, YP_002356821.1, YP_001051828.1, YP_001837525.1, NP_716513.1, ZP_01915079.1, ZP_02156621.1, YP_001184631.1, YP_001475595.1, ZP_05042393.1, YP_962228.1, YP_001612275.1, ADV55625.1, YP_001675797.1, YP_003555260.1, ZP_01075039.1, YP_003812822.1, YP_001503351.1, EFN52938.1, YP_001759063.1, ZP_06503577.1, YP_871025.1, ZP_08564919.1, YP_002310162.1, YP_732875.1, YP_001092722.1, YP_739324.1, XP_002333995.1, NP_085596.1, YP_928870.1, EGD05748.1, NP_443993.1, ZP_08138057.1, ZP_05041587.1, ZP_07011380.1, YP_001612684.1, ZP_07669342.1, ZP_06508361.1, ZP_03423639.1, YP_923293.1, ZP_05061865.1, ZP_08181496.1, YP_559605.1, ZP_06841320.1, ZP_01620712.1, YP_001896340.1, ZP_03276650.1, YP_004303194.1, ZP_08180715.1, ZP_06382740.1, ZP_01034555.1, YP_004604560.1, YP_001020142.1, YP_935375.1, ZP_01546137.1, ZP_07661079.1, YP_001860640.1, ZP_06052841.1, ZP_01881170.1, ZP_05781455.1, YP_932732.1, ZP_08119300.1, YP_004715268.1, ZP_03697402.1, YP_004126957.1, ZP_06703136.1, NP_642445.1, ZP_08273900.1, YP_004524313.1, ZP_01902993.1, YP_001900094.1, AEA84888.1, YP_004690289.1, NP_714358.1, YP_682471.1, YP_003239.1, YP_997465.1, YP_003452130.1, ZP_01739153.1, YP_004219483.1, YP_001761298.1, ZP_01438251.1, CBI37146.3, ZP_04748383.1, YP_004362245.1, ZP_05912795.1, YP_003390234.1, YP_003122799.1, CCB77579.1, EGB06416.1, ZP_08389346.1, YP_191496.1, ZP_05224727.1, ZP_01125614.1, YP_466287.1, YP_001368620.1, YP_001380256.1, YP_002361951.1, YP_002756103.1, YP_001801399.1, ZP_06847140.1, YP_003200069.1, YP_001940247.1, YP_001584322.1, ZP_04679227.1, YP_002493674.1, YP_002135530.1, YP_004290424.1, YP_001772011.1, ZP_08190046.1, ZP_03423640.1, YP_001834251.1, ZP_01041752.1, YP_001533410.1, YP_269751.1, YP_002432994.1, YP_003694653.1, CAD47896.1, NP_769359.1, YP_004239460.1, YP_004605221.1, YP_001961214.1, YP_001837513.1, YP_004335962.1, YP_004358600.1, ZP_05050026.1, YP_003202983.1, BAD03777.1, ZP_02165013.1, NP_774131.1, YP_432169.1, ZP_05000547.1, YP_001261233.1, XP_002593969.1, XP_002603265.1, YP_003342435.1, ZP_01253183.1, EGO36831.1, YP_001866737.1, YP_001523879.1, YP_133594.1, YP_003768990.1, YP_001237820.1, YP_003133224.1, ZP_01896771.1, ZP_01865125.1, NP_960319.1, YP_826958.1, YP_003326608.1, YP_002219515.1, NP_217926.1, ZP_07441899.2, YP_001208178.1, ADM42038.1, YP_002433510.1, ZP_08274313.1, EGO38668.1, ZP_03393221.1, NP_356358.1, ZP_06055780.1, YP_001684562.1, ZP_08528157.1, BAD03162.1, YP_001800712.1, ACL37106.1, YP_883489.1, ZP_01075202.1, NP_969446.1, ZP_01129577.1, YP_001530285.1, ZP_04746501.1, YP_001341980.1, YP_905003.1, ZP_05218299.1, and ZP_08665577.1.

In particular, the alcohol oxidase ($E_c$) may be selected from the group consisting of AAS46878.1, ACX81419.1, AAS46879.1, CAB75353.1, AAS46880.1, XP_712350.1, XP_002422236.1, XP_712386.1, EEQ43775.1, CAB75351.1, CAB75352.1, XP_002548766.1, and XP_0025487651.1.

Enzyme $E_{di}$

In particular, the AlkJ alcohol dehydrogenase ($E_{di}$), may be selected from the group consisting of:

Q00593.1, Q9WWW2.1, ZP_00957061.1, YP_957894.1, CAC38030.1, YP_694430.1, YP_957725.1, YP_001672216.1, YP_552061.1, YP_130410.1, ZP_06155535.1, ZP_01222730.1, YP_691907.1, YP_002297804.1, YP_004283522.1, YP_001234383.1, YP_004435031.1, ZP_05110316.1, ZP_05042898.1, YP_004466324.1, ZP_08553549.1, YP_004125220.1, ADI22536.1, ADI18461.1, YP_003810975.1, YP_662346.1, YP_004427557.1, YP_692606.1, ZP_05043291.1, YP_440752.1, ZP_02386160.1, ZP_04763547.1, YP_02361232.1, YP_003376674.1, ZP_02354055.1, ZP_05085930.1, ADQ00130.1, YP_003643016.1, ZP_05040520.1, YP_691922.1, AAX23098.1, BAD07371.1, NP_104379.1, YP_002551960.1, YP_003908558.1, YP_987903.1, ZP_05785860.1, YP_004145612.1, YP_004140926.1, CAZ88300.1, ZP_05041901.1, YP_533645.1, ZP_01754259.1, CBA31223.1, YP_587542.1, YP_106852.1, ZP_08402506.1, ZP_05055020.1, YP_02400829.1, YP_104747.1, ZP_02409412.1, YP_001057269.1, YP_004229837.1, YP_294429.1, YP_001028112.1, ZP_02479747.1, YP_002874799.1, ZP_03541051.1, YP_003606536.1, ZP_02887167.1, YP_001795572.1, YP_487451.1, ACZ62814.1, YP_560809.1, ZP_02167462.1, YP_004482869.1, YP_001581248.1, ZP_07374066.1, YP_001203981.1, ZP_06840259.1, ZP_01915145.1, NP_774525.1, ZP_03561080.1, YP_001208258.1, YP_001897374.1, YP_001413909.1, YP_366469.1, YP_521854.1, YP_004490642.1, YP_003280349.1, ZP_03588744.1, YP_001562229.1, YP_001120981.1, ZP_03574970.1, YP_004234225.1, ZP_02377531.1, ZP_02149954.1, YP_001237360.1, ZP_03266156.1, YP_782821.1, YP_004754039.1, BAB61732.1, ZP_07046388.1, ZP_02145452.1, BAF45123.1, YP_002129953.1, YP_003812439.1, ZP_01055291.1, BAF45124.1, EGH71399.1, ZP_05060389.1, YP_005090872.1, BAF45126.1, BAB07804.1, ZP_06053464.1, YP_001238278.1, ZP_04944469.1, YP_001171160.1,

YP_002984373.1, YP_002237649.1, ZP_08276443.1, YP_001241858.1, NP_104253.1, YP_676241.1,
BAF98451.1, ZP_05124197.1, YP_568640.1, ZP_01736903.1, ZP_00960121.1, NP_436019.1,
ZP_05785341.1, NP_769037.1, YP_370657.1, YP_002945716.1, YP_259594.1, EFV86615.1,
YP_775005.1, ZP_02911119.1, YP_165460.1, AAY87334.1, NP_900970.1, AEG07409.1, YP_349087.1,
ZP_02891796.1, YP_622328.1, ZP_07675057.1, YP_004141055.1, YP_001169476.1, YP_001566960.1,
YP_001901188.1, YP_003592183.1, ZP_02361040.1, YP_260472.1, ZP_07028078.1, YP_004610468.1,
NP_518244.1, YP_001809673.1, NP_947032.1, YP_003066461.1, YP_961096.1, ZP_08666573.1,
YP_001766369.1, YP_002255997.1, ZP_04940241.1, ZP_02187363.1, YP_001631518.1, ZP_08141293.1,
YP_004012032.1, YP_841049.1, YP_002983249.1, YP_001666324.1, NP_387083.1, YP_001526184.1,
YP_003643276.1, YP_003855487.1, YP_003778137.1, YP_165213.1, YP_003694923.1, YP_004433897.1,
ZP_02361104.1, CBA30511.1, ZP_05781295.1, YP_001265431.1, ZP_05068964.1, YP_002313077.1,
YP_756865.1, ZP_02461782.1, YP_002007988.1, ZP_02372305.1, YP_004486039.1, YP_341901.1,
YP_004110133.1, YP_002229680.1, ZP_02386040.1, YP_001862312.1, YP_004681983.1, YP_617373.1,
YP_004684069.1, YP_373268.1, YP_440614.1, EFV86570.1, YP_001673285.1, BAK39604.1,
NP_421441.1, YP_264896.1, YP_004362617.1, YP_001669327.1, YP_004353150.1, YP_001888124.1,
ZP_06053847.1, YP_366538.1, YP_003812285.1, ZP_08645365.1, YP_003410784.1, YP_841363.1,
YP_004154520.1, ZP_01901081.1, ZP_02372179.1, EGP44033.1, YP_001633470.1, EGP42855.1,
ZP_02453559.1, ADP98564.1, YP_003747084.1, ZP_01115125.1, ADR57794.1, YP_784649.1,
ZP_02487888.1, ZP_01768075.1, ZP_02400664.1, YP_373898.1, Q47944.1, YP_001117950.1,
YP_106680.1, YP_724753.1, YP_002907583.1, ZP_02380339.1, ZP_03697092.1, YP_003187112.1,
YP_004482470.1, YP_167582.1, YP_270109.1, YP_004065439.1, NP_742226.1, YP_002429878.1,
YP_004362333.1, ZP_02504034.1, YP_003189363.1, YP_003556403.1, AEH81535.1, YP_001887935.1,
YP_973212.1, ZP_00952746.1, YP_459665.1, YP_554605.1, ZP_07333059.1, YP_001991668.1,
YP_777218.1, YP_581107.1, YP_01878091.1, YP_003694210.1, YP_222680.1, YP_002232672.1,
ZP_01057973.1, YP_002913124.1, ZP_01035570.1, YP_001763402.1, YP_001806802.1, YP_662156.1,
YP_001777560.1, YP_552627.1, ZP_02890876.1, ZP_05153429.1, ZP_01893457.1, ZP_04595387.1,
YP_587146.1, YP_004141814.1, YP_001685369.1, ADP99389.1, ZP_02890074.1, YP_001313582.1,
ZP_05343380.1, NP_886000.1, ZP_04942359.1, NP_387401.1, ZP_01863693.1, YP_750630.1,
ZP_01913732.1, ZP_08244266.1, YP_002233254.1, ZP_04939997.1, YP_268077.1, ZP_05169265.1,
ZP_01816670.1, YP_837233.1, ZP_07478008.1, NP_888994.1, ZP_08408421.1, YP_001155137.1,
ZP_01985205.1, ZP_07473972.1, ZP_01067090.1, NP_699017.1, YP_002008190.1, YP_004493716.1,
ZP_01867788.1, ZP_01754024.1, EGM19144.1, YP_266277.1, YP_004654190.1, YP_943422.1,
ZP_07741283.1, ZP_06876839.1, YP_002395287.1, ZP_05162503.1, ZP_02905080.1, ZP_02905080.1,
ZP_07795498.1, NP_102692.1, NP_252789.1, ZP_03784461.1, YP_001601784.1, YP_002233786.1,
YP_004451100.1, ZP_01305514.1, YP_002438481.1, YP_622842.1, YP_002822679.1, ZP_04944312.1,
ZP_04930310.1, YP_001810189.1, YP_104187.1, ZP_05179897.1, YP_004483124.1, YP_003390414.1,
ZP_01367534.1, YP_001346382.1, ZP_01878466.1, YP_771968.1, YP_001628465.1, YP_004311599.1,
YP_789017.1, YP_001115422.1, ZP_05067451.1, ZP_01037150.1, ZP_01611812.1, ZP_03575238.1,
ZP_05842072.1, YP_001682976.1, YP_761348.1, YP_002278603.1, YP_001593845.1, EGD01613.1,
YP_004611600.1, YP_004188241.1, NP_419761.1, YP_297574.1, YP_367509.1, YP_998315.1,
EFV85163.1, YP_684227.1, ZP_06177455.1, ZP_08664883.1, ZP_05114787.1, ZP_05450190.1,
NP_935088.1, YP_004614491.1, ZP_08697916.1, YP_298028.1, ZP_01034678.1, YP_002827796.1,
YP_004689366.1, ZP_05052326.1, YP_267420.1, YP_372762.1, YP_004466723.1, ZP_01012072.1,
YP_728575.1, YP_001759584.1, YP_557446.1, YP_320380.1, ZP_01075202.1, YP_001312358.1,
ZP_06844897.1, YP_06079799.1, YP_003771143.1, YP_681895.1, ZP_07718189.1, EGP55868.1,
ZP_05094472.1, YP_511622.1, ACF98205.1, YP_003750799.1, YP_002984725.1, YP_002543360.1,
YP_582314.1, ZP_07660450.1, YP_004065269.1, ZP_01040714.1, ZP_04717111.1, YP_002422932.1,
YP_003979606.1, YP_002520401.1, YP_003579281.1, YP_003506115.1, ZP_01444019.1, ZP_03587285.1,
ZP_01749397.1, ZP_03265018.1, ZP_07283393.1, YP_771439.1, YP_001947593.1, YP_001049712.1,
YP_001532150.1, YP_298941.1, ZP_06688181.1, YP_003979888.1, YP_001553786.1, YP_003980878.1,
ZP_01611660.1, ZP_02367747.1, EGP42870.1, YP_001578274.1, YP_472442.1, YP_778292.1,
ZP_00993245.1, ABY65992.1, YP_354800.1, EGE56670.1, YP_002779312.1, YP_432169.1,
ZP_01747277.1, YP_561728.1, ZP_02190947.1, YP_560963.1, YP_001265285.1, YP_002822699.1,
YP_605824.1, YP_001991873.1, ZP_00955792.1, YP_002278091.1, ZP_08632361.1, YP_002229178.1,
YP_003594401.1, YP_004156101.1, YP_001472858.1, ZP_06840392.1, ZP_05069105.1, ZP_00998644.1,
YP_1, 001746950 ZP_08410042.1, ZP_01116604.1, YP_004487901.1, YP_680905.1, YP_728088.1,
ADP99912.1, ZP_01692203.1, YP_001328534.1, YP_001985833.1, YP_002007099.1, ZP_05066777.1,
YP_999236.1, YP_002278452.1, YP_01306234.1, ZP_01551182.1, YP_002973332.1, ZP_04681414.1,
YP_002871776.1, ZP_02369920.1, YP_01896942.1, ZP_07675148.1, AEH83964.1, YP_004692042.1,
YP_002289724.1, AEG07584.1, YP_999005.1, CBJ36337.1, EGP48473.1, ZP_03585612.1,
YP_003552461.1, YP_270668.1, ZP_06862917.1, YP_001369428.1, YP_001897527.1, AEG08472.1,
YP_001811327.1, YP_001166036.1, ABW06653.1, YP_001166065.1, NP_437018.1, NP_294689.1,
ZP_01548976.1, ZP_07774606.1, ZP_05888080.1, YP_002541437.1, YP_004692953.1, NP_107484.1,
YP_003301477.1, YP_341748.1, YP_05100248.1, YP_995681.1, YP_765267.1, YP_166223.1,
YP_918038.1, YP_001500869.1, YP_004305296.1, ZP_01740635.1, YP_001234127.1, YP_02186681.1,
YP_003342584.1, NP_947961.1, ZP_05124765.1, YP_004140839.1, YP_001584499.1, ADI17244.1,
ZP_01904700.1, YP_003696207.1, YP_004156699.1, ZP_08698744.1, YP_001022991.1, EFV84582.1,

ZP_01743515.1, YP_001816113.1, YP_004688050.1, ZP_02492080.1, ZP_04901176.1, ZP_06915396.1, YP_001342912.1, ZP_01125614.1, EGD05029.1, ZP_07474845.1, ZP_07477743.1, YP_004152647.1, ZP_03569823.1, ZP_05089337.1, YP_001901091.1, YP_004755056.1, ZP_05086419.1, YP_004577547.1, NP_886663.1, ZP_07718907.1, YP_004687387.1, ACD99850.1, YP_980426.1, ZP_05457072.1, NP_521464.1, ZP_06688394.1, ZP_08099738.1, ZP_05936041.1, NP_700124.1, ADT85599.1, ZP_02885452.1, YP_003744085.1, YP_001328823.1, YP_110012.1, ZP_05076113.1, YP_001068288.1, ZP_02488044.1, ZP_01015005.1, YP_002983153.1, ZP_02457871.1, ZP_01014169.1, EGE60620.1, ZP_06898725.1, ZP_05886707.1, ZP_08101209.1, YP_001346810.1, YP_003408795.1, YP_003769675.1, ZP_03319462.1, YP_003134969.1, YP_001188857.1, YP_001257876.1, EGH93583.1, ZP_01442222.1, YP_004557767.1, YP_004675666.1, YP_004358728.1, YP_331617.1, ZP_05636703.1, YP_001594896.1, YP_002252541.1, YP_684009.1, ZP_05085667.1, YP_002822967.1, YP_118823.1, ZP_01878717.1, ZP_02144674.1, YP_004127560.1, ZP_01901604.1, ZP_07375284.1, YP_001371250.1, ZP_07658682.1, YP_004280074.1, AEG67402.1, YP_001416516.1, YP_002898825.1, ZP_01547199.1, YP_223070.1, ZP_01054720.1, ZP_08197897.1, NP_107235.1, ZP_05161482.1, ZP_04679742.1, YP_002778618.1, YP_002909966.1, ZP_01545876.1, ZP_02147729.1, ZP_01626756.1, ZP_05101564.1, YP_002947374.1, ZP_00946537.1, ZP_01903844.1, ZP_05085589.1, NP_385053.1, YP_001328117.1, YP_004493948.1, ACV84069.1, YP_367172.1, ZP_02165272.1, YP_003339515.1, YP_004699488.1, ZP_05101969.1, YP_701696.1, ZP_04935724.1, ZP_02191362.1, YP_485352.1, ZP_01746033.1, ZP_06712293.1, ZP_01740154.1, ZP_07662819.1, NP_103908.1, ZP_01158125.1, ZP_01058616.1, ZP_05739755.1, YP_003159313.1, YP_003197010.1, ZP_02152342.1, NP_949067.1, ZP_02364657.1, YP_570690.1, YP_001907189.1, YP_004387414.1, YP_001413869.1, YP_001208663.1, ZP_02357557.1, ZP_04751682.1, ZP_01916549.1, ZP_03264661.1, AAY82840.1, YP_001326253.1, YP_487666.1, ZP_05167919.1, YP_003277969.1, YP_767433.1, ZP_01226234.1, ADI18237.1, YP_002825245.1, ZP_02144858.1, EGE55950.1, NP_882474.1, ZP_04680938.1, ZP_02188790.1, YP_06794586.1, YP_001809828.1, YP_004417965.1, ZP_01367142.1, EGM13684.1, YP_997974.1, YP_001476791.1, ZP_08635286.1, YP_001262083.1, ZP_01881606.1, ZP_01002680.1, YP_676287.1, ZP_07308228.1, ZP_04596242.1, YP_003606679.1, YP_001868359.1, ZP_01446736.1, YP_001622726.1, NP_699590.1, ZP_01446884.1, YP_004141411.1, YP_002438878.1, YP_002500414.1, YP_001168504.1, ZP_01616388.1, ZP_05117189.1, EGP55675.1, ZP_08405873.1, YP_002975318.1, ZP_05876432.1, ADT64694.1, ZP_01754911.1, YP_002823637.1, ZP_02188786.1, YP_004617386.1, ZP_05880498.1, ZP_02360829.1, ZP_06052433.1, ABL61001.1, YP_004190679.1, YP_004418710.1, ZP_08663540.1, YP_003768966.1, ZP_02165422.1, YP_001264994.1, NP_252399.1, ACA21517.1, ZP_00960985.1, ZP_07026655.1, YP_001753039.1, YP_002541208.1, YP_001369943.1, YP_789454.1, YP_371288.1, YP_002974725.1, YP_776880.1, YP_004688060.1, YP_611623.1, ZP_07795086.1, ZP_05784963.1, ZP_05124380.1, YP_459030.1, ZP_04929943.1, YP_004444316.1, ZP_01866687.1, ZP_05090690.1, ZP_05064893.1, ZP_02367982.1, ZP_05973466.1, YP_004353327.1, ZP_05780591.1, ZP_01890564.1, NP_541848.1, ZP_00960263.1, ZP_05784784.1, NP_936564.1, ZP_05739211.1, ZP_02961617.1, YP_001242097.1, and ZP_05838258.1.

ZP_05113045.1, ZP_06689273.1, ZP_06972168.1,
ZP_01616404.1, ZP_07659253.1, ZP_05117914.1,
YP_585662.1, YP_004230016.1, NP_763554.1,
NP_744101.1, ZP_02465308.1, ACN56476.1,
YP_004689565.1, YP_001600608.1, ZP_06792595.1,
YP_001258553.1, ZP_05165722.1, ZP_03785098.1,
YP_002276744.1, YP_002524856.1, ADP98420.1,
YP_001669248.1, ZP_04764988.1, ZP_08528163.1,
ZP_08529409.1, ZP_05944625.1, YP_676267.1,
CBA26630.1, YP_001592413.1, YP_003486465.1,
ZP_02187562.1, ZP_03702891.1, YP_760283.1,
ZP_05450850.1, YP_004533595.1, ZP_02153313.1,
YP_001859265.1, YP_001524099.1, ZP_06126913.1,
ZP_07374926.1, ZP_05050787.1, ZP_01035411.1,
Q8YFY2.2, YP_002280903.1, EGM21512.1,
YP_004603010.1, ZP_05088581.1, YP_004302488.1,
YP_004141219.1, NP_697569.1, YP_003908705.1,
YP_915505.1, YP_001789228.1, YP_001042739.1,
YP_133405.1, ZP_05180516.1, ZP_05174702.1,
ZP_01438051.1, ZP_04590345.1, ZP_08411937.1,
NP_356519.2, ZP_00964019.1, ZP_00998343.1,
ZP_05181994.1, YP_004107969.1, ZP_02168070.1,
ZP_01750865.1, YP_574504.1, YP_004579902.1,
YP_104440.1, ZP_05452167.1, ZP_05342702.1,
YP_001862883.1, YP_004538242.1, ZP_07471513.1,
ZP_05169558.1, ZP_00956995.1, ZP_05096699.1,
YP_004916916.1, ZP_01218118.1, AAU95210.1,
ZP_02405087.1, ZP_04890639.1, YP_352237.1,
ZP_02413594.1, ZP_07474023.1, NP_541317.1,
YP_001993222.1, ZP_08199001.1, YP_471839.1,

In particular $E_{di}$ may be selected from the group consisting of Q00593.1, Q9WWW2.1, ZP_00957061.1, YP_957894.1, CAC38030.1, YP_694430.1, YP_957725.1, and YP_001672216.1.

Enzyme $E_{dii}$

The alcohol dehydrogenase ($E_{dii}$) may be selected from the group consisting of AdhE, AdhP, YjgB, YqhD, GldA, EutG, YiaY, AdhE, AdhP, YhhX, YahK, HdhA, HisD, SerA, Tdh, Ugd, Udg, Gmd, YefA, YbiC, YdfG, YeaU, TtuC, YeiQ, YgbJ, YgcU, YgcT, YgcV, YggP, YgjR, YliI, YqiB, YzzH, LdhA, GapA, Epd, Dld, GatD, Gcd, GlpA, GlpB, GlpC, GlpD, GpsA and YphC from bacteria, in particular *E. coli*.

Enzyme $E_3$

Enzyme $E_3$ may be capable of converting at least one 1-alkanal to the corresponding alkanoic acid. In particular, $E_3$ may be selected from the group consisting of P450 alkane hydroxylases ($E_a$) of EC 1.14.15.3-, AlkB alkane hydroxylases ($E_b$) of EC 1.14.15.3, bifunctional alcohol oxidases ($E_c$) of EC 1.1.3.20, bifunctional AlkJ alcohol dehydrogenases ($E_{dii}$) or bifunctional alcohol dehydrogenases ($E_{dii}$) of EC 1.1.1.1 or EC 1.1.1.2, capable of oxidizing an 1-alkanol via an 1-alkanal directly to the corresponding alkanoic acid and aldehyde dehydrogenases ($E_e$).

Enzyme $E_e$

Enzyme $E_e$, an aldehyde dehydrogenase, may be capable of catalyzing the conversion of ω-oxoalkanoic acid (ester)=ω-carboxyalkanoic acid (ester).

In order to catalyse the above reaction, $E_e$ may be an aldehyde dehydrogenase of EC 1.2.1.3, EC 1.2.1.4 or EC 1.2.1.5, a fatty alcohol oxidases of EC 1.1.3.20, AlkJ alcohol dehydrogenases of EC 1.1.99.- and alcohol dehydrogenases of EC 1.1.1.1 or EC 1.1.1.2

In one example, $E_e$ may be capable of specifically catalysing the following reaction:

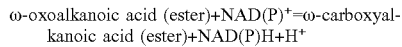
ω-oxoalkanoic acid (ester)+NAD(P)$^+$=ω-carboxyalkanoic acid (ester)+NAD(P)H+H$^+$ In this case, enzyme $E_e$ may be an aldehyde dehydrogenase of EC 1.2.1.3, EC 1.2.1.4 or EC 1.2.1.5, and may be selected from the group consisting of Prr, Usg, MhpF, AstD, GdhA, FrmA, Feab, Asd, Sad, PuuE, GabT, YgaW, BetB, PutA, PuuC, FeaB, AldA, Prr, EutA, GabD, AldB, TynA and YneI from bacteria, in particular *E. coli*.

In another example, enzyme $E_e$ may be capable of catalysing the following reaction:

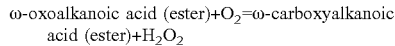
ω-oxoalkanoic acid (ester)+O$_2$=ω-carboxyalkanoic acid (ester)+H$_2$O$_2$ In this case, $E_e$ may be a fatty alcohol oxidases of EC 1.1.3.20 and may be selected from the list as provided as enzyme $E_c$ above.

In another example, $E_e$ may be at least one AlkJ alcohol dehydrogenase of EC 1.1.99 and may be selected from the list provided above as $E_{di}$.

In a further example, $E_e$ may be an alcohol dehydrogenases of EC 1.1.1.1 or EC 1.1.1.2 selected from the list provided as enzyme $E_{dii}$.

Enzyme $E_4$

Enzyme $E_4$ may be capable of converting at least one alkanoic acid to the corresponding alkanoic acid ester. In particular, $E_4$ may be at least one wax-ester synthase, also known as an alcohol O-acyl transferase (EC 2.3.1.20, EC 2.3.1.75) ($E_f$), or an alcohol O-acetyl transferase ($E_g$) (EC 2.3.1.20, EC 2.3.1.75 or EC 2.3.1.84).

In on example, $E_4$ may be at least one wax-ester synthase ($E_f$). More in particular, $E_4$ may comprise sequence identity of at least 50% to the *Acinetobacter calcoaceticus* ADP1, or O-acetyltransferase of *Hahella chejuensis*. Even more in particular, $E_4$ may comprise sequence identity of at least 50% to the polypeptide YP_045555.1, WP_011398768.1 or NP_808414.2. More in particular, $E_4$ may comprise a polypeptide with sequence identity of at least 50, 60, 65, 70, 75, 80, 85, 90, 91, 94, 95, 98 or 100% to a polypeptide selected from the group consisting of polypeptide YP_045555.1, WP_011398768.1 and NP_808414.2. In one example, $E_4$ may comprise a polypeptide with sequence identity of at least 50, 60, 65, 70, 75, 80, 85, 90, 91, 94, 95, 98 or 100% to SEQ ID NO:2.

Enzyme $E_f$

In particular, the Enzyme $E_f$, may be selected from the group consisting of:

WP_011398768.1, NP_808414.2, NP_001178653.1, XP_003272721.1, XP_002720111.1, NP_001002254.1, XP_529027.1, XP_002831804.1, BAC28882.1, XP_549056.2, XP_002918053.1, XP_001085075.1, XP_002763005.1, XP_002700092.1, XP_599558.4, EDL95940.1, XP_001496780.1, CAD89267.1, EFB28125.1, YP_004747160.1, YP_004746900.1, YP_004746665.1, YP_004746558.1, YP_004746531.1, YP_004746530.1, YP_004745948.1, YP_004745222.1, YP_004744358.1, YP_004743710.1, YP_002492297.1, AEK40846.1, YP_001847685.1, YP_001712672.1, YP_001706290.1, YP_004724737.1, YP_004723134.1, AEJ51098.1, AEJ48174.1, AEJ47480.1, YP_004392630.1, YP_004099725.1, YP_003912033.1, YP_003652731.1, YP_003301387.1, YP_003298139.1, YP_001509672.1, YP_001505948.1, YP_001432486.1, YP_001432432.1, YP_924893.1, YP_923981.1, YP_922869.1, YP_922597.1, YP_922419.1, ZP_08629145.1, ZP_08628906.1, YP_001380027.1, YP_001280731.1, YP_001280730.1, YP_888966.1, YP_890540.1, YP_888236.1, YP_888223.1, YP_888574.1, YP_884705.1, YP_889488.1, YP_886248.1, YP_882534.1, YP_881069.1, YP_881444.1, YP_883472.1, YP_879642.1, YP_884073.1, YP_880917.1, YP_882201.1, YP_879422.1, YP_707862.1, YP_707847.1, YP_707633.1, YP_707572.1, YP_707571.1, YP_706785.1, YP_706267.1, YP_705586.1, YP_705294.1, YP_702929.1, YP_701572.1, YP_700576.1, YP_700081.1, YP_700033.1, YP_700018.1, YP_700017.1, YP_699999.1, CCB78299.1, CCB78283.1, CCB72233.1, YP_004663601.1, YP_004525283.1, YP_004524901.1, YP_004524237.1, YP_004524223.1, YP_004523752.1, YP_004522677.1, YP_004521797.1, YP_004521441.1, YP_004020500.1, YP_004014348.1, EGO40684.1, EGO38684.1, EGO38655.1, EGO37244.1, EGO36970.1, EGO36701.1, YP_003951335.1, YP_003812176.1, YP_003811992.1, YP_003810691.1, YP_003810418.1, YP_003809501.1, ZP_08574204.1, CCA19760.1, XP_002900672.1, ZP_06414567.1, ZP_06413635.1, ZP_06411773.1, ZP_06411772.1, ZP_06271823.1, ZP_05620754.1, ZP_05360001.1, ZP_04752019.1, ZP_04751943.1, ZP_04750965.1, ZP_04750465.1, ZP_04750453.1, ZP_04750228.1, ZP_04750091.1, ZP_04749363.1, ZP_04749348.1, ZP_04749293.1, ZP_04749287.1, ZP_04749022.1, ZP_04748677.1, ZP_04747379.1, ZP_04747377.1, ZP_04747348.1, ZP_04747282.1, ZP_04747159.1, ZP_04747093.1, ZP_04746958.1, ZP_04717323.1, ZP_04684258.1, ZP_04386203.1, ZP_04385082.1, ZP_04384030.1, ZP_04384029.1, ZP_03534755.1, ZP_01115502.1, ZP_01102322.1, YP_004583872.1, YP_004583323.1, YP_004573656.1, YP_004571392.1, YP_003513699.1, ZP_08553011.1, ZP_08552672.1, YP_003467054.1, YP_003572597.1, YP_579515.1, YP_001136465.1, YP_001136231.1, YP_001135959.1, YP_001135349.1, YP_001133828.1, YP_001133806.1, YP_001133693.1, YP_001133270.1, YP_001132329.1, YP_001131721.1, YP_001131631.1, YP_001073715.1, YP_001073143.1, YP_001072388.1, YP_001072036.1, YP_001071893.1, YP_001071814.1, YP_001071689.1, YP_001070856.1, YP_001069682.1, YP_001069164.1, YP_001068496.1, YP_939377.1, YP_642242.1, YP_641664.1, YP_641419.1, YP_640919.1, YP_640783.1, YP_640704.1, YP_640572.1, YP_640571.1, YP_640494.1, YP_639709.1, YP_639198.1, YP_638523.1, YP_638030.1, YP_637968.1, YP_637380.1, YP_446603.1, NP_001185377.1, NP_200151.2, NP_568547.1, NP_197641.1, NP_200150.1, NP_197139.1, NP_190490.1, NP_190488.1, NP_177356.1, YP_004495408.1, YP_004495023.1, YP_004494197.1, YP_004494168.1, YP_004493973.1, YP_004493936.1, YP_004493628.1, YP_004493589.1, YP_004493509.1, YP_004493477.1, YP_004493462.1, YP_004492352.1, YP_004492155.1, YP_004492039.1, YP_004491716.1, YP_004491715.1, YP_004491501.1, YP_003375642.1, YP_003411203.1, YP_003410436.1, YP_003395271.1, YP_003395089.1, YP_003393635.1, YP_003384208.1, YP_003379551.1, ZP_04388235.1, YP_002134168.1, ZP_01900421.1, ZP_01900085.1, ZP_01899829.1, ZP_01898741.1, BAK05274.1, BAJ93623.1, BAJ97841.1, BAK08349.1, BAJ93204.1, BAJ92722.1, BAK06983.1, BAJ86545.1, BAK02325.1, BAJ85619.1, BAJ84892.1, ZP_05218281.1,

ZP_05218149.1, ZP_05217310.1, ZP_05216978.1, ZP_05216447.1, ZP_05216446.1, ZP_05216025.1, ZP_05214687.1, ZP_08476543.1, ZP_04749239.1, YP_823060.1, ADP99639.1, ADP98951.1, ADP98855.1, ADP98710.1, ADP96265.1, ZP_08461736.1, ZP_08461735.1, ZP_07608690.1, YP_045555.1, YP_872243.1, YP_004009106.1, YP_004008736.1, YP_004008003.1, YP_004007600.1, YP_004006799.1, YP_004006436.1, YP_004006072.1, YP_004005008.1, YP_003486913.1, NP_301898.1, ZP_08434757.1, YP_004079491.1, YP_004078785.1, YP_004077880.1, YP_004076486.1, YP_004076464.1, YP_004076350.1, YP_004075391.1, YP_004074864.1, ZP_01103855.1, YP_465274.1, ZP_08403393.1, ZP_08402717.1, ZP_08402716.1, YP_004427559.1, YP_001277083.1, YP_001276783.1, YP_524767.1, YP_522739.1, YP_521788.1, YP_004335162.1, YP_004333708.1, YP_004332973.1, YP_004332349.1, YP_004157731.1, YP_004224204.1, YP_003275673.1, YP_003275371.1, YP_003274979.1, YP_003274924.1, YP_003274705.1, YP_956544.1, YP_955502.1, YP_955007.1, YP_954887.1, YP_954886.1, YP_954859.1, YP_954399.1, YP_953715.1, YP_953073.1, YP_952592.1, YP_951909.1, YP_951298.1, YP_951083.1, ZP_08287899.1, ZP_08272356.1, ZP_08270967.1, CCA60099.1, CCA56737.1, YP_983728.1, YP_550833.1, YP_549124.1, YP_121795.1, YP_120815.1, YP_118589.1, YP_117783.1, YP_117375.1, YP_003646883.1, YP_003646055.1, YP_003645661.1, EGE49469.1, ZP_08234310.1, CBZ53121.1, YP_004010866.1, EGE24961.1, EGE18726.1, EGE15701.1, EGE12950.1, EGE10026.1, EGB03968.1, ZP_08206563.1, ZP_08205089.1, ZP_08204958.1, ZP_08204416.1, ZP_08203326.1, YP_714381.1, YP_713817.1, YP_694462.1, YP_693524.1, YP_003341775.1, YP_003339587.1, ZP_08197177.1, ADW01905.1, YP_004242683.1, ZP_07484742.2, ZP_07441979.2, ZP_07441978.2, ZP_07437333.2, ZP_06960424.1, ZP_06801236.1, ZP_06799517.1, ZP_05769718.1, ZP_05768326.1, ZP_05767970.1, ZP_05766272.1, ZP_05763839.1, YP_003204265.1, YP_003203570.1, YP_003200768.1, YP_003134884.1, YP_003134608.1, ZP_05140320.1, NP_001140997.1, EEE64643.1, EEE55448.1, EEE32548.1, ZP_03534776.1, ZP_03533653.1, ZP_03531929.1, EEC71274.1, EAY98969.1, EAY75974.1, EAY75973.1, ADZ24988.1, ZP_08157247.1, ZP_08156660.1, ZP_08156249.1, ZP_08153292.1, ZP_08152876.1, ZP_08152662.1, YP_002946672.1, YP_960669.1, YP_960629.1, YP_960328.1, YP_958134.1, YP_957462.1, YP_001022272.1, ZP_08123690.1, ZP_08120547.1, ZP_08119498.1, EGB29195.1, EGB27143.1, YP_003770089.1, YP_003769971.1, YP_003764703.1, YP_003764513.1, YP_003103950.1, YP_003168536.1, YP_003168331.1, YP_003166844.1, CAJ88696.1, NP_769520.1, YP_001141853.1, YP_001108534.1, YP_001106516.1, YP_907824.1, YP_907344.1, YP_906945.1, YP_906856.1, YP_906855.1, YP_906831.1, YP_906494.1, YP_906243.1, YP_905962.1, YP_905765.1, YP_905343.1, YP_905239.1, YP_325796.1, YP_130413.1, NP_625255.1, NP_624462.1, NP_338129.1, NP_338004.1, NP_337859.1, NP_337740.1, NP_337694.1, NP_336266.1, NP_335919.1, NP_335351.1, NP_334638.1, NP_218257.1, NP_218251.1, NP_217997.1, NP_217888.1, NP_217751.1, NP_217750.1, NP_217646.1, NP_217604.1, NP_217603.1, NP_217000.1, NP_216801.1, NP_216276.1, NP_215941.1, NP_215410.1, NP_214735.1, ZP_04661667.1, EFW44815.1, EFW44455.1, ZP_08024634.1, ZP_08024620.1, ZP_08023777.1, ZP_08023597.1, YP_002784032.1, YP_002783585.1, YP_002782904.1, YP_002782647.1, YP_002780099.1, YP_002779887.1, YP_002778497.1, YP_002777657.1, YP_002777402.1, ZP_07966321.1, ZP_07944768.1, CBI21867.3, CBI40547.3, CBI40544.3, CBI40540.3, CBI40536.3, CBI40534.3, CBI40533.3, CBI32385.3, ZP_05765756.1, ZP_05765643.1, ZP_05765597.1, ZP_05765596.1, YP_001705267.1, YP_001704692.1, YP_001704281.1, YP_001702654.1, YP_001701260.1, ZP_05770434.1, ZP_05766274.1, ZP_05762133.1, ZP_05762130.1, ZP_01101223.1, YP_481580.1, YP_979623.1, YP_979196.1, ZP_07414300.2, ZP_03537340.1, ZP_03537339.1, ZP_03536772.1, ZP_03536404.1, ZP_03433478.1, ZP_03430367.1, ZP_03430260.1, ZP_03429345.1, ZP_03428583.1, ZP_03426905.1, ZP_03426458.1, ZP_03426456.1, ZP_03426455.1, ZP_03425014.1, ZP_03424082.1, ZP_03421649.1, ZP_03419291.1, ZP_03418394.1, ZP_03417976.1, ZP_03414875.1, ZP_06952098.1, ZP_05528769.1, ZP_05527907.1, ZP_05227984.1, ZP_05227897.1, ZP_05227653.1, ZP_05227585.1, ZP_05227420.1, ZP_05227202.1, ZP_05226387.1, ZP_05226386.1, ZP_05225355.1, ZP_05225200.1, ZP_05223431.1, ZP_05223402.1, ZP_04697793.1, ZP_02550609.1, ZP_02548969.1, EEE25493.1, ABO13188.2 ZP_07205208.1, YP_589436.1, BAJ33896.1, ZP_07718107.1, ZP_07717513.1, ZP_07717390.1, ZP_07716424.1, ZP_04384387.1, ZP_07376578.1, ZP_06871097.1, ZP_06852444.1, ZP_06852442.1, ZP_06852283.1, ZP_06852150.1, ZP_06852032.1, ZP_06850980.1, ZP_06850766.1, ZP_06850644.1, ZP_06849846.1, ZP_06849446.1, ZP_06849265.1, ZP_06848894.1, ZP_06848550.1, ZP_06847321.1, ZP_06847245.1, ZP_06728640.1, ZP_06155537.1, ZP_03822106.1, ZP_03822105.1, ZP_03264909.1, ZP_01915979.1, ZP_01914209.1, ZP_01909198.1, ZP_01895985.1, ZP_01893763.1, ZP_01893601.1, ZP_01893547.1, ZP_01864269.1, ZP_01736818.1, ZP_01693481.1, ZP_01626518.1, ZP_01616172.1, ZP_01461648.1, ZP_01439861.1, ZP_01311414.1, ZP_01222733.1, ZP_01308993.1, ZP_00997001.1, ZP_06533596.1, YP_07308012.1, YP_07282351.1, ZP_07282257.1, ZP_07278697.1, ZP_07277986.1, ZP_07277799.1, ZP_07011797.1, ZP_06913634.1, ZP_06711075.1, ZP_06575037.1, ZP_06523715.1, ZP_06522644.1, ZP_06520408.1, ZP_06518751.1, ZP_06514733.1, ZP_06511304.1, ZP_06510466.1, ZP_06509700.1, ZP_06504004.1, ZP_06452618.1, ZP_06451687.1, ZP_06450049.1, ZP_06444722.1, ZP_06443996.1, ZP_06443677.1, ZP_06438510.1, ZP_06435077.1, ZP_06434554.1, ZP_06432969.1, ZP_06431341.1, ZP_06430915.1, ZP_05129423.1, ZP_05127637.1, ZP_05126217.1, ZP_05096686.1, ZP_05095013.1, ZP_05094400.1, ZP_05093434.1, ZP_05043539.1, ZP_05041631.1, ZP_04959394.1, ZP_04956551.1, ZP_01052702.1, YP_437020.1, YP_436128.1, YP_432512.1, YP_432391.1, ZP_06072118.1, ZP_06069021.1, ZP_06065092.1, ZP_06062254.1, YP_003032200.1, YP_003030813.1, YP_002766854.1, YP_002766842.1, YP_002766292.1, YP_002765623.1, YP_002765076.1, YP_002764977.1, YP_002764701.1, YP_002764693.1, YP_002764633.1, YP_002646976.1, YP_002646304.1, YP_001853537.1, YP_002646305.1, YP_002646304.1, YP_001853537.1, YP_001853530.1, YP_001853214.1, YP_001852100.1, YP_001851711.1, YP_001851686.1, YP_001851684.1, YP_001851611.1, YP_001851610.1, YP_001851579.1,

YP_001850950.1, YP_001850935.1, YP_001850900.1, YP_001850899.1, YP_001850378.1, YP_001849911.1, YP_001849825.1, YP_001849624.1, YP_001849470.1, YP_001848848.1, YP_001848784.1, YP_001822237.1, YP_001289190.1, YP_001289078.1, YP_001288434.1, YP_001287727.1, YP_001286168.1, YP_001085790.1, YP_856793.1, YP_629387.1, YP_615587.1, YP_615252.1, YP_457389.1, YP_263530.1, NP_962591.1, NP_962411.1, NP_962281.1, NP_961234.1, NP_960903.1, NP_960387.1, NP_960090.1, NP_959281.1, NP_959065.1, NP_857403.1, NP_857149.1, NP_857148.1, NP_857047.1, NP_856907.1, NP_856759.1, NP_856156.1, NP_855443.1, NP_855112.1, NP_853892.1, NP_828432.1, NP_603766.1, XP_003081224.1, YP_003778608.1, YP_003730939.1, XP_003059244.1, ADI13131.1, XP_002992800.1, XP_002963877.1, XP_001419779.1, XP_002988280.1, XP_002987493.1, CBH32551.1, CBH32550.1, CBH19575.1, CBH19574.1, YP_003627553.1, XP_002879777.1, XP_002877657.1, XP_002877655.1, XP_002873570.1, XP_002871716.1, XP_002870738.1, XP_002868506.1, XP_002865972.1, XP_002864239.1, XP_002862308.1, ZP_05823139.1, NP_001043877.1, ZP_06693274.1, ZP_06058985.1, NP_001044374.1, XP_002835451.1, XP_002787542.1, XP_002785958.1, XP_002785645.1, XP_002783220.1, XP_002774061.1, XP_002767852.1, XP_002766051.1, XP_002765456.1, XP_002765455.1, XP_002677788.1, XP_002671612.1, XP_002736281.1, CBA31373.1, XP_002184474.1, XP_002325936.1, XP_002323705.1, XP_002325937.1, XP_002323911.1, XP_002323706.1, XP_002328965.1, XP_002318416.1, XP_002310400.1, ACY38597.1, ACY38596.1, ACY38595.1, ACY38594.1, ACY38593.1, ACY38592.1, ACY38591.1, ACY38590.1, ACX81315.1, ACX81314.1, XP_001868729.1, XP_001847517.1, XP_001847515.1, XP_002502575.1, ACU20370.1, ACU18073.1, XP_002523348.1, XP_002516707.1, XP_002429016.1, BAH89673.1, XP_002440221.1, XP_002459294.1, XP_002458560.1, XP_320167.4, XP_001780431.1, XP_002364905.1, XP_002263196.1, XP_002263137.1, XP_002263409.1, XP_002263252.1, XP_002268615.1, XP_002278404.1, XP_002274522.1, XP_002282418.1, XP_001633379.1, XP_001632267.1, XP_001632004.1, XP_001622638.1, XP_002155609.1, XP_759225.1, XP_002152406.1, XP_001914471.1, XP_001738032.1, XP_001731626.1, XP_001209859.1, CAN79451.1, CAN78449.1, CAN72806.1, CAN71951.1, CAN71950.1, CAN76656.1, CAN62907.1, AAZ08051.1, ABO21022.1, ABO21021.1, ABO21020.1, ABJ96321.1, BAF01088.1, XP_758106.1, BAC42871.1, BAB09801.1 and BAB09102.1.

In another example, the Enzyme $E_f$, may be selected from the group consisting of the following NCBI gene identifiers: 6647910, 13882037, 13883719, 50084045, 83635736, 118163591, 118569740, 118570272, 119538589, 119959533, 126237252, 126567232, 126629771, 148572721, 148572722, 149823553, 149825234, 169147806, 196196001, 214037899, 219677786, 257447091, 262316603, 283813570, 301796553, 301796826, 311312714, 311696766, 325556018, 332970561, 333482117, 333482229, 333482837, 333484048, 334890574, 334890744, 353189260, 358244577, 359308666, 359732244, 359818908, 363993190, 365814880, 374845325, 377531673, 378802538, 384523048, 391857871, 391858262, 391861199, 396932954, 396935129, 399235093, 400203587, 407372801, 407812577, 432156225, 433296179, 442581482, 443888426, 444755700, 449424446, 464803513, 479864102, 479886236, 479966651, 480005669, 480024154, 480028610, 490485999, 498274456, 500625946, 515076064, 516264416, 516277644, 516906883, 516908681, 516909557, 516913828, 516945324, 517143888, 517432433, 517516200, 518350146, 518501601, 518568414, 518644062, 518944419, 518947555, 521014811, 521056034, 521076792, 521077398, 521090665, 521712969, 521812448, 521986522, 522129827, 522136843, 522139413 and 522139737.

Enzyme $E_g$

In particular, the Enzyme $E_g$, may be selected from the group consisting of EGA72844.1, NP_015022.1, S69991, AAP72991.1, EDN63695.1, BAA05552.1, AAP72992.1, S69992, AAP72995.1, XP_002552712.1, XP_001646876.1, XP_002551954.1, EGA82692.1, EDN61766.1, EGA86689.1, EGA74966.1, AAU09735.1, NP_011693.1, XP_445666.1, BAA13067.1, AAP72993.1, EGA62172.1, XP_455762.1, and EGA58658.1.

Enzyme $E_5$

Enzyme $E_5$ may be capable of converting at least one alkanoic acid ester of to the corresponding ω-hydroxy-alkanoic acid ester. In particular, $E_5$ may be any enzyme listed as $E_1$. In particular, $E_5$ may be at least one P450 alkane hydroxylase ($E_a$) of EC 1.14.15.3 or AlkB alkane hydroxylase ($E_b$) of EC 1.14.15.3.

Enzyme $E_6$

Enzyme $E_6$ may be capable of converting at least one ω-hydroxy-alkanoic acid ester to the corresponding ω-oxo alkanoic acid ester. In particular, $E_6$ may be any enzyme listed as $E_2$. In particular, $E_6$ may be selected from the group consisting of P450 alkane hydroxylases ($E_a$) of EC 1.14.15.3-, AlkB alkane hydroxylases ($B_b$) of EC 1.14.15.3, alcohol oxidases ($E_c$) of EC 1.1.3.20 and alcohol dehydrogenases ($E_d$) of EC 1.1.1.1 or EC 1.1.1.2.

The phrase 'when present' used in relation to Enzyme $E_6$, refers to cells that have been genetically modified to produce ω-oxo alkanoic acid ester. The cells according to any aspect of the present invention may comprise an increased expression of Enzyme $E_6$ relative to the wild type cell thus being able to produce ω-oxo alkanoic acid ester. In another example, the cells according to any aspect of the present invention may also comprise no increased expression of Enzyme $E_6$ relative to the wild type cell thus not being able to produce ω-oxo alkanoic acid ester. These cells may thus mainly produce ω-hydroxy-alkanoic acid ester. Therefore, when the cell according to any aspect of the present invention comprises increased expression of Enzyme $E_6$ (i.e. when present) then ω-oxo alkanoic acid ester may be produced.

Enzyme $E_7$

Enzyme $E_7$ may be capable of converting at least one ω-oxo alkanoic acid to the corresponding ω-amino alkanoic acid ester. In particular, $E_7$ may be an ω-transaminase of EC 2.6.1 ($E_h$).

In particular, the Enzyme $E_7$, may be an aminotransferase ($E_h$) selected from the group consisting of Pseudomonas putida (WP_016502144; WP_016500675.1), Chromobacterium violaceum (NP_901695.1), Rhodobacter sphaeroides 2.4.1 (YP_353455.1) and 3HMU_A, AAD41041.1, AAK15486.1, ABE03917.1, ADR60699.1, ADR61066.1, ADR62525.1, AEL07495.1, CAZ86955.1, EFW82310.1, EFW87681.1, EGC99983.1, EGD03176.1, EGE58369.1, EGH06681.1, EGH08331.1, EGH24301.1, EGH32343.1, EGH46412.1, EGH55033.1, EGH62152.1, EGH67339.1, EGH70821.1, EGH71404.1, EGH78772.1, EGH85312.1, EGH97105.1, EGP57596.1, NP_102850.1, NP_106560.1, NP_248912.1, NP_248990.1, NP_354026.2, NP_421926.1, NP_637699.1, NP_642792.1, NP_744329.1, NP_744732.1, NP_747283.1, NP_795039.1, XP_002943905.1, YP_001021095.1, YP_001059677.1, YP_001061726.1, YP_001066961.1, YP_001074671.1, YP_001120907.1, YP_001140117.1, YP_001170616.1, YP_001185848.1, YP_001188121.1, YP_001233688.1, YP_001268866.1, YP_001270391.1, YP_001345703.1, YP_001412573.1, YP_001417624.1, YP_001526058.1, YP_001579295.1, YP_001581170.1, YP_001668026.1, YP_001669478.1, YP_001671460.1, YP_001685569.1, YP_001747156.1, YP_001749732.1, YP_001765463.1, YP_001766294.1, YP_001790770.1, YP_001808775.1, YP_001809596.1, YP_001859758.1, YP_001888405.1, YP_001903233.1, YP_001977571.1, YP_002229759.1, YP_002231363.1, YP_002280472.1, YP_002297678.1, YP_002543874.1, YP_002549011.1, YP_002796201.1, YP_002801960.1, YP_002875335.1, YP_002897523.1, YP_002912290.1, YP_002974935.1, YP_003060891.1, YP_003264235.1, YP_003552364.1, YP_003578319.1, YP_003591946.1, YP_003607814.1, YP_003641922.1, YP_003674025.1, YP_003692877.1, YP_003755112.1, YP_003896973.1, YP_003907026.1, YP_003912421.1, YP_004086766.1, YP_004142571.1, YP_004147141.1, YP_004228015.1, YP_004278247.1, YP_004305252.1, YP_004356916.1, YP_004361407.1, YP_004378186.1, YP_004379856.1, YP_004390782.1, YP_004472442.1, YP_004590892.1, YP_004612414.1, YP_004676537.1, YP_004693233.1, YP_004701580.1, YP_004701637.1, YP_004704442.1, YP_108931.1, YP_110490.1, YP_168667.1, YP_237931.1, YP_260624.1, YP_262985.1, YP_271307.1, YP_276987.1, YP_334171.1, YP_337172.1, YP_350660.1, YP_351134.1, YP_364386.1, YP_366340.1, YP_369710.1, YP_370582.1, YP_426342.1, YP_440141.1, YP_442361.1, YP_468848.1, YP_521636.1, YP_554363.1, YP_608454.1, YP_610700.1, YP_614980.1, YP_622254.1, YP_625753.1, YP_680590.1, YP_751687.1, YP_767071.1, YP_774090.1, YP_774932.1, YP_788372.1, YP_858562.1, YP_928515.1, YP_983084.1, YP_995622.1, ZP_00948889.1, ZP_00954344.1, ZP_00959736.1, ZP_00998881.1, ZP_01011725.1, ZP_01037109.1, ZP_01058030.1, ZP_01076707.1, ZP_01103959.1, ZP_01167926.1, ZP_01224713.1, ZP_01442907.1, ZP_01446892.1, ZP_01550953.1, ZP_01625518.1, ZP_01745731.1, ZP_01750280.1, ZP_01754305.1, ZP_01763880.1, ZP_01769626.1, ZP_01865961.1, ZP_01881393.1, ZP_01901558.1, ZP_02145337.1, ZP_02151268.1, ZP_02152332.1, ZP_02167267.1, ZP_02190082.1, ZP_02242934.1, ZP_02360937.1, ZP_02367056.1, ZP_02385477.1, ZP_02456487.1, ZP_02883670.1, ZP_03263915.1, ZP_03263990.1, ZP_03400081.1, ZP_03452573.1, ZP_03456092.1, ZP_03517291.1, ZP_03529055.1, ZP_03571515.1, ZP_03572809.1, ZP_03587785.1, ZP_03588560.1, ZP_03697266.1, ZP_03697962.1, ZP_04521092.1, ZP_04590693.1, ZP_04890914.1, ZP_04891982.1, ZP_04893793.1, ZP_04902131.1, ZP_04905327.1, ZP_04941068.1, ZP_04944536.1, ZP_04945255.1, ZP_04959332.1, ZP_04964181.1, ZP_05053721.1, ZP_05063588.1, ZP_05073059.1, ZP_05077806.1, ZP_05082750.1, ZP_05091128.1, ZP_05095488.1, ZP_05101701.1, ZP_05116783.1, ZP_05121836.1, ZP_05127756.1, ZP_05637806.1, ZP_05742087.1, ZP_05783548.1, ZP_05786261.1, ZP_05843149.1, ZP_05945960.1, ZP_06459045.1, ZP_06487195.1, ZP_06492453.1, ZP_06493162.1, ZP_06703644.1, ZP_06731146.1, ZP_06839371.1, ZP_07007312.1, ZP_07266194.1, ZP_07374050.1, ZP_07662787.1, ZP_07778196.1, ZP_07797983.1, ZP_08099459.1, ZP_08138203.1, ZP_08141719.1, ZP_08142973.1, ZP_08177102.1, ZP_08185821.1, ZP_08186468.1, ZP_08208888.1, ZP_08266590.1, ZP_08402041.1, ZP_08406891.1, ZP_08522175.1, ZP_08527488.1, ZP_08631252.1, ZP_08636687.1.

In particular, the Enzyme $E_7$, may be an aminotransferase ($E_h$) selected from the group consisting of NP_901695.1, ZP_03697266.1, AAD41041.1, YP_002796201.1, ZP_03697962.1, YP_001859758.1, YP_002229759.1, YP_001120907.1, YP_110490.1, ZP_04964181.1, YP_774932.1, YP_001766294.1, YP_001581170.1, YP_622254.1, ZP_03588560.1, YP_001809596.1, YP_370582.1, ZP_03572809.1, NP_248990.1, YP_001888405.1, ZP_04905327.1, YP_001061726.1, YP_001668026.1, ZP_01750280.1, ZP_07778196.1, EGH71404.1, NP_744329.1, YP_004147141.1, ADR61066.1, ZP_05783548.1, YP_004701637.1, YP_366340.1, YP_003264235.1, EGD03176.1, YP_001268866.1, ZP_01901558.1, ZP_05121836.1, YP_003692877.1, ZP_03517291.1, YP_002974935.1, YP_001668026.1, ADR61066.1, NP_744329.1, YP_001268866.1, YP_004701637.1, ZP_08142973.1, ADR62525.1, YP_610700.1, NP_747283.1, ADR62525.1, YP_001270391.1, YP_004704442.1, YP_610700.1, YP_001747156.1, ZP_08138203.1, ZP_07266194.1, EGH70821.1, YP_351134.1, EGH32343.1, EGH08331.1, EGH67339.1, YP_001668026.1, YP_004701637.1, YP_237931.1, ZP_03400081.1, ZP_05116783.1, ZP_01550953.1, ZP_07662787.1, YP_928515.1, YP_788372.1, YP_001021095.1, ZP_07797983.1, YP_003578319.1, YP_004305252.1, NP_248912.1, ZP_08636687.1, YP_003912421.1, YP_751687.1, ZP_08142973.1, YP_271307.1, ZP_05082750.1, YP_001417624.1, and YP_353455.1.

The phrase 'when present' used in relation to Enzyme $E_7$, refers to cells that have been genetically modified to produce ω-amino alkanoic acid ester. The cells according to any aspect of the present invention may comprise an increased expression of Enzyme $E_7$ relative to the wild type cell thus being able to produce ω-amino alkanoic acid ester. In another example, the cells according to any aspect of the present invention may also comprise no increased expression of Enzyme $E_7$ relative to the wild type cell thus not being able to produce ω-amino alkanoic acid ester. These cells may thus mainly produce ω-oxo-alkanoic acid ester. In one example, the cell comprising increased expression of Enzyme $E_6$ and not $E_7$ relative to the wild type cell may be able to produce ω-oxo-alkanoic acid ester. In another example, where the cell is not genetically modified to increase the expression of $E_6$ and not $E_7$, the cell may produce ω-hydroxy alkanoic acid ester.

Enzyme $E_h$

In particular, the Enzyme $E_h$, may be selected from the group consisting of:

3HMU_A, AAD41041.1, AAK15486.1, ABE03917.1, ADR60699.1, ADR61066.1, ADR62525.1, AEL07495.1, CAZ86955.1, EFW82310.1, EFW87681.1, EGC99983.1, EGD03176.1, EGE58369.1, EGH06681.1, EGH08331.1, EGH24301.1, EGH32343.1, EGH46412.1, EGH55033.1, EGH62152.1, EGH67339.1, EGH70821.1, EGH71404.1, EGH78772.1, EGH85312.1, EGH97105.1, EGP57596.1, NP_102850.1, NP_106560.1, NP_248912.1, NP_248990.1, NP_354026.2, NP_421926.1, NP_637699.1, NP_642792.1, NP_744329.1, NP_744732.1, NP_747283.1, NP_795039.1, NP_901695.1, XP_002943905.1, YP_001021095.1, YP_001059677.1, YP_001061726.1, YP_001066961.1,

YP_001074671.1, YP_001120907.1, YP_001140117.1, YP_001170616.1, YP_001185848.1, YP_001188121.1, YP_001233688.1, YP_001268866.1, YP_001270391.1, YP_001345703.1, YP_001412573.1, YP_001417624.1, YP_001526058.1, YP_001579295.1, YP_001581170.1, YP_001668026.1, YP_001669478.1, YP_001671460.1, YP_001685569.1, YP_001747156.1, YP_001749732.1, YP_001765463.1, YP_001766294.1, YP_001790770.1, YP_001808775.1, YP_001809596.1, YP_001859758.1, YP_001888405.1, YP_001903233.1, YP_001977571.1, YP_002229759.1, YP_002231363.1, YP_002280472.1, YP_002297678.1, YP_002543874.1, YP_002549011.1, YP_002796201.1, YP_002801960.1, YP_002875335.1, YP_002897523.1, YP_002912290.1, YP_002974935.1, YP_003060891.1, YP_003264235.1, YP_003552364.1, YP_003578319.1, YP_003591946.1, YP_003607814.1, YP_003641922.1, YP_003674025.1, YP_003692877.1, YP_003755112.1, YP_003896973.1, YP_003907026.1, YP_003912421.1, YP_004086766.1, YP_004142571.1, YP_004147141.1, YP_004228105.1, YP_004278247.1, YP_004305252.1, YP_004356916.1, YP_004361407.1, YP_004378186.1, YP_004379856.1, YP_004390782.1, YP_004472442.1, YP_004590892.1, YP_004612414.1, YP_004676537.1, YP_004693233.1, YP_004701580.1, YP_004701637.1, YP_004704442.1, YP_108931.1, YP_110490.1, YP_168667.1, YP_237931.1, YP_260624.1, YP_262985.1, YP_271307.1, YP_276987.1, YP_334171.1, YP_337172.1, YP_350660.1, YP_351134.1, YP_364386.1, YP_366340.1, YP_369710.1, YP_370582.1, YP_426342.1, YP_440141.1, YP_442361.1, YP_468848.1, YP_521636.1, YP_554363.1, YP_608454.1, YP_610700.1, YP_614980.1, YP_622254.1, YP_625753.1, YP_680590.1, YP_751687.1, YP_767071.1, YP_774090.1, YP_774932.1, YP_788372.1, YP_858562.1, YP_928515.1, YP_983084.1, YP_995622.1, ZP_00948889.1, ZP_00954344.1, ZP_00959736.1, ZP_00998881.1, ZP_01011725.1, ZP_01037109.1, ZP_01058030.1, ZP_01076707.1, ZP_01103959.1, ZP_01167926.1, ZP_01224713.1, ZP_01442907.1, ZP_01446892.1, ZP_01550953.1, ZP_01625518.1, ZP_01745731.1, ZP_01750280.1, ZP_01754305.1, ZP_01763880.1, ZP_01769626.1, ZP_01865961.1, ZP_01881393.1, ZP_01901558.1, ZP_02145337.1, ZP_02151268.1, ZP_02152332.1, ZP_02167267.1, ZP_02190082.1, ZP_02242934.1, ZP_02360937.1, ZP_02367056.1, ZP_02385477.1, ZP_02456487.1, ZP_02883670.1, ZP_03263915.1, ZP_03263990.1, ZP_03400081.1, ZP_03452573.1, ZP_03456092.1, ZP_03517291.1, ZP_03529055.1, ZP_03571515.1, ZP_03572809.1, ZP_03587785.1, ZP_03588560.1, ZP_03697266.1, ZP_03697962.1, ZP_04521092.1, ZP_04590693.1, ZP_04890914.1, ZP_04891982.1, ZP_04893793.1, ZP_04902131.1, ZP_04905327.1, ZP_04941068.1, ZP_04944536.1, ZP_04945255.1, ZP_04959332.1, ZP_04964181.1, ZP_05053721.1, ZP_05063588.1, ZP_05073059.1, ZP_05077806.1, ZP_05082750.1, ZP_05091128.1, ZP_05095488.1, ZP_05101701.1, ZP_05116783.1, ZP_05121836.1, ZP_05127756.1, ZP_05637806.1, ZP_05742087.1, ZP_05783548.1, ZP_05786246.1, ZP_05843149.1, ZP_05945960.1, ZP_06459045.1, ZP_06487195.1, ZP_06492453.1, ZP_06493162.1, ZP_06703644.1, ZP_06731146.1, ZP_06839371.1, ZP_07007312.1, ZP_07266194.1, ZP_07374050.1, ZP_07662787.1, ZP_07778196.1, ZP_07797983.1, ZP_08099459.1, ZP_08138203.1, ZP_08141719.1, ZP_08142973.1, ZP_08177102.1, ZP_08185821.1, ZP_08186468.1, ZP_08208888.1, ZP_08266590.1, ZP_08402041.1, ZP_08406891.1, ZP_08522175.1, ZP_08527488.1, ZP_08631252.1, and ZP_08636687.1.

The cell according to any aspect of the present invention, may be genetically modified to increase the expression relative to the wild type cells of enzymes $E_1$ to $E_5$. The cell may further be genetically modified to increase the expression of at least enzymes $E_6$ and/or $E_7$. In one example, the enzymes $E_1$, $E_2$, $E_3$, $E_5$ and $E_6$, may be at least one AlkB alkane hydroxylase ($E_b$) and Enzyme $E_4$ may be a wax-ester synthase ($E_f$). In particular, the AlkB alkane hydroxylase ($E_b$) comprises at least 60% sequence identity relative to SEQ ID NO:1; and the wax-ester synthase ($E_f$) comprises at least 60% sequence identity relative to SEQ ID NO:2.

In another example, when the cell according to any aspect of the present invention in genetically modified to produce at least one ω-amino alkanoic acid ester, the cell may be modified to express at least one ω-transaminase ($E_h$) which may comprise at least 60% sequence identity relative to SEQ ID NO:3.

Enzyme $E_8$

The cell according to any aspect of the present invention may be further genetically modified to decrease the expression of at least one enzyme $E_8$ that breaks down at least one of the intermediates in the process of converting alkanes to ω-functionalized carboxylic acid ester. In particular, enzyme $E_8$ may be an enzyme capable of playing a part in the fatty acid degradation capacity of the cell. In particular, $E_8$ may be selected from the list consisting of acyl-CoA dehydrogenase ($E_i$) (FadE), enoyl CoA hydratase ($E_j$) (FadB), 3-hydroxyacyl-CoA dehydrogenase ($E_k$) (FadB) and β-ketothiolase also known as 3-ketoacyl-CoA thiolase (FadA) ($E_l$).

Fatty acids are taken up and translocated across the cell membrane via a transport/acyl-activation mechanism. The first intracellular step involves the conversion of acyl-CoA to enoyl-CoA through acyl-CoA dehydrogenase ($E_i$), the latter referred to as FadE in the case of E. coli. The activity of an acyl-CoA dehydrogenase may be assayed as described in the state of art, for example by monitoring the concentration of NADH spectrophotometrically at 340 nm in 100 mM MOPS, pH 7.4, 0.2 mM Enoyl-CoA, 0.4 mM NADH. The resulting enoyl-CoA is converted to 3-ketoacyl-CoA via 3-hydroxyacyl-CoA through hydration and oxidation, catalysed by enoyl-CoA hydratase/(R)-3-hydroxyacyl-CoA dehydrogenase ($E_j/E_k$), referred to as FadB and FadJ in E. coli. Enoyl-CoA hydratase/3-hydroxyacyl-CoA dehydrogenase activity, more specifically formation of the product NADH may be assayed spectrophotometrically as described in the state of the art, for example as outlined for FadE. Finally, 3-ketoacyl-CoA thiolase ($E_l$), FadA and FadI in E. coli, catalyses the cleavage of 3-ketoacyl-CoA, to give acetyl-CoA and the input acyl-CoA shortened by two carbon atoms. The activity of ketoacyl-CoA thiolase may be assayed as described in the state of the art, for example in Antonenkov, V., et al, 1997.

In one example, the term "acyl-CoA dehydrogenase", as used herein, may be a polypeptide capable of catalysing the conversion of an acyl-CoA to enoyl-CoA, as part of the β-oxidation pathway. For example, the polypeptide FadE in E. coli (accession number: BAA77891.2) may be an acyl-CoA dehydrogenase. The term "enoyl-CoA hydratase", as used herein, also referred to as 3-hydroxyacyl-CoA dehydrogenase, refers to a polypeptide capable of catalysing the conversion of enoyl-CoA to 3-ketoacyl-CoA through hydration and oxidation, as part of the β-oxidation pathway. For example, the polypeptides FadB and FadJ in E. coli (accession numbers: BAE77457.1 and P77399.1, respectively) are enoyl-CoA hydratases. The term "ketoacyl-CoA thiolase", as used herein, may refer to a polypeptide capable of catalysing the cleaving of 3-ketoacyl-CoA, resulting in an acyl-CoA shortened by two carbon atoms and acetyl-CoA, as the final step of the β-oxidation pathway. For example, the polypeptides FadA and FadI in *E. coli* (accession number: YP_491599.1 and P76503.1, respectively) are ketoacyl-CoA thiolases.

Enzymes $E_9$ and $E_{10}$

The cell according to any aspect of the present invention may be genetically modified further to increase the expression relative to the wild type cell of:

the Enzyme $E_9$ is a fatty acyl-Coenzyme A methyl ester esterase BioH ($E_m$); and/or the Enzyme $E_{10}$ is a fatty acyl-Coenzyme A thioesterase ($E_n$) selected from the group consisting of TesA, TesB, YciA, FadM, YbfF and YbgC.

In particular, $E_m$ may be capable of hydrolyzing fatty acid esters to free fatty acids and the respective alcohol; and/or $E_n$ may be capable of hydrolyzing fatty acyl-Coenzyme A to free fatty acids and Coenzyme A.

Enzyme $E_{11}$

The cell according to any aspect of the present invention may comprise a further genetic mutation that increases the expression of at least one transporter protein relative to the wild type cell. This further mutation enables the cell to increase the uptake of at least one fatty acid. In particular, the transporter protein may be AlkL (SEQ ID NO: 4 or 5) and/or FadL (SEQ ID NO: 6). AlkL and/or FadL may function as at least one transporter protein compared to the wild type cell. In one example, the cell may be genetically modified to overexpress both the fadL and the alkL gene. The cell according to any aspect of the present invention may be genetically modified further to increase the expression relative to the wild type cell of AlkL and/or FadL.

In one example, the enzyme $E_{11}$ may be FadL or BAA16205.1

Enzyme $E_{12}$

The cell according to any aspect of the present invention may comprise a further genetic mutation that increases the expression relative to the wild type cell of an acyl-CoA synthetase (Enzyme $E_{12}$) of EC 6.2.1.3, EC 2.3.1.86. Enzyme $E_{12}$ may catalyse the conversion of a fatty acid to the CoA ester of a fatty acid, i.e. a molecule, wherein the functional group —OH of the carboxy group is replaced with —S—CoA. For example, the polypeptides FadD and FadK in *E. coli* (accession number: BAA15609.1 and NP_416216.4, respectively) are acyl-CoA synthetases. In another example, $E_{12}$ may be a long-chain-fatty-acid-CoA ligase of YP_001724804.1.

Enzyme $E_{13}$

Enzyme $E_{13}$ may be capable of converting ω-oxo alkanoic acid ester to the corresponding ω-carboxy alkanoic acid ester, In particular, Enzyme $E_{13}$ may be any enzyme $B_3$ defined above. More in particular, $E_{13}$ may be selected from the group consisting of P450 alkane hydroxylases ($E_a$) of EC 1.14.15.3-, AlkB alkane hydroxylases ($E_b$) of EC 1.14.15.3, bifunctional alcohol oxidases ($E_c$) of EC 1.1.3.20, bifunctional AlkJ alcohol dehydrogenases ($E_{di}$) or bifunctional alcohol dehydrogenases ($B_{dii}$) of EC 1.1.1.1 or EC 1.1.1.2, capable of oxidizing an ω-hydroxy alkanoic acid ester via an ω-oxo alkanoic acid ester directly to the corresponding ω-carboxy alkanoic acid ester; and aldehyde dehydrogenases ($E_e$).

Enzyme $E_{14}$

Enzyme $E_{14}$ may be capable of converting ω-carboxy alkanoic acid ester to the corresponding ω-carboxy alkanoic acid diester. In particular, Enzyme $E_{14}$ may be any enzyme $E_4$ defined above. More in particular, $E_{14}$ may be at least one wax-ester synthase ($E_f$) or an alcohol O-acyl transferase ($E_g$) (EC 2.3.1.20, EC 2.3.1.75 or EC 2.3.1.84).

The cell according to any aspect of the present invention does not comprise a genetic modification that increases the expression relative to the wild type cell of at least one of the following enzymes $E_{20}$-$E_{24}$ selected from the group consisting of:

$E_{20}$ Acyl-ACP thioesterase, of EC 3.1.2.14 or EC 3.1.2.22, $E_{21}$ Acyl-CoA thioesterase, of EC 3.1.2.2, EC 3.1.2.18, EC 3.1.2.19, EC 3.1.2.20 or EC 3.1.2.22, $E_{22}$ Acyl-CoA:ACP transacylase, $E_{23}$ Polyketide synthase, and $E_{24}$ Hexanoic acid synthase.

In particular, the cell according to any aspect of the present invention has a wild type expression of enzymes $E_{20}$-$E_{24}$. Enzymes $E_{20}$-$E_{24}$ are thus neither overexpressed nor knocked out in the cells according to the method of the present invention. More in particular, the expression of any one of enzymes $E_{20}$-$E_{24}$, that is to say enzyme $E_{20}$, $E_{21}$, $E_{22}$, $E_{23}$ or $E_{24}$ all enzymes $E_{20}$, $E_{21}$, $E_{22}$, $E_{23}$ and $E_{24}$ are not genetically modified in the cell according to any aspect of the present invention. Even more in particular, the cell according to any aspect of the present invention may comprise the natural, wild type expression of any of the enzymes $E_{20}$-$E_{24}$ that may be naturally present in the cell to begin with. The cells according to any aspect of the present invention may thus be considered to comprise no recombinant expression of any one of enzymes $E_{20}$-$E_{24}$. This is especially advantageous as cells without increased expression of any one of enzymes $E_{20}$-$E_{24}$ (that is with wild type expression of any one of enzymes $E_{20}$-$E_{24}$) may then readily select to use an alkane as a carbon source for ω-functionalized carboxylic acid ester formation. In particular, any cell with increased expression of any one of enzymes $E_{20}$-$E_{24}$ may result in increased production of fatty acids which may be used as the carbon source for formation of ω-functionalized carboxylic acids and/or esters thereof by the cell with increased expression of any one of enzymes $E_{20}$-$E_{24}$. The cells with increased expression of any one of enzymes $E_{20}$-$E_{24}$ may thus favour the use of the high concentration of fatty acids as a substrate for production of ω-functionalized carboxylic acid esters and alkanes will thus not be used for ω-functionalized carboxylic acid ester formation by the cell. The use of other carbon sources other than alkanes for ω-functionalized carboxylic acid ester formation may increase the costs of production drastically as to produce more fatty acids, the cells would require other sources of carbon such as glucose. Accordingly, the use of cells according to any aspect of the present invention which do not comprise a genetic modification that increases the expression relative to the wild type cell of at least one of the following enzymes $E_{20}$-$E_{24}$ are used according to any aspect of the present invention for production of at least one ω-functionalized carboxylic acid ester from at least one alkane.

Enzymes $E_{20}$-$E_{24}$

Enzymes $E_{20}$-$E_{24}$ are explained in detail in WO2013024114 as enzymes $E_i$ to $E_{iv}$ respectively on pages 60-79 of WO2013024114.

According to another aspect of the present invention, there is provided a method of producing at least one ω-functionalized carboxylic acid ester, wherein the method comprises a step of contacting at least one cell according to any aspect of the present invention with at least one alkane. In particular, the ω-functionalized carboxylic acid ester formed may be selected from the group consisting of ω-hydroxy-alkanoic acid, ω-oxo-alkanoic acid, ω-carboxy-alkanoic acid, ω-amino-alkanoic acid esters. In particular, the ω-functionalized carboxylic acid ester may be 12-amino lauric acid methyl ester, 12-hydroxy lauric acid methyl ester, 12-carboxy lauric acid methyl (di) ester and/or lauric acid methyl ester and the alkane dodecane. In another example, the ω-functionalized carboxylic acid ester produced may be 11-amino undecanoic acid methyl ester, 11-hydroxy undecanoic acid methyl ester, 11-carboxy undecanoic acid methyl (di) ester and/or undecanoic acid methyl ester from the alkane undecane. In at least one further example, monofunctional alcohols and/or aldehydes may be formed as a by-product.

The term "contacting", as used herein, means bringing about direct contact between the alkane and/or the cell according to any aspect of the present invention in an aqueous solution. For example, the cell and the alkane may not be in different compartments separated by a barrier such as an inorganic membrane. If the alkane is soluble and may be taken up by the cell or can diffuse across biological membranes, it may simply be added to the cell according to any aspect of the present invention in an aqueous solution. In case it is insufficiently soluble, it may be solved in a suitable organic solvent prior to addition to the aqueous solution. The person skilled in the art is able to prepare aqueous solutions of alkanes having insufficient solubility by adding suitable organic and/or polar solvents. Such solvents may be provided in the form of an organic phase comprising liquid organic solvent. In one example, the organic solvent or phase may be considered liquid when liquid at 25° C. and standard atmospheric pressure. In another example, a fatty acid may be provided in the form of a fatty acid ester such as the respective methyl or ethyl ester. In another example, the compounds and catalysts may be contacted in vitro, i.e. in a more or less enriched or even purified state, or may be contacted in situ, i.e. they are made as part of the metabolism of the cell and subsequently react inside the cell.

The term "an aqueous solution" is used interchangeably with the term 'aqueous medium" and refers to any solution comprising water, mainly water as solvent that may be used to keep the cell according to any aspect of the present invention, at least temporarily, in a metabolically active and/or viable state and comprises, if such is necessary, any additional substrates. The person skilled in the art is familiar with the preparation of numerous aqueous solutions, usually referred to as media that may be used to keep inventive cells, for example LB medium in the case of *E. coli*. It is advantageous to use as an aqueous solution a minimal medium, i.e. a medium of reasonably simple composition that comprises only the minimal set of salts and nutrients indispensable for keeping the cell in a metabolically active and/or viable state, by contrast to complex mediums, to avoid dispensable contamination of the products with unwanted side products. For example, M9 medium may be used as a minimal medium.

According to another aspect of the present invention, there is provided a method of producing at least one ω-functionalized carboxylic acid ester from an alkane, wherein the method comprises:
(a) contacting the following enzymes with the alkane:
  (i) Enzyme $E_1$ capable of converting the alkane to the corresponding 1-alkanol;
  (ii) Enzyme $E_2$ capable of converting the 1-alkanol of (i) to the corresponding 1-alkanal;
  (iii) Enzyme $E_3$ capable of converting the 1-alkanal of (ii) to the corresponding alkanoic acid;
  (iv) Enzyme $E_4$ capable of converting the alkanoic acid of (iii) to the corresponding alkanoic acid ester; and
  (v) Enzyme $E_5$ capable of converting the alkanoic acid ester of (iv) to the corresponding ω-hydroxy-alkanoic acid ester.

The method according to any aspect of the present invention may comprise a step of
(b) contacting the following enzymes with the ω-hydroxy-alkanoic acid ester:
  (vi) Enzyme $E_6$ capable of converting the corresponding ω-hydroxy-alkanoic acid ester of (v) to the corresponding ω-oxo alkanoic acid ester; or
  (vii) Enzyme $E_6$ capable of converting the corresponding ω-hydroxy-alkanoic acid ester of (v) to the corresponding ω-oxo alkanoic acid ester and Enzyme $E_7$ capable of converting the ω-oxo alkanoic acid ester to the corresponding ω-amino alkanoic acid ester; or
  (viii) Enzyme $E_6$ capable of converting the corresponding ω-hydroxy-alkanoic acid ester of (v) to the corresponding ω-oxo alkanoic acid ester and Enzyme $E_{13}$ capable of converting the ω-oxo alkanoic acid ester to the corresponding ω-carboxy alkanoic acid ester and Enzyme $E_{14}$ capable of converting the ω-carboxy alkanoic acid ester to the corresponding ω-carboxy alkanoic acid diester.

The enzymes used according to any aspect of the present invention may be the same as the enzymes disclosed in the context of the cell according to the present invention.

Having generally described this invention, a further understanding can be obtained by reference to certain specific examples which are provided herein for purposes of illustration only, and are not intended to be limiting unless otherwise specified.

EXAMPLES

The foregoing describes preferred embodiments, which, as will be understood by those skilled in the art, may be subject to variations or modifications in design, construction or operation without departing from the scope of the claims. These variations, for instance, are intended to be covered by the scope of the claims.

Example 1

Production of lauric acid (methyl ester) and undecanoic acid (methyl ester) from dodecane and undecane (as well as methanol in case of the methyl esters), respectively, with a whole-cell biocatalyst harbouring an alkane monooxygenase and a wax ester synthase and attenuated in an enzymes catalyzing degradation of fatty acids and an enzyme hydrolyzing fatty acid esters to free fatty acids and the respective alcohol.

Example 2

Production of 12-amino lauric acid methyl ester and 11-amino undecanoic acid methyl ester from dodecane and undecane, respectively, with a whole-cell biocatalyst harbouring an alkane monooxygenase, a wax ester synthase and an ω-transaminase and attenuated in an enzymes catalyzing degradation of fatty acids and an enzyme hydrolyzing fatty acid esters to free fatty acids and the respective alcohol.

Example 3

Construction of an Expression Vector for Overexpression of the *E. coli* fadD Gene and an *Hahella Chejuensis* Gene Encoding a Wax Ester Synthase The vector pCDF-fadD_Ec-wes_Hche (SEQ ID NO:7) harbors the genes fadD from *E. coli* (encoding an acyl-CoA synthase) and a wax ester synthase gene from *Hahella chejuensis* (SEQ ID NO:2), codon-optimized for expression in *E. coli*. While the acyl-CoA synthase is responsible for activation of fatty acids to the corresponding CoA thioesters, the wax ester synthase is required for ester formation between a fatty acyl-CoA and an alcohol, more specifically methanol. The vector is based on plasmid pCDFDuet-1 (Merck Biosciences; Nottingham, UK) and harbors the fadD gene under control of the tac promoter and the *Hahella chejuensis* wax ester synthase-encoding gene under control of the T5 promoter. *E. coli* fadD as well as the tac and T5 promoter cassettes were amplified by PCR from genomic DNA of *E. coli* W3110, respectively, the *Hahella chejuensis* wax ester synthase-encoding gene was obtained by DNA synthesis. The vector backbone and the four DNA fragments representing *E. coli* fadD, the tac and T5 promoter cassettes and the *Hahella chejuensis* wax ester synthase-encoding gene were fused using a commercially available kit for in vitro recombination (NEBuilder HiFi DNA Assembly Cloning Kit; NEB; Frankfurt/Main, Germany) to give vector pCDF-fadD_Ec-wes_Hche (SEQ ID NO:7).

Example 4

Construction of *E. coli* Strains Capable of Converting Alkanes to the Corresponding ω-Functionalized Fatty Acid Methyl Esters The expression vector pBT10_alkL (see Example 1 of WO/2011/131420 for construction details and the listed SEQ ID NO: 8) contains the genes alkB, alkG, alkT, alkS and alkL from the alk operon of *Pseudomonas oleovorans*. The corresponding gene products catalyzed oxidation of alkanes to the corresponding alkanols, alkanals and fatty acids (AlkBGT) as well as the uptake of the substrates (AlkL). In addition, the AlkBGT gene products also catalyzed the oxidation of fatty acid methyl esters, once formed by action of the enzymes acyl-CoA synthetase and wax ester synthase from fatty acids and methanol (see Example 1). The vector pJ294_alaDH_B.s._TA_C.v.(Ct) (see Example 1 of WO/2013/024114 for construction details and the listed SEQ ID NO: 17) harbors the genes ald from *Bacillus subtilis* (encoding an alanine dehydrogenase) and Cv_2505 from *Chromobacterium violaceum* (encoding an ω-transaminase). While the ω-transaminase is responsible for conversion of OLAME and OUAME to the corresponding amines ALAME and AUAME, alanine dehydrogenase was required for provision of the amine donor alanine from pyruvate and inorganic ammonia.

The plasmids pBT10_alkL and pCDF-fadD_Ec-wes_Hche plus when appropriate pJ294_alaDH_B.s._TA_C.v.(Ct) were transformed via electroporation into *E. coli* W3110 ΔbioH ΔfadE, plated onto LB agar plates with kanamycin (50 µg/ml), ampicillin (100 µg/ml) and spectinomycin (100 µg/ml) as applicable. Transformants were screened for presence and authenticity of the plasmids by plasmid preparation and restriction digest analysis. The following strains were generated:

*E. coli* W3110 ΔbioH ΔfadE pBT10_alkL/pCDF-fadD_Ec-wes_Hche

*E. coli* W3110 ΔbioH ΔfadE pBT10_alkL/pJ294_alaDH_B.s._TA_C.v.(Ct)/pCDF-fadD_Ec-wes_Hche

Example 5

Biotransformation for Conversion of Alkanes to the Corresponding ω-Functionalized Fatty Acid Methyl Esters The strains *E. coli* W3110 ΔbioH ΔfadE pBT10_alkL/pCDF-fadD_Ec-wes_Hche and *E. coli* W3110 ΔbioH ΔfadE pBT10_alkL/pJ294_alaDH_B.s._TA_C.v.(Ct)/pCDF-fadD_Ec-wes_Hche were subjected to fed-batch fermentation followed by biotransformation in order to investigate their ability to produce omega-hydroxylauric acid methylester (HLAME), omega-oxolauric acid methylester (OLAME), omega-aminolauric acid methylester (ALAME), dodecanedioic acid monomethylester (DDAME) and dodecanedioic acid dimethylester (DDADME) from dodecane. The strains were also subjected to a fed-batch fermentation followed by biotransformation in order to investigate their ability to produce omega-hydroxyundecanoic acid methylester (HUAME), omega-oxoundecanoic acid methylester (OUAME), omega-aminoundecanoic acid methylester (AUAME), undecanedioic acid monomethylester (UDAME) and undecanedioic acid dimethylester (UDADME) from undecane. This was carried out in an 8-fold parallel fermentation system from DASGIP.

For the fermentation, 1 l reactors were used which were equipped with overhead stirrers and impeller turbines. To monitor the process, pH and $pO_2$ were measured online OTR/CTR measurements served inter alia for estimating the metabolic activity and fitness of the cells.

The pH probes were calibrated by means of a two-point calibration with measurement solutions of pH 4.0 and pH 7.0 according to technical references provided by DASGIP. The reactors were prepared according to technical references provided by DASGIP with the required sensors and connections and the stirrer shaft was installed. The reactors were then filled with 300 ml of water and autoclaved for 20 min at 121° C. in order to ensure sterility. The $pO_2$ probes were polarized overnight (at least 6 h) following connection to the measurement amplifier. The water was then removed under the clean bench and replaced by high-cell-density medium consisting of $(NH_4)_2SO_4$ 1.76 g/l, $K_2HPO_4$ 19.08 g/l, $KH_2PO_4$ 12.5 g/l, yeast extracts 6.66 g/l, trisodium citrate dihydrate 11.2 g/l, 17 ml/l of a filter-sterilized 1% strength ammonium iron citrate solution, and 5 ml/l of a filter-sterilized trace element stock solution (consisting of HCl (37%) 36.50 g/l, $MnCl_2*4 H_2O$ 1.91 g/l, $ZnSO_4*7 H_2O$ 1.87 g/l, ethylenediaminetetraacetic acid dihydrate 0.84 g/l, $H_3BO_3$ 0.30 g/l, $Na_2MoO_4*2 H_2O$ 0.25 g/l, $CaCl_2*2 H_2O$ 4.70 g/l, $FeSO_4*7 H_2O$ 17.80 g/l, $CuCl2*2 H2O$ 0.15 g/l) with 15 g/l glucose as carbon source (added by metered addition of 30 ml/l of a sterile feed solution consisting of 500 g/l glucose, 1% (w/v) $MgSO_4*7 H_2O$ and 2.2% (w/v) $NH_4Cl$) with 50 mg/l kanamycin.

Subsequently, the $pO_2$ probes were calibrated using a single-point calibration (stirrer: 600 rpm/gassing: 10 sL/h air) to 100% and the feed, correction agent and induction agent stretches were cleaned by means of cleaning-in-place according to technical references provided by DASGIP. For this, the tubes were firstly flushed with 70% ethanol, then with 1 M NaOH, subsequently with sterile demineralized water and finally filled with the respective media.

All of the aforementioned *E. coli* strains were cultured firstly from a cryoculture in LB medium (25 ml in a 100 ml baffled shake flask) with 50 mg/l kanamycin overnight at 37° C. and 200 rpm for about 18 h. Then, 2 ml of this culture were transferred for a second preculture stage into 25 ml of high-cell-density medium consisting of $(NH_4)_2SO_4$ 1.76 g/L, $K_2HPO_4$ 19.08 g/l, $KH_2PO_4$ 12.5 g/l, yeast extract 6.66 g/l, trisodium citrate dihydrate 11.2 g/l, 17 ml/l of a filter-sterilized 1% strength ammonium iron citrate solution, and 5 ml/l of a filter-sterilized trace element stock solution (consisting of HCl (37%) 36.50 g/l, $MnCl_2*4\ H_2O$ 1.91 g/l, $ZnSO_4*7\ H_2O$ 1.87 g/l, ethylenediaminetetraacetic acid dihydrate 0.84 g/l, $H_3BO_3$ 0.30 g/l. $Na_2MoO_4*2\ H_2O$ 0.25 g/l, $CaCl_2*2\ H_2O$ 4.70 g/l, $FeSO_4*7\ H_2O$ 17.80 g/l, $CuCl_2*2\ H_2O$ 0.15 g/l) with 15 g/l glucose as carbon source (added by metered addition of 30 ml/l of a sterile feed solution consisting of 500 g/l glucose, 1% (w/v) $MgSO_4*7\ H_2O$ and 2.2% (w/v) $NH_4Cl$) with the already described antibiotics in a 100 ml shake flask and incubated at 37° C./200 rpm for a further 6 h.

In order to inoculate the reactors with an optical density of 0.1, the $OD_{600}$ of the second preculture stage was measured and the amount of culture required for the inoculation was calculated. The required amount of culture was added with the help of a 5 ml syringe through a septum into the heat-treated and aerated reactor.

The following standard program was used:

| | DO regulator | | pH regulator |
|---|---|---|---|
| Preset | 0% | Preset | 0 ml/h |
| P | 0.1 | P | 5 |
| Ti | 300 s | Ti | 200 s |
| min | 0% | min | 0 ml/h |
| max | 100% | max | 40 ml/h |

| N (Rotation) | from | to | XO2 (gas mixture) | from | to | F (gas flow rate) | from | to |
|---|---|---|---|---|---|---|---|---|
| growth and biotransformation | 0% 400 rpm | 30% 1500 rpm | growth and biotransformation | 0% 21% | 100% 21% | growth and biotransformation | 15% 6 sL/h | 80% 72 sL/h |

| Script | |
|---|---|
| Trigger sharp | 31% DO (1/60 h) |
| Induction | 10 h after feed start |
| DCPK | |
| Feed trigger | 50% DO |
| Feed rate | 3 [ml/h] |

The pH was regulated to pH 6.8 on one side with 12.5% strength ammonia solution. During cultivation and biotransformation, the dissolved oxygen ($pO_2$ or DO) in the culture was regulated to at least 30% by means of stirrer feed and gassing rate. Following inoculation, the DO dropped from 100% to 30%, where it was kept stable for the remainder of the fermentation.

The fermentation was carried out as fed-batch, where the feed start was triggered as delivery to the feed phase with 5 g/l*h glucose feed, consisting of 500 g/l glucose, 1% (w/v) $MgSO_4*7\ H_2O$ and 2.2% (w/v) $NH_4Cl$, via the DO peak inducing the end of the batch phase. With feed start, the temperature of 37° C. was lowered to 30° C. 10 h after feed start, the expression of the oxidation genes was induced with 0.025% (v/v) DCPK. The start of the production (=start of the biotransformation) was carried out 14 h after feed start. For this purpose, 150 ml of dodecane or undecane were added as batch to the fermentation broth.

To quantify LSME and HLS in fermentation samples, samples were taken 1/2/4/20/22 h after the start of biotransformation. These samples were prepared for analysis as provided in Example 6.

Example 6

LC-ESI/$MS^2$-Based Quantification of Products

The quantification of HLAME, OLAME, ALAME, DDAME and DDADME as well as of HUAME, OUAME, AUAME, UDAME and UDADME in fermentation samples was carried out by means of LC-ESI/$MS^2$ by reference to an external calibration for all analytes (0.1-50 mg/l) and using the internal standard aminoundecanoic acid (AUA for HLSME), and d3-LSME (for LSME).

The following instruments were used here:
- HPLC system 1260 (Agilent; Böblingen) with autosampler (G1367E), binary pump (G1312B) and column oven (G1316A)
- Mass spectrometer TripelQuad 6410 (Agilent; Böblingen) with ESI source
- HPLC column: Kinetex C18, 100×2.1 mm, particle size: 2.6 µm, pore size 100 Å (Phenomenex; Aschaffenburg)
- Precolumn: KrudKatcher Ultra HPLC In-Line Filter; 0.5 µm filter depth and 0.004 mm internal diameter (Phenomenex; Aschaffenburg)

The samples were prepared by pipetting 1900 µl of solvent (80% (v/v) acetonitrile, 20% double-distilled $H_2O$ (v/v), +0.1% formic acid) and 100 µl sample in a 2-ml reaction vessel. The mixture was vortexed for about 10 seconds and then centrifuged at about 13 000 rpm for 5 min. The clear supernatant was removed using a pipette and, after appropriate dilution, analyzed with diluents (80% (v/v) ACN, 20% double-distilled. $H_2O$ (v/v), +0.1% formic acid). 100 µL of ISTD were pipetted into each 900 µL sample (10 µL for a sample volume of 90 µL).

The HPLC separation was carried out with the aforementioned column and precolumn. The injection volume was 0.7 µL, the column temperature 50° C., the flow rate 0.6 mL/min. The mobile phase consisted of eluent A (0.1% (v/v) aqueous formic acid) and eluent B (acetonitrile with 0.1% (v/v) formic acid). The following gradient profile was used:

| Time [min] | Eluent A [%] | Eluent B [%] |
|---|---|---|
| 0 | 77 | 23 |
| 0.3 | 77 | 23 |
| 0.4 | 40 | 60 |
| 2.5 | 40 | 60 |
| 2.6 | 2 | 98 |
| 5.5 | 2 | 98 |
| 5.6 | 77 | 23 |
| 9 | 77 | 23 |

The ESI-MS$_2$ analysis was carried out in positive ionization mode with the following parameters of the ESI source:
Gas temperature 280° C.
Gas flow rate 11 L/min
Nebulizing pressure 50 psi
Capillary voltage 4000 V
The detection and quantification of the compounds HLAME, OLAME, ALAME, DDAME, DDADME, HUAME, OUAME, AUAME, UDAME and UDADME was carried out with the following MRM parameters, with in each case a product ion being used as qualifier and one as quantifier.

TABLE 1

The analytes LA und LAME were detected in SIM modus (m/z 201 and 215).

| Analyte | Precursor ion [m/z] | Production [m/z] | Hold-up time [ms] | Collision energy [eV] |
| --- | --- | --- | --- | --- |
| DDSME | 245.2 | 167.1 | 25 | 6 |
| DDSME | 245.2 | 149.1 | 50 | 8 |
| HLSME | 231.3 | 181.2 | 15 | 2 |
| HLSME | 231.3 | 163.2 | 25 | 5 |
| DDS | 231.2 | 213.2 | 50 | 0 |
| DDS | 231.2 | 149.1 | 25 | 9 |
| ALSME | 230.3 | 198.1 | 25 | 10 |
| ALSME | 230.3 | 163.2 | 15 | 10 |
| OLSME | 229.2 | 197.2 | 50 | 0 |
| OLSME | 229.2 | 161.1 | 25 | 5 |
| HLS | 217.2 | 181.2 | 35 | 0 |
| HLS | 217.2 | 163.1 | 20 | 4 |
| OLS | 215.2 | 161.2 | 25 | 0 |
| OLS | 215.2 | 95.2 | 60 | 13 |

Example 7

Conversion of Alkanes to the Corresponding ω-Functionalized Fatty Acid Methyl Esters by *E. coli* W3110 ΔbioH ΔfadE pBT10_alkL/pCDF-fadD_Ec-wes_Hche and *E. coli* W3110 ΔbioH ΔfadE pBT10_alkL/pJ294_alaDH_B.s._TA_C.v.(Ct)/pCDF-fadD_Ec-wes_Hche Using the above described protocols *E. coli* W3110 ΔbioH ΔfadE pBT10_alkL/pCDF-fadD_Ec-wes_Hche could be shown to produce DDAME and DDADME from dodecane as well as UDAME and UDADME from undecane (see Tables 1 and 2). Moreover, *E. coli* W3110 ΔbioH ΔfadE pBT10_alkL/pJ294_alaDH_B.s._TA_C.v.(Ct)/pCDF-fadD_Ec-wes_Hche could be shown to produce HLAME and ALAME from dodecane as well as HUAME and AUAME from undecane (see Tables 2 and 3).

TABLE 2

Concentration of ω-functionalized fatty acid methyl esters formed from dodecane with strains *E. coli* W3110 ΔbioH ΔfadE pBT10_alkL/pCDF-fadD_Ec-wes_Hche (Strain 1) and *E. coli* W3110 ΔbioH ΔfadE pBT10_alkL/pJ294_alaDH_B.s._TA_C.v.(Ct)/pCDF-fadD_Ec-wes_Hche (Strain 2).

| Strain | $c_{HLAME}$ [mg * L$^{-1}$] | $c_{OLAME}$ [mg * L$^{-1}$] | $c_{ALAME}$ [mg * L$^{-1}$] | $c_{DDAME}$ [mg * L$^{-1}$] | $c_{DDADME}$ [mg * L$^{-1}$] |
| --- | --- | --- | --- | --- | --- |
| Strain 1 | ND | ND | ND | 50 | 24 |
| Strain 2 | 50 | ND | 60 | ND | 12 |

TABLE 3

Concentration of ω-functionalized fatty acid methyl esters formed from undecane with strains *E. coli* W3110 ΔbioH ΔfadE pBT10_alkL/pCDF-fadD_Ec-wes_Hche (Strain 1) and *E. coli* W3110 ΔbioH ΔfadE pBT10_alkL/pJ294_alaDH_B.s._TA_C.v.(Ct)/pCDF-fadD_Ec-wes_Hche (Strain 2).

| Strain | $c_{HUAME}$ [g * L$^{-1}$] | $c_{OLAME}$ [g * L$^{-1}$] | $c_{AUAME}$ [g * L$^{-1}$] | $c_{DUAME}$ [g * L$^{-1}$] | $c_{DUADME}$ [g * L$^{-1}$] |
| --- | --- | --- | --- | --- | --- |
| Strain 1 | 10 | ND | ND | 50 | 45 |
| Strain 2 | 30 | ND | 10 | ND | tbd |

European patent application 15196180.2 filed Nov. 25, 2016, is incorporated herein by reference. Numerous modifications and variations on the present invention are possible in light of the above teachings. It is therefore to be understood that within the scope of the appended claims, the invention may be practiced otherwise than as specifically described herein.

The invention claimed is:

1. A microbial cell, which is genetically modified to increase the expression relative to the corresponding genetically unmodified cell of an AlkB alkane hydroxylase ($E_b$) having an amino acid sequence at least 95% identical with the amino acid sequence of SEQ ID NO: 1 and a wax-ester synthase ($E_f$) having an amino acid sequence at least 95% identical with the amino acid sequence of SEQ ID NO: 2,
   wherein the cell does not comprise a genetic modification that increases formation of a carboxylic acid or a carboxylate ester from a simple carbon source.

2. The cell according to claim 1,
   wherein the AlkB alkane hydroxylase ($E_b$) has the amino acid sequence of SEQ ID NO:1, and
   the wax-ester synthase ($E_f$) has the amino acid sequence of SEQ ID NO:2.

3. The cell according to claim 2,
   wherein the cell is further genetically modified to increase the expression relative to the corresponding genetically unmodified cell of *Escherichia coli* FadD.

4. The cell according to claim 1, wherein the cell is selected from the group consisting of *Escherichia coli, Pseudomonas* sp., *Pseudomonas fluorescens, Pseudomonas putida, Pseudomonas stutzeri, Acinetobacter* sp., *Burkholderia* sp., *Burkholderia thailandensis, Cyanobakterien, Klebsiella* sp., *Klebsiella oxytoca, Salmonella* sp., *Rhizobium* sp. and *Rhizobium meliloti, Bacillus* sp., *Bacillus subtilis, Clostridium* sp., *Corynebacterium* sp., *Corynebacterium glutamicum, Brevibacterium* sp., *Chlorella* sp. and *Nostoc* sp.

5. The cell according to claim 4, wherein
   the AlkB alkane hydroxylase ($E_b$) has an amino acid sequence at least 99% identical with the amino acid sequence of SEQ ID NO:1; and
   the wax-ester synthase ($E_f$) has an amino acid sequence at least 99% identical with the amino acid sequence of SEQ ID NO:2.

6. The cell according to claim 5, wherein the cell is further genetically modified to increase the expression relative to the corresponding genetically unmodified cell of *Escherichia coli* FadD.

7. The cell according to claim 1, wherein the cell is *Escherichia coli* and is genetically modified to have at least one vector comprising at least one gene encoding the AlkB alkane hydroxylase ($E_b$) and the wax-ester synthase ($E_f$) such that the expression of the AlkB alkane hydroxylase ($E_b$) and the wax-ester synthase ($E_f$) is increased.

8. The cell according to claim 4,
   wherein the AlkB alkane hydroxylase ($E_b$) has the amino acid sequence of SEQ ID NO:1, and
   the wax-ester synthase ($E_f$) has the amino acid sequence of SEQ ID NO:2.

9. The cell according to claim 8,
   wherein the cell is further genetically modified to increase the expression relative to the corresponding genetically unmodified cell of *Escherichia coli* FadD.

10. The cell according to claim 1, wherein the AlkB alkane hydroxylase ($E_b$) has an amino acid sequence at least 98% identical with the amino acid sequence of SEQ ID NO:1; and
    the wax-ester synthase ($E_f$) has an amino acid sequence at least 98% identical with the amino acid sequence of SEQ ID NO:2.

11. The cell according to claim 1, wherein
    the AlkB alkane hydroxylase ($E_b$) has an amino acid sequence at least 99% identical with the amino acid sequence of SEQ ID NO:1; and
    the wax-ester synthase ($E_f$) has an amino acid sequence at least 99% identical with the amino acid sequence of SEQ ID NO:2.

12. The cell according to claim 1, wherein the cell is further genetically modified to increase the expression relative to the corresponding genetically unmodified cell of an acyl-CoA synthetase.

13. The cell according to claim 1, wherein the cell is further genetically modified to increase the expression relative to the corresponding genetically unmodified cell of *Escherichia coli* FadD.

14. The cell according to claim 4, wherein the AlkB alkane hydroxylase ($E_b$) has an amino acid sequence at least 98% identical with the amino acid sequence of SEQ ID NO: 1; and
    the wax-ester synthase ($E_f$) has an amino acid sequence at least 98% identical with the amino acid sequence of SEQ ID NO: 2.

15. The cell according to claim 4, wherein the cell is further genetically modified to increase the expression relative to the corresponding genetically unmodified cell of an acyl-CoA synthetase.

16. The cell according to claim 1, wherein the cell is further genetically modified to increase the expression relative to the corresponding genetically unmodified cell of enzyme $E_7$, wherein the enzyme $E_7$ is capable of converting an ω-oxo alkanoic acid ester to a corresponding ω-amino alkanoic acid ester, and wherein the enzyme $E_7$ is an ω-transaminase ($E_h$).

17. The cell according to claim 16, wherein the ω-transaminase ($E_h$) has an amino acid sequence at least 95% identical with the amino acid sequence of SEQ ID NO:3.

18. A method of producing at least one ω-functionalized carboxylic acid ester, comprising contacting the microbial cell according to claim 1 with an aqueous solution comprising an alkane, wherein
    (a) the alkane comprises dodecane, and the at least one ω-functionalized carboxylic acid ester comprises at least one selected from the group consisting of 12-amino lauric acid methyl ester, 12-hydroxy lauric acid methyl ester, 12-carboxy lauric acid methyl (di) ester, and lauric acid methyl ester, or
    (b) the alkane comprises undecane, and the at least one ω-functionalized carboxylic acid ester comprises at least one selected from the group consisting of 11-amino undecanoic acid methyl ester, 11-hydroxy undecanoic acid methyl ester, 11-carboxy undecanoic acid methyl (di) ester, and undecanoic acid methyl ester.

* * * * *